United States Patent
Duffy et al.

(10) Patent No.: US 12,297,201 B2
(45) Date of Patent: May 13, 2025

(54) SUBSTITUTED PYRROLO[2,3-D]PYRIMIDINES AS ANTIMICROBIALS

(71) Applicant: BIOVERSYS AG, Basel (CH)

(72) Inventors: Erin M. Duffy, Deep River, CT (US); Ashoke Bhattacharjee, Cheshire, CT (US); Zoltan F. Kanyo, North Haven, CT (US); Joseph A. Ippolito, Guilford, CT (US); Andrea Marra, New Haven, CT (US)

(73) Assignee: Bioversys AG, Basel (CH)

( * ) Notice: Subject to any disclaimer, the term of this patent is extended or adjusted under 35 U.S.C. 154(b) by 0 days.

(21) Appl. No.: 18/134,949

(22) Filed: Apr. 14, 2023

(65) Prior Publication Data
US 2023/0250101 A1    Aug. 10, 2023

Related U.S. Application Data

(63) Continuation of application No. 16/982,841, filed as application No. PCT/US2019/018685 on Feb. 20, 2019, now abandoned.

(60) Provisional application No. 62/660,756, filed on Apr. 20, 2018, provisional application No. 62/660,772, filed on Apr. 20, 2018, provisional application No. 62/633,552, filed on Feb. 21, 2018, provisional application No. 62/633,557, filed on Feb. 21, 2018.

(51) Int. Cl.
*C07D 487/04*   (2006.01)
*A61P 31/04*   (2006.01)

(52) U.S. Cl.
CPC ............ *C07D 487/04* (2013.01); *A61P 31/04* (2018.01)

(58) Field of Classification Search
CPC .................................................. C07D 487/04
USPC ......................................................... 544/280
See application file for complete search history.

(56) References Cited

U.S. PATENT DOCUMENTS

| | | |
|---|---|---|
| 2012/0220566 A1 | 8/2012 | Duffy et al. |
| 2014/0163049 A1 | 6/2014 | Duffy et al. |
| 2016/0214988 A1 | 7/2016 | Kanyo et al. |
| 2018/0065966 A1 | 3/2018 | Bhattacharjee et al. |

FOREIGN PATENT DOCUMENTS

| | | |
|---|---|---|
| WO | 2012173689 A2 | 12/2012 |
| WO | 2015035426 A1 | 3/2015 |
| WO | 2016145417 A1 | 9/2016 |
| WO | 2018236692 A1 | 12/2018 |

OTHER PUBLICATIONS

Jordan, V. C. Nature Reviews: Drug Discovery, 2, 2003, 205.*
Dorwald, F. Zaragoza. Side Reactions in Organic Synthesis: A Guide to Successful Synthesis Design, Weinheim: Wiley-VCH Verlag GmbH & Co. KGaA, 2005, Preface.*
Franceschi, 2006, Structure-based drug design meets the ribosome, Biochem Biopharm 71:1016-1025.
Pubmed Compound Summary for CID 122428169, 'Sahyyjywxxdxsi-Dopyihrpsa-N', U.S. National Library of Medicine, Dec. 8, 2016, p. 1-8; p2 (https://pubchem.ncbi.nlm.nih.gov/compound/122428169).

* cited by examiner

*Primary Examiner* — Douglas M Willis
(74) *Attorney, Agent, or Firm* — Thomas C. Meyers; Sullivan & Worcester LLP

(57) ABSTRACT

The present disclosure relates generally to the field of antimicrobial compounds and to methods of making and using them. These compounds are useful for treating, preventing, reducing the risk of, and delaying the onset of microbial infections in humans and animals.

In some embodiments, the present disclosure provides a compound of Formula (A):

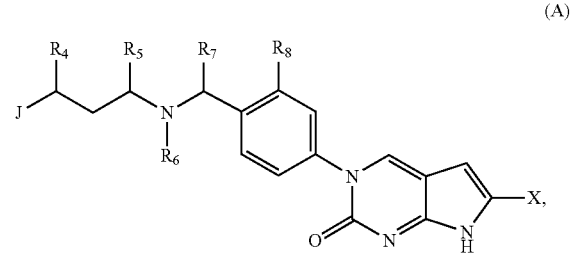

or a tautomer thereof or a pharmaceutically acceptable salt of the compound or tautomer.

18 Claims, No Drawings

SUBSTITUTED PYRROLO[2,3-D]PYRIMIDINES AS ANTIMICROBIALS

TECHNICAL FIELD

This invention relates to antimicrobial compounds, and more particularly to pyrrolo[2,3-d]pyrimidin-2-ones useful for treating, preventing and reducing risk of microbial infections.

BACKGROUND

Since the discovery of penicillin in the 1920s and streptomycin in the 1940s, many new compounds have been discovered or specifically designed for use as antibiotic agents. It was once thought that infectious diseases could be completely controlled or eradicated with the use of such therapeutic agents. However, such views have been challenged because strains of cells or microorganisms resistant to currently effective therapeutic agents continue to evolve. Almost every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed. Resistant bacteria can cause serious and even fatal results for infected patients. See, e.g., Lowry, F. D. "Antimicrobial Resistance: The Example of *Staphylococcus aureus,*" *J. Clin. Invest.*, vol. 111, no. 9, pp. 1265-1273 (2003); and Gold, H. S. and Moellering, R. C., Jr., "Antimicrobial-Drug Resistance," *N. Engl. J Med.*, vol. 335, pp. 1445-53 (1996).

The discovery and development of new antibacterial agents have been for decades a major focus of many pharmaceutical companies. Nonetheless, in more recent years there has been an exodus from this area of research and drug development resulting in very few new antibiotics entering the market. This lack of new antibiotics is particularly disturbing, especially at a time when bacterial resistance to current therapies is increasing both in the hospital and community settings.

One approach to developing new antimicrobial compounds is to design modulators, for example, inhibitors, of bacterial ribosome function. By modulating or inhibiting bacterial ribosome function, antimicrobial compounds could interfere with essential processes such as RNA translation and protein synthesis, thereby providing an antimicrobial effect. In fact, some antibiotic compounds such as erythromycin, clindamycin, and linezolid are known to bind to the ribosome.

SUMMARY

The present disclosure relates generally to the field of antimicrobial compounds and to methods of making and using them. These compounds and tautomers thereof are useful for treating, preventing, reducing the risk of, or delaying the onset of microbial infections in humans and animals. The present disclosure also provides pharmaceutically acceptable salts of these compounds and tautomers.

In some embodiments, the present application provides a compound of Formula (A):

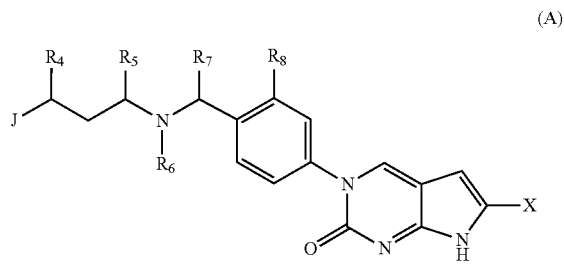

(A)

or a tautomer thereof or a pharmaceutically acceptable salt of the compound or tautomer, wherein:

J is selected from

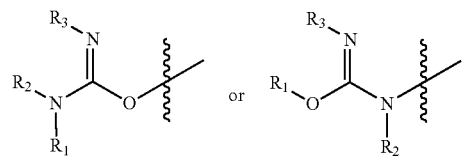

X is selected from a 5- or 6-membered heterocyclyl ring and phenyl, wherein each of the 5- or 6-membered heterocyclyl ring and phenyl is optionally substituted with one or more $R^X$;
$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-3}$ alkyl;
$R_5$ is selected from H and $C_{1-6}$ alkyl;
$R_6$ is selected from H, $C_{1-6}$ alkyl, $C_{2-6}$ alkenyl, and $C_{3-6}$ cycloalkyl, wherein the $C_{1-6}$ alkyl is optionally substituted with one or more substituents selected from the group consisting of halogen, $OR^a$, $SR^a$, $—C(O)OR^a$, $—SC(NH)NH_2$, $C_{3-6}$ cycloalkyl, and 3-6 membered heterocyclyl;
$R_7$ is selected from H and $C_{1-6}$ alkyl;
or $R_6$ and $R_7$ together with the carbon and nitrogen atoms to which they are attached form a ring having one of the formulas:

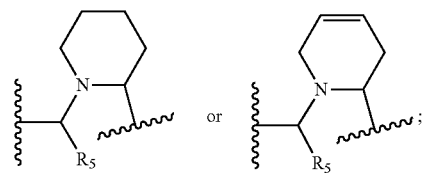

wherein the ring is optionally substituted on a ring carbon atom with $C_{1-6}$ alkyl, wherein the $C_{1-6}$ alkyl is optionally substituted with one or more OH;
or $R_5$ and $R_7$ together with the carbon atoms to which they are attached and the nitrogen atom connecting the two carbon atoms form a ring having one of the formulas:

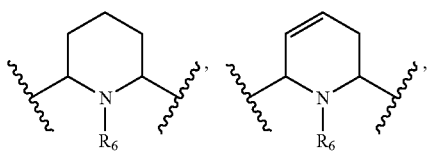

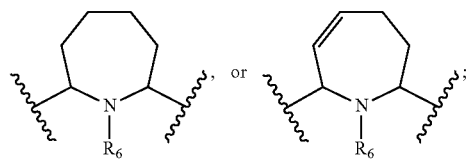

$R_8$ is selected from H and halogen;

each $R^X$ is independently selected from halogen, $C_{1-6}$ alkyl, $C_{1-4}$ haloalkyl, $OR^c$, $N(R^c)_2$, —$C(O)OR^c$, —$C(O)R^c$, $C_{3-6}$ cycloalkyl, and aryl, wherein the $C_{1-6}$ alkyl is optionally substituted with one or more $R^b$;

or two adjacent $R^X$ come together with the atoms to which they are attached to form a 5- or 6-membered ring;

each $R^a$ is independently selected from H and $C_{1-6}$ alkyl;

each $R^b$ is independently selected from $C_{2-6}$ alkenyl, $OR^c$, $N(R^c)_2$, —$C(O)OR^c$, $C_{3-6}$ cycloalkyl, $OC(NH)NH_2$, and aryl;

each $R^c$ is independently selected from H, $C_{1-6}$ alkyl, aryl, —$C(O)$aryl, and —$(CH_2)$aryl, wherein the $C_{1-6}$ alkyl and the aryl are each optionally substituted with one or more $R^d$; and each $R^d$ is independently selected from $C_{1-3}$ alkyl, OH, $O(C_{1-3}$ alkyl), $NO_2$, $NH_2$, $NH(C_{1-3}$ alkyl), and $N(C_{1-3}$ alkyl)$_2$.

Also provided herein is a compound of Formula (I):

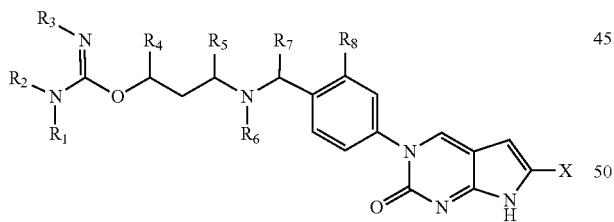

(I)

or a tautomer thereof or a pharmaceutically acceptable salt of the compound or tautomer, wherein:

X is selected from a 5- or 6-membered heterocyclyl ring and phenyl, wherein each of the 5- or 6-membered heterocyclyl ring and phenyl is optionally substituted with one or more $R^X$;

$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-6}$ alkyl;
$R_5$ is selected from H and $C_{1-6}$ alkyl;

$R_6$ is selected from H, $C_{1-6}$ alkyl, $C_{2-6}$ alkenyl, and $C_{3-6}$ cycloalkyl, wherein the $C_{1-6}$ alkyl is optionally substituted with one or more substituents selected from the group consisting of halogen, $OR^a$, $SR^a$, —$C(O)OR^a$, —$SC(NH)NH_2$, $C_{3-6}$ cycloalkyl, and 3-6 membered heterocyclyl;

$R_7$ is selected from H and $C_{1-6}$ alkyl;

or $R_6$ and $R_7$ together with the carbon and nitrogen atoms to which they are attached form a ring having one of the formulas:

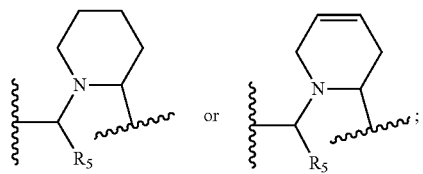

wherein the ring is optionally substituted on a ring carbon atom with $C_{1-6}$ alkyl, wherein the $C_{1-6}$ alkyl is optionally substituted with one or more OH;

or $R_5$ and $R_7$ together with the carbon atoms to which they are attached and the nitrogen atom connecting the two carbon atoms form a ring having one of the formulas:

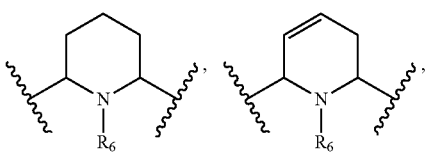

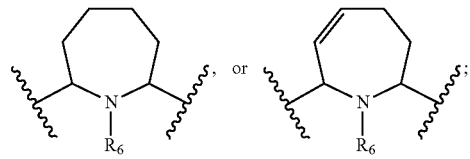

$R_8$ is selected from H and halogen;

each $R^X$ is independently selected from halogen, $C_{1-6}$ alkyl, $C_{1-4}$ haloalkyl, $OR^c$, $N(R^c)_2$, —$C(O)OR^c$, —$C(O)R^c$, $C_{3-6}$ cycloalkyl, and aryl, wherein the $C_{1-6}$ alkyl is optionally substituted with one or more $R^b$;

or two adjacent $R^X$ come together with the atoms to which they are attached to form a 5- or 6-membered ring;

each $R^a$ is independently selected from H and $C_{1-6}$ alkyl;

each $R^b$ is independently selected from $C_{2-6}$ alkenyl, $OR^c$, $N(R^c)_2$, —$C(O)OR^c$, $C_{3-6}$ cycloalkyl, $OC(NH)NH_2$, and aryl;

each $R^c$ is independently selected from H, $C_{1-6}$ alkyl, aryl, —$C(O)$aryl, and —$(CH_2)$aryl, wherein the $C_{1-6}$ alkyl and the aryl are each optionally substituted with one or more $R^d$; and each $R^d$ is independently selected from $C_{1-3}$ alkyl, OH, $O(C_{1-3}$ alkyl), $NO_2$, $NH_2$, $NH(C_{1-3}$ alkyl), and $N(C_{1-3}$ alkyl)$_2$.

Also provided herein is a compound of Formula (II):

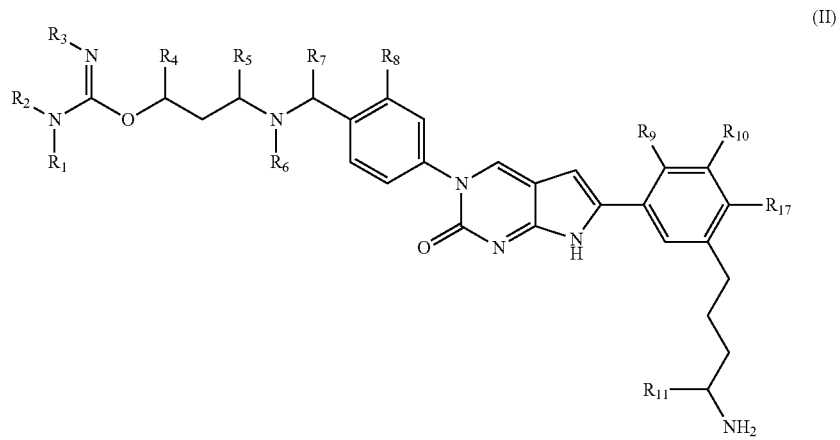

(II)

or a tautomer thereof or a pharmaceutically acceptable salt of the compound or tautomer, wherein:

$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-3}$ alkyl;
$R_5$ is selected from H and $C_{1-6}$ alkyl;
$R_6$ is selected from H, $C_{1-6}$ alkyl, and $C_{2-6}$ alkenyl, wherein the $C_{1-6}$ alkyl is optionally substituted with one or more substituents selected from the group consisting of halogen, $OR^a$, $SR^a$, —$C(O)OR^a$, —$SC(NH)NH_2$, $C_{3-6}$ cycloalkyl, or $C_{3-6}$ heterocyclyl;
$R_7$ is selected from H and $C_{1-6}$ alkyl;
or $R_6$ and $R_7$ together with the carbon and nitrogen atoms to which they are attached form a ring having one of the formulas:

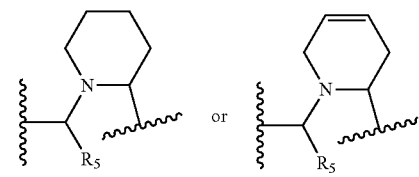

wherein the ring is optionally substituted on a ring carbon atom with $C_{1-6}$ alkyl, wherein the $C_{1-6}$ alkyl is optionally substituted with one or more OH;

or $R_5$ and $R_7$ together with the carbon atoms to which they are attached and the nitrogen atom connecting the two carbon atoms form a ring having one of the formulas:

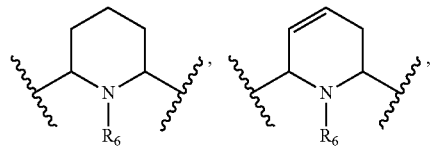

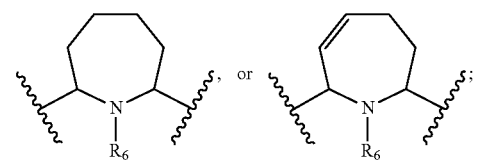

$R_8$ is selected from H and halogen;
$R_9$ is selected from H and halogen;
$R_{10}$ is selected from H, halogen, $C_{1-4}$ alkyl, $C_{1-4}$ haloalkyl, and $C_{3-6}$ cycloalkyl;
$R_{11}$ is selected from $C_{1-3}$ alkyl, $C_{2-4}$ alkenyl, and $C_{3-6}$ cycloalkyl, wherein the $C_{1-3}$ alkyl is optionally substituted with one or more $R^b$;
$R_{17}$ is selected from H, halogen, and $C_{1-6}$ alkyl;
each $R^a$ is independently selected from H and $C_{1-6}$ alkyl;
each $R^b$ is independently selected from $OR^c$, —$C(O)OR^c$, and —(O)aryl, wherein the aryl is optionally substituted with one or more $R^d$;
each $R^c$ is independently selected from hydrogen, $C_{1-3}$ alkyl, OH, $O(C_{1-3}$ alkyl$)$, $NO_2$, —$C(O)$aryl, and aryl; and
each $R^d$ is $C_{1-3}$ alkyl.

Also provided herein is a compound of Formula (III):

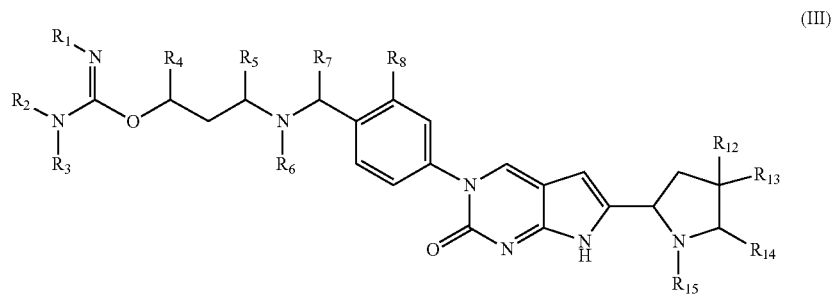

(III)

or a tautomer thereof or a pharmaceutically acceptable salt of the compound or tautomer, wherein:
$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-3}$ alkyl;
$R_5$ is selected from H and $C_{1-6}$ alkyl;
$R_6$ is selected from H, $C_{1-6}$ alkyl, and $C_{2-6}$ alkenyl, wherein the $C_{1-6}$ alkyl is optionally substituted with one or more substituents selected from the group consisting of halogen, $OR^a$, $SR^a$, —C(O)$OR^a$, and —SC(NH)$NH_2$;
$R_7$ is selected from H and $C_{1-6}$ alkyl;
or $R_6$ and $R_7$ together with the carbon and nitrogen atoms to which they are attached form a ring having one of the formulas:

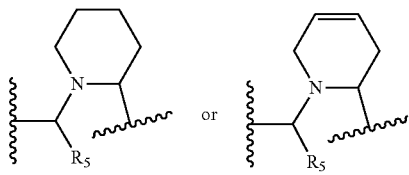

wherein the ring is optionally substituted on a carbon atom with $C_{1-6}$ alkyl, wherein the $C_{1-6}$ alkyl is optionally substituted with one or more OH;
or $R_5$ and $R_7$ together with the carbon atoms to which they are attached and the nitrogen atom connecting the two carbon atoms form a ring having one of the formulas:

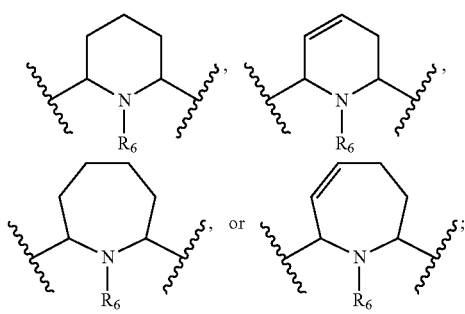

$R_8$ is selected from H and halogen;
$R_{12}$ is selected from H, halogen, and $C_{1-6}$ alkyl;
$R_{13}$ is selected from H, halogen, $C_{1-6}$ alkyl, $OR^c$, $N(R^c)_2$, wherein $C_{1-6}$ alkyl is optionally substituted with one or more of $OR^c$ and aryl;
$R_{14}$ is selected from H and aryl;
or $R_{13}$ and $R_{14}$ together with the carbon atoms to which they are attached form a 5- or 6-membered cycloalkyl ring;
$R_{15}$ is selected from H, $C_{1-6}$ alkyl, wherein the $C_{1-6}$ alkyl is optionally substituted with one or more $R^b$;
each $R^a$ is independently selected from H and $C_{1-6}$ alkyl;
each $R^b$ is independently selected from $C_{2-6}$ alkenyl, $OR^c$, $N(R')_2$, —C(O)$OR^c$, $C_{3-6}$ cycloalkyl, and aryl;
each $R^c$ is independently selected from hydrogen, $C_{1-6}$ alkyl, aryl, and —(CH$_2$)aryl, wherein the $C_{1-6}$ alkyl and the aryl are each optionally substituted with one or more $R^d$; and
each $R^d$ is independently selected from OH, O($C_{1-3}$ alkyl), $NH_2$, NH($C_{1-3}$ alkyl), and N($C_{1-3}$ alkyl)$_2$.

In some embodiments provided herein is a pharmaceutical composition comprising a compound of Formula (I), Formula (II), or Formula (III), or a tautomer thereof or a pharmaceutically acceptable salt of the compound or tautomer, and a pharmaceutically acceptable carrier.

In some embodiments provided herein is a method of treating a microbial infection comprising administering to a subject in need thereof an effective amount of a compound of Formula (I), Formula (II), or Formula (III), or a tautomer thereof or a pharmaceutically acceptable salt of the compound or tautomer, or a pharmaceutically acceptable composition as provided herein.

In some embodiments provided herein is a method of preventing a microbial infection comprising administering to a subject in need thereof an effective amount of a compound of Formula (I), Formula (II), or Formula (III), or a tautomer thereof or a pharmaceutically acceptable salt of the compound or tautomer, or a pharmaceutically acceptable composition as provided herein.

In some embodiments provided herein is a method of reducing the risk of a microbial infection comprising administering to a subject in need thereof an effective amount of a compound of Formula (I), Formula (II), or Formula (III), or a tautomer thereof or a pharmaceutically acceptable salt of the compound or tautomer, or a pharmaceutically acceptable composition as provided herein.

In some embodiments provided herein is a method of delaying the onset of a microbial infection comprising administering to a subject in need thereof an effective amount of a compound of Formula (I), Formula (II), or Formula (III), or a tautomer thereof or a pharmaceutically acceptable salt of the compound or tautomer, or a pharmaceutically acceptable composition as provided herein.

In some embodiments provided herein is a method of treating a microbial infection comprising administering to a subject in need thereof an effective amount of a compound of Formula (I), Formula (II), or Formula (III), or a tautomer thereof or a pharmaceutically acceptable salt of the compound or tautomer, or a pharmaceutically acceptable composition as provided herein.

In some embodiments provided herein is a use of a compound of Formula (I), Formula (II), or Formula (III), or a tautomer thereof or a pharmaceutically acceptable salt of the compound or tautomer, in the manufacture of a medicament for treating, preventing, or reducing a microbial infection in a subject.

In some embodiments provided herein is a compound of Formula (I), Formula (II), or Formula (III), or a tautomer thereof or a pharmaceutically acceptable salt of the compound or tautomer, for use in treating, preventing, or reducing a microbial infection in a subject.

In addition, the disclosure provides methods of synthesizing the foregoing compounds and tautomers thereof, and pharmaceutically acceptable salts of the compounds and tautomers. Following synthesis, an effective amount of one or more of the compounds or tautomers thereof, or pharmaceutically acceptable salts of the compounds or tautomers can be formulated with a pharmaceutically acceptable carrier for administration to a human or animal for use as antimicrobial agents, particularly as antibacterial agents. In certain embodiments, the compounds of the present disclosure are useful for treating, preventing, reducing the risk of, or delaying the onset of microbial infections or for the manufacture of a medicament for treating, preventing, reducing the risk of, or delaying the onset of microbial infections.

Accordingly, the compounds or tautomers thereof, or pharmaceutically acceptable salts of the compounds or tautomers or their formulations can be administered, for example, via oral, parenteral, intravenous, otic, ophthalmic, nasal, or topical routes, to provide an effective amount of the compound or tautomer thereof, or pharmaceutically acceptable salt of the compound or tautomer to the human or animal.

The foregoing and other aspects and embodiments of the disclosure can be more fully understood by reference to the following detailed description and claims.

DETAILED DESCRIPTION

The present disclosure utilizes a structure based drug design approach for discovering and developing new antimicrobial agents. This approach starts with a high resolution X-ray crystal of a ribosome to design new classes of antimicrobial compounds having specific chemical structures, ribosome binding characteristics, and antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

Based on this structure based drug design approach, the present disclosure describes new chemical classes of antimicrobial compounds useful for treating bacterial infections in humans and animals. Without being limited by theories, these compounds are believed to inhibit bacterial ribosome function by binding to the ribosome. By taking advantage of these ribosome binding sites, the antimicrobial compounds of the present disclosure can provide better activity, especially against resistant strains of bacteria, than currently available antibiotic compounds.

The present disclosure therefore fills an important ongoing need for new antimicrobial agents, particularly for antimicrobial agents, having activity against resistant pathogenic bacterial organisms.

The present disclosure also provides a method of treating, preventing, reducing the risk of, or delaying the onset of a microbial infection in a subject that includes administering to the subject a therapeutically effective amount of any one of the compounds of the present disclosure, or a tautomer thereof or a pharmaceutically acceptable salt of the compound or tautomer, or a pharmaceutically acceptable composition of the present disclosure, where the infection is caused by or involves one or more microorganisms which are capable of being used as biological weapons, or the infection is caused by or involves one or more microorganisms which are extremely-drug resistant Gram-positive or Gram-negative pathogens.

Also provided is a kit that includes a container, any one of the compounds of the present disclosure, or a tautomer thereof or a pharmaceutically acceptable salt of the compound or tautomer, or a pharmaceutically acceptable composition of the present disclosure, and instructions for use in treating, preventing, reducing the risk of, or delaying the onset of a microbial infection. In some embodiments, the microbial infection is caused by or involves one or more microorganisms which are capable of being used as biological weapons.

Also provided is the use of a compound of any one of the compounds of the present disclosure, or a tautomer thereof or a pharmaceutically acceptable salt of the compound or tautomer, in the manufacture of a medicament for treating, preventing, or reducing a microbial infection in a subject. In some embodiments, the infection is caused by or involves one or more microorganisms which are capable of being used as biological weapons, or the infection is caused by or involves one or more microorganisms which are extremely-drug resistant Gram-positive or Gram-negative pathogens.

In some embodiments, provided is a compound of the present disclosure, or a tautomer thereof or a pharmaceutically acceptable salt of the compound or tautomer, for use in treating, preventing, or reducing a microbial infection in a subject. In some embodiments, the infection is caused by or involves one or more microorganisms which are capable of being used as biological weapons, or the infection is caused by or involves one or more microorganisms which are extremely-drug resistant Gram-positive or Gram-negative pathogens.

The present disclosure provides a family of compounds or tautomers thereof, that can be used as antimicrobial agents, more particularly as antibacterial agents.

The present disclosure also includes pharmaceutically acceptable salts of the compounds and tautomers.

The compounds or tautomers thereof, or pharmaceutically acceptable salts of the compounds or tautomers disclosed herein can have asymmetric centers. Compounds or tautomers thereof, or pharmaceutically acceptable salts of the compounds or tautomers of the present disclosure containing an asymmetrically substituted atom can be isolated in optically active or racemic forms. Optically active forms of compounds can be prepared, for example, by resolution of racemic forms or by synthesis from optically active starting materials. Many geometric isomers of olefins, C=N double bonds, and the like can also be present in the compounds or tautomers thereof, or pharmaceutically acceptable salts of the compounds or tautomers disclosed herein, and all such stable isomers are contemplated in the present disclosure. Cis and trans geometric isomers of the compounds or tautomers thereof, or pharmaceutically acceptable salts of the compounds or tautomers of the present disclosure are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds or tautomers thereof, or pharmaceutically acceptable salts of the compounds or tautomers of the present disclosure and intermediates made herein are considered to be part of the present disclosure. All tautomers of shown or described compounds are also considered to be part of the present disclosure. Furthermore, the disclosure also includes metabolites of the compounds disclosed herein.

The disclosure also provides for isotopically-labeled compounds or tautomers thereof, or pharmaceutically acceptable salts of the compounds or tautomers, which are identical to those recited in formulae of the disclosure, but for the replacement of one or more atoms by an atom having an atomic mass or mass number different from the atomic mass or mass number most commonly found in nature. Examples of isotopes that can be incorporated into compounds or tautomers thereof, or pharmaceutically acceptable salts of the compounds or tautomers of the disclosure include isotopes of hydrogen, carbon, nitrogen, and fluorine, such as $^3$H, $^{11}$C, $^{14}$C, and $^{18}$F.

The compounds of the present disclosure or tautomers thereof, or pharmaceutically acceptable salts of the compounds or tautomers that contain the aforementioned isotopes and/or isotopes of other atoms are within the scope of the present disclosure. Isotopically-labeled compounds or tautomers thereof, or pharmaceutically acceptable salts of the compounds or tautomers of the present disclosure, for example, those into which radioactive isotopes such as $^3$H and $^{14}$C are incorporated, are useful in drug and/or substrate tissue distribution assays. Tritium, i.e., $^3$H, and carbon-14, i.e., $^{14}$C, isotopes are particularly preferred due to their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, i.e., increased in vivo half-life or reduced dosage requirements and, hence, may be preferred in some circumstances. Isotopically labeled compounds or tautomers thereof, or pharmaceutically acceptable salts of the compounds or tautomers having a formula of the disclosed herein can generally be prepared as described in the procedures, Schemes and/or in the Examples disclosed herein, by substituting a non-isotopically labeled reagent with a readily available isotopically labeled reagent. In one embodiment, the compounds or tautomers thereof, or pharmaceutically acceptable salts of the compounds or tautomers disclosed herein are not isotopically labeled.

When any variable (e.g., R) occurs more than one time in any constituent or formulae of the disclosed herein, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valence.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein compounds of the present disclosure, or tautomers thereof, or pharmaceutically acceptable salts of the compounds or tautomers thereof, contain nitrogen atoms, these, where appropriate, can be converted to N-oxides by treatment with an oxidizing agent (e.g., meta-chloroperoxybenzoic acid (mCPBA) and/or hydrogen peroxides). Thus, shown and claimed nitrogen atoms are considered to cover both the shown nitrogen and its N-oxide (N→O) derivative, as appropriate. In some embodiments, the present disclosure relates to N-oxides of the compounds or tautomers thereof, or pharmaceutically acceptable salts of the compounds or tautomers disclosed herein.

One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions*," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation, i.e., the peptidyl-transferase reaction of protein synthesis, and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

1. Definitions

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. A compound with one chiral center has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however, as a result of recent advances in chromatography techniques, it has been possible to separate mixtures of two atropic isomers in select cases.

Some compounds of the present disclosure can exist in a tautomeric form which is also intended to be encompassed within the scope of the present disclosure. "Tautomers" refers to compounds whose structures differ markedly in the arrangement of atoms, but which exist in easy and rapid equilibrium. It is to be understood that compounds of the present disclosure may be depicted as different tautomers. It should also be understood that when compounds have tautomeric forms, all tautomeric forms are intended to be within the scope of the disclosure, and the naming of the compounds does not exclude any tautomeric form.

The compounds and pharmaceutically acceptable salts of the present disclosure can exist in one or more tautomeric forms, including the enol and imine form and the keto and enamine form, and geometric isomers and mixtures thereof. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein.

A tautomer is one of two or more structural isomers that exist in equilibrium and are readily converted from one isomeric form to another. This reaction results in the formal migration of a hydrogen atom accompanied by a shift of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism, a simultaneous shift of electrons and a hydrogen atom occurs. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

Common tautomeric pairs include: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples below are included for illustrative purposes, and the present disclosure is not limited to the examples:

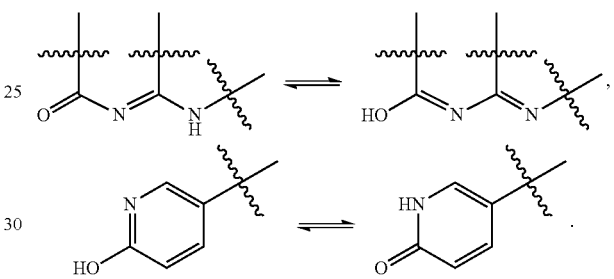

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto or oxo (i.e., =O), then 2 hydrogens on the atom are replaced. Ring double bonds, as used herein, are double bonds that are formed between two adjacent ring atoms (e.g., C=C, C=N, N=N, etc.).

As used herein, "alkyl" is intended to include both branched and straight-chain saturated aliphatic hydrocarbon groups having the specified number of carbon atoms. For example, $C_{1-4}$ is intended to include $C_1$, $C_2$, $C_3$, and $C_4$. $C_{1-6}$ alkyl is intended to include $C_1$, $C_2$, $C_3$, $C_4$, $C_5$, and $C_6$ alkyl groups and $C_{1-8}$ is intended to include $C_1$, $C_2$, $C_3$, $C_4$, $C_5$, $C_6$, $C_7$, and $C_8$. Some examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example, $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$.

As used herein, "alkylene" is intended to include moieties which are diradicals, i.e., having two points of attachment. A non-limiting example of such alkylene moiety that is a diradical is —CH$_2$CH$_2$—, i.e., a $C_2$ alkyl group that is covalently bonded via each terminal carbon atom to the remainder of the molecule. The alkylene diradicals are also known as "alkylenyl" radicals. Alkylene groups can be saturated or unsaturated (e.g., containing —CH=CH— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms). Some examples of alkylene groups include, but not limited to, methylene, ethylene, n-propylene, iso-propylene, n-butylene, iso-butylene, sec-butylene, tert-butylene, n-pentylene, iso-pentylene, sec-pentylene and neo-pentylene.

As used herein, "cycloalkyl" is intended to include saturated or unsaturated nonaromatic ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups. Cycloalkyls may include multiple spiro- or fused rings.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

As used herein, "amine" or "amino" refers to unsubstituted —NH₂ unless otherwise specified.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with one or more halogen (for example —$C_vF_w$ $H_{2v-w+1}$ wherein v=1 to 3 and w=1 to (2v+1)). Examples of haloalkyl include, but are not limited to, trifluoromethyl, trichloromethyl, pentafluoroethyl, and pentachloroethyl.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

As used herein, "alkoxyl" or "alkoxy" refers to an alkyl group as defined above with the indicated number of carbon atoms attached through an oxygen bridge. $C_1$_6 alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$. alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "Aryl" includes groups with aromaticity, including "conjugated," or multicyclic systems with at least one aromatic ring and do not contain any heteroatom in the ring structure. Aryl may be monocyclic or polycyclic (e.g., having 2, 3 or 4 fused rings). The term "$C_{n-m}$ aryl" refers to an aryl group having from n to m ring carbon atoms.

In some embodiments, aryl groups have from 6 to 10 carbon atoms. In some embodiments, the aryl group is phenyl or naphtyl.

As used herein, the term "aromatic heterocycle", "aromatic heterocyclic" or "heteroaryl" ring is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzooxadiazoly, carbazolyl, 4aH-carbazolyl, carbolinyl, cinnolinyl, furazanyl, imidazolyl, imidazolonyl, 1H-indazolyl, indolizinyl, indolyl, 3H-indolyl, isobenzofuranyl, isochromanyl, isoindazolyl, isoindolyl, isoquinolinyl, isothiazolyl, isoxazolyl, methyl-benztriazolyl, methylfuranyl, methylimidazolyl, methylthiazolyl, naphthyridinyl, oxadiazolyl, 1,2,3-oxadiazolyl, 1,2, 4-oxadiazolyl, 1,2,5-oxadiazolyl, 1,3,4-oxadiazolyl, oxazolyl, phenanthridinyl, phenanthrolinyl, phenazinyl, phenothiazinyl, phenoxathinyl, phenoxazinyl, phthalazinyl, pteridinyl, purinyl, pyrazinyl, pyrazolyl, pyridazinyl, pyridooxazolyl, pyridoimidazolyl, pyridothiazolyl, pyridinyl, pyridinonyl, pyridyl, pyrimidinyl, 2H-pyrrolyl, pyrrolyl, quinazolinyl, quinolinyl, 4H-quinolizinyl, quinoxalinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, triazolopyrimidinyl, 1,2,3-triazolyl, 1,2,4-triazolyl, 1,2,5-triazolyl, and 1,3,4-triazolyl.

The term "hydroxyalkyl" means an alkyl group as defined above, where the alkyl group is substituted with one or more OH groups. Examples of hydroxyalkyl groups include HO—CH₂—, HO—CH₂—CH₂— and CH₃—CH(OH)—.

The term "cyano" as used herein means a substituent having a carbon atom joined to a nitrogen atom by a triple bond, i.e., C≡N.

As used herein, "oxo" is means a "=O" group.

As used herein, the phrase "pharmaceutically acceptable" refers to those compounds or tautomers thereof, or salts thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making of the acid or base salts thereof of the parent compound or a tautomer thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound, or a tautomer thereof, formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present disclosure can be synthesized from the parent compound or a tautomer thereof, that contains a basic or acidic moiety by conventional chemical methods. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., USA, p. 1445 (1990).

As used herein, "stable compound" and "stable structure" are meant to indicate a compound that is sufficiently robust to survive isolation to a useful degree of purity from a reaction mixture, and formulation into an efficacious therapeutic agent.

As used herein, the term "treating" means to provide a therapeutic intervention to cure or ameliorate an infection. In some embodiments, "treating" refers to administering a compound or pharmaceutical composition as provided herein for therapeutic purposes.

The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

As used herein, the term "preventing", as used herein means, to completely or almost completely stop an infection from occurring, for example when the patient or subject is predisposed to an infection or at risk of contracting an infection. Preventing can also include inhibiting, i.e., arresting the development, of an infection.

As used herein, the term "reducing the risk of", as used herein, means to lower the likelihood or probability of an infection occurring, for example when the patient or subject is predisposed to an infection or at risk of contracting an infection.

As used herein, "unsaturated" refers to compounds having at least one degree of unsaturation (e.g., at least one multiple bond) and includes partially and fully unsaturated compounds.

As used herein, the term "effective amount" refers to an amount of a compound or a tautomer thereof, or a pharmaceutically acceptable salt of the compound or tautomer (including combinations of compounds and/or tautomers thereof, and/or pharmaceutically acceptable salts of the compound or tautomer) of the present disclosure that is effective when administered alone or in combination as an antimicrobial agent. For example, an effective amount refers to an amount of the compound or tautomer thereof, or a pharmaceutically acceptable salt of the compound or tautomer that is present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity.

The term "prophylactically effective amount" means an amount of a compound or a tautomer of the compound, or a pharmaceutically acceptable salt of the compound or tautomer (including combinations of compounds and/or tautomers thereof, and/or pharmaceutically acceptable salts thereof), of the present disclosure that is effective prophylactically when administered alone or in combination as an antimicrobial agent. For example, a prophylactically effective amount refers to an amount of the compound or tautomer thereof, or a pharmaceutically acceptable salt of the compound or tautomer that is present in a composition, a formulation, or on a medical device given to a recipient patient or subject sufficient to prevent or reduce the risk of an infection due to a surgical procedure or an invasive medical procedure.

As used herein, the term ESBL is extended spectrum beta-lactamase. The term KPC is *Klebsiella pneumoniae* carbapenemase.

As used herein, the term acute bacterial skin and skin structure infection (ABSSSI) encompasses complicated skin and skin structure infections (cSSSI) and complication skin and soft tissue infections (cSSTI), which have been used interchangeably. The terms uncomplicated skin and skin structure infections (uCSSSI) and uncomplicated skin and soft tissue infections (uCSSTI) have been used interchangeably.

As used herein, the term "spp." is the abbreviation for species.

As used herein, the term "formulae of the disclosure" or "formulae disclosed herein" includes one or more of the Formulae: (I), (A), (Ia), (Ia-1), (Ia-2), (Ib), (Ic), (I-A), (Ib-2), (Ic-2), (Id-2) and (Id).

As used herein, the term "compound of the disclosure" or "compound disclosed herein" includes one or more compounds of the formulae of the disclosure or a compound explicitly disclosed herein.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present disclosure also consist essentially of, or consist of, the recited components, and that the processes of the present disclosure also consist essentially of, or consist of, the recited processing steps. Further, it should be understood that the order of steps or order for performing certain actions are immaterial so long as the invention remains operable. Moreover, two or more steps or actions can be conducted simultaneously.

2. Compounds of the Disclosure

In some embodiments, the present application provides a compound of Formula (A):

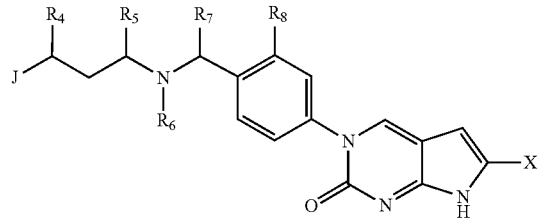

(A)

or a tautomer thereof or a pharmaceutically acceptable salt of the compound or tautomer, wherein:
J is selected from

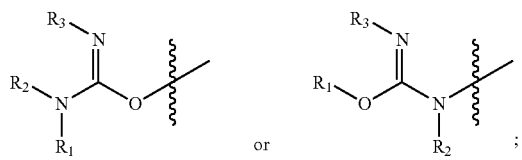

X is selected from a 5- or 6-membered heterocyclyl ring and phenyl, wherein each of the 5- or 6-membered heterocyclyl ring and phenyl is optionally substituted with one or more $R^X$;
$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-3}$ alkyl;
$R_5$ is selected from H and $C_{1-6}$ alkyl;
$R_6$ is selected from H, $C_{1-6}$ alkyl, $C_{2-6}$ alkenyl, and $C_{3-6}$ cycloalkyl, wherein the $C_{1-6}$ alkyl is optionally substituted with one or more substituents selected from the group consisting of halogen, $OR^a$, $SR^a$, —C(O)$OR^a$, —SC(NH)$NH_2$, $C_{3-6}$ cycloalkyl, and 3-6 membered heterocyclyl;
$R_7$ is selected from H and $C_{1-6}$ alkyl;
or $R_6$ and $R_7$ together with the carbon and nitrogen atoms to which they are attached form a ring having one of the formulas:

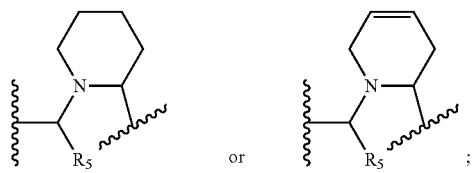

wherein the ring is optionally substituted on a ring carbon atom with $C_{1-6}$ alkyl, wherein the $C_{1-6}$ alkyl is optionally substituted with one or more OH;

or $R_5$ and $R_7$ together with the carbon atoms to which they are attached and the nitrogen atom connecting the two carbon atoms form a ring having one of the formulas:

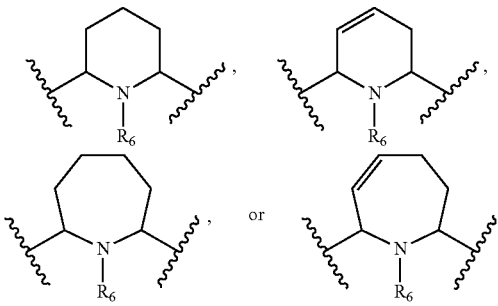

$R_8$ is selected from H and halogen;
each $R^X$ is independently selected from halogen, $C_{1-6}$ alkyl, $C_{1-4}$ haloalkyl, $OR^c$, $N(R^c)_2$, —C(O)$OR^c$, —C(O)$R^c$, $C_{3-6}$ cycloalkyl, and aryl, wherein the $C_{1-6}$ alkyl is optionally substituted with one or more $R^b$;
or two adjacent $R^X$ come together with the atoms to which they are attached to form a 5- or 6-membered ring;
each $R^a$ is independently selected from H and $C_{1-6}$ alkyl;
each $R^b$ is independently selected from $C_{2-6}$ alkenyl, $OR^c$, $N(R')_2$, —C(O)$OR^c$, $C_{3-6}$ cycloalkyl, OC(NH)$NH_2$, and aryl;
each R is independently selected from H, $C_{1-6}$ alkyl, aryl, —C(O)aryl, and —(CH$_2$)aryl, wherein the $C_{1-6}$ alkyl and the aryl are each optionally substituted with one or more $R^d$; and
each $R^d$ is independently selected from $C_{1-3}$ alkyl, OH, O($C_{1-3}$ alkyl), $NO_2$, $NH_2$, NH($C_{1-3}$ alkyl), and N($C_{1-3}$ alkyl)$_2$.
In some embodiments, the present application provides a compound of Formula

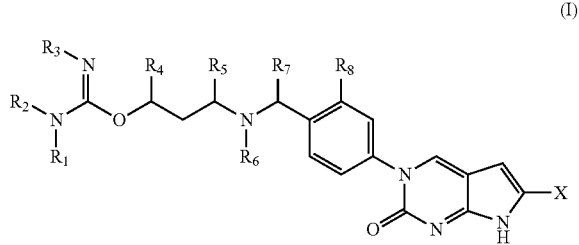

(I)

or a tautomer thereof or a pharmaceutically acceptable salt of the compound or tautomer, wherein:
X is selected from a 5- or 6-membered heterocyclyl ring and phenyl, wherein each of the 5- or 6-membered heterocyclyl ring and phenyl is optionally substituted with one or more $R^X$;
$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-3}$ alkyl;
$R_5$ is selected from H and $C_{1-6}$ alkyl;
$R_6$ is selected from H, $C_{1-6}$ alkyl, $C_{2-6}$ alkenyl, and $C_{3-6}$ cycloalkyl, wherein the $C_{1-6}$ alkyl is optionally substituted with one or more substituents selected from the group consisting of halogen, $OR^a$, $SR^a$, $-C(O)OR^a$, $-SC(NH)NH_2$, $C_{3-6}$ cycloalkyl, and 3-6 membered heterocyclyl;

$R_7$ is selected from H and $C_{1-6}$ alkyl;

or $R_6$ and $R_7$ together with the carbon and nitrogen atoms to which they are attached form a ring having one of the formulas:

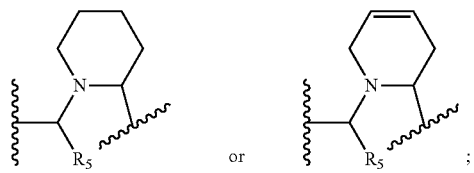

wherein the ring is optionally substituted on a ring carbon atom with $C_{1-6}$ alkyl, wherein the $C_{1-6}$ alkyl is optionally substituted with one or more OH;

or $R_5$ and $R_7$ together with the carbon atoms to which they are attached and the nitrogen atom connecting the two carbon atoms form a ring having one of the formulas:

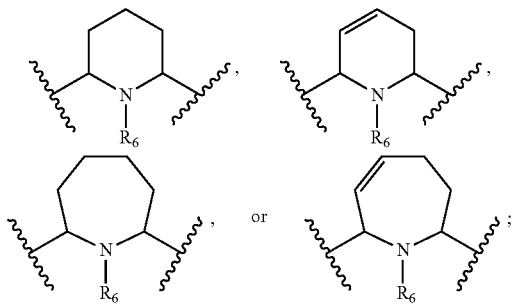

$R_8$ is selected from H and halogen;

each $R^x$ is independently selected from halogen, $C_{1-6}$ alkyl, $C_{1-4}$ haloalkyl, $OR^e$, $N(R^e)_2$, $-C(O)OR^e$, $-C(O)R^e$, $C_{3-6}$ cycloalkyl, and aryl, wherein the $C_{1-6}$ alkyl is optionally substituted with one or more $R^b$;

or two adjacent $R^x$ come together with the atoms to which they are attached to form a 5- or 6-membered ring;

each $R^a$ is independently selected from H and $C_{1-6}$ alkyl;

each $R^b$ is independently selected from $C_{2-6}$ alkenyl, $OR^e$, $N(R^e)_2$, $-C(O)OR^e$, $C_{3-6}$ cycloalkyl, $OC(NH)NH_2$, and aryl;

each $R^e$ is independently selected from H, $C_{1-6}$ alkyl, aryl, $-C(O)aryl$, and $-(CH_2)aryl$, wherein the $C_{1-6}$ alkyl and the aryl are each optionally substituted with one or more $R^d$; and each $R^d$ is independently selected from $C_{1-3}$ alkyl, OH, $O(C_{1-3}$ alkyl), $NO_2$, $NH_2$, $NH(C_{1-3}$ alkyl), and $N(C_{1-3}$ alkyl)$_2$.

In some embodiments of Formula (I), each of $R_1$, $R_2$, and $R_3$ is H. In some embodiments, two of $R_1$, $R_2$, and $R_3$ are H, and the other is $C_{1-3}$ alkyl. For example, two of $R_1$, $R_2$, and $R_3$ are H, and the other is methyl. In some embodiments, one of $R_1$, $R_2$, and $R_3$ is H, and the other two are $C_{1-3}$ alkyl. For example, one of $R_1$, $R_2$, and $R_3$ is H, and the other two are methyl. In some embodiments, $R_1$ is H; and $R_2$ and $R_3$ together with the nitrogen atoms to which they are attached and the carbon atom connecting the two nitrogen atoms form a 5- or 6-membered ring. For example, $R_1$ is H; and $R_2$ and $R_3$ together with the nitrogen atoms to which they are attached and the carbon atom connecting the two nitrogen atoms form an imidazoline.

In some embodiments of Formula (I), $R_4$ is H. In some embodiments, $R_4$ is $C_{1-3}$ alkyl.

In some embodiments of Formula (I), one of $R_5$ and $R_7$ is H and the other is $C_{1-6}$ alkyl. For example, $R_5$ is H and $R_7$ is $C_{1-6}$ alkyl. In some embodiments, $R_5$ and $R_7$ together with the carbon atoms to which they are attached and the nitrogen atom connecting the two carbon atoms form

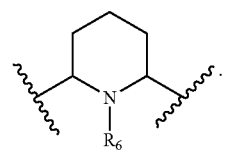

In some embodiments, $R_5$ and $R_7$ together with the carbon atoms to which they are attached and the nitrogen atom connecting the two carbon atoms form

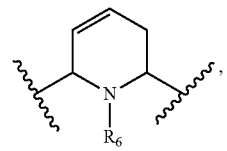

wherein the ring is optionally substituted on a carbon atom of the ring with $C_{1-6}$ alkyl, wherein the $C_{1-6}$ alkyl is optionally substituted with one or more OH. In some embodiments, $R_5$ and $R_7$ together with the carbon atoms to which they are attached and the nitrogen atom connecting the two carbon atoms form

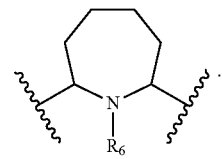

In some embodiments, $R_5$ and $R_7$ together with the carbon atoms to which they are attached and the nitrogen atom connecting the two carbon atoms form

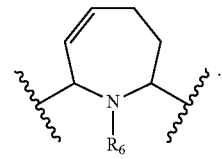

In some embodiments of Formula (I), $R_5$ and $R_7$ together with the carbon atoms to which they are attached and the nitrogen atom connecting the two carbon atoms form a ring having one of the formulas:

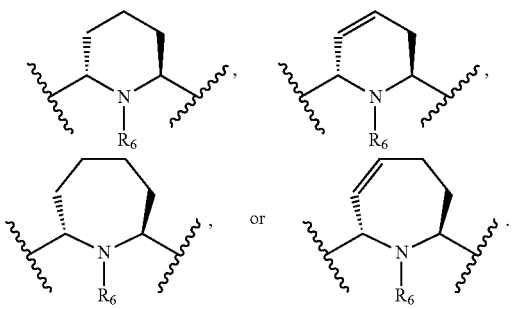

In some embodiments, $R_5$ and $R_7$ together with the carbon atoms to which they are attached and the nitrogen atom connecting the two carbon atoms form

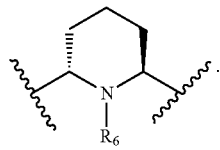

In some embodiments, $R_5$ and $R_7$ together with the carbon atoms to which they are attached and the nitrogen atom connecting the two carbon atoms form

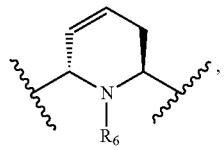

wherein the ring is optionally substituted on a carbon atom of the ring with $C_{1-6}$ alkyl, wherein the $C_{1-6}$ alkyl is optionally substituted with one or more OH. In some embodiments, $R_5$ and $R_7$ together with the carbon atoms to which they are attached and the nitrogen atom connecting the two carbon atoms form

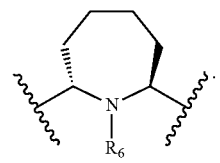

In some embodiments, $R_5$ and $R_7$ together with the carbon atoms to which they are attached and the nitrogen atom connecting the two carbon atoms form

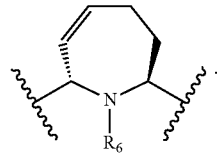

In some embodiments of Formula (I), $R_6$ and $R_7$ together with the carbon and nitrogen atoms to which they are attached form a ring of formula

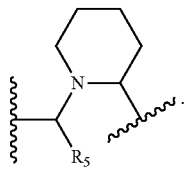

In some embodiments, $R_6$ and R, together with the carbon and nitrogen atoms to which they are attached form a ring of formula

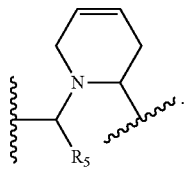

In some embodiments of Formula (I), $R_6$ and $R_7$ together with the carbon and nitrogen atoms to which they are attached form a ring having one of the formulas:

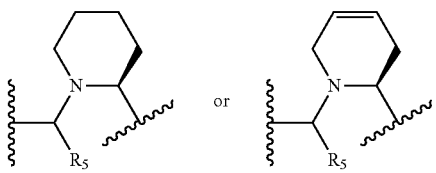

wherein the ring is optionally substituted on a ring carbon atom with $C_{1-6}$ alkyl, wherein the $C_{1-6}$ alkyl is optionally substituted with one or more OH. In some embodiments of Formula (I), $R_6$ and $R_7$ together with the carbon and nitrogen atoms to which they are attached form a ring of formula

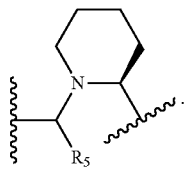

In some embodiments, $R_6$ and $R_7$ together with the carbon and nitrogen atoms to which they are attached form a ring of formula

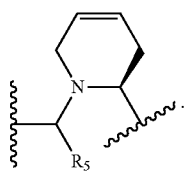

In some embodiments of Formula (I), $R_6$ is selected from H and $C_{1-6}$ alkyl optionally substituted with one or more substituents selected from the group consisting of halogen and OR$^a$. In some embodiments, R$_6$ is H. In some embodiments, R$_6$ is C$_{1-6}$ alkyl optionally substituted with one or more substituents selected from the group consisting of halogen and OR$^a$. For example, R$_6$ is C$_{1-6}$ alkyl optionally substituted with one or more substituents selected from the group consisting of fluorine, bromine and OH.

In some embodiments of Formula (I), R$_6$ is C$_{1-6}$ alkyl optionally substituted with OR$^a$. In some embodiments, R$^a$ is H. In some embodiments, R$^a$ is C$_{1-6}$ alkyl.

In some embodiments of Formula (I), R$_6$ is C$_{1-6}$ alkyl substituted with —SC(NH)NH$_2$. In some embodiments, R$_6$ is C$_{1-6}$ alkyl optionally substituted with halogen. For example, R$_6$ is C$_{1-6}$ alkyl optionally substituted with fluoro.

In some embodiments of Formula (I), X is selected from a 5-membered heterocyclyl ring and phenyl, wherein each of the 5-membered heterocyclyl ring and phenyl is optionally substituted with one or more R$^X$. For example, X is a 5-membered heterocyclyl ring optionally substituted with one or more R$^X$. In some embodiments, X is a pyrrolidinyl optionally substituted with one or more R$^X$. In some embodiments, X is a 2- or 3-pyrrolidinyl optionally substituted with one or more R$^X$. In some embodiments, X is phenyl optionally substituted with one or more R$^X$. For example, X is phenyl optionally substituted with three R$^X$.

In some embodiments of Formula (I), R$^X$ is independently selected from halogen, C$_{1-6}$ alkyl, OR$^c$, N(R$^c$)$_2$, —C(O)OR$^c$, —C(O)R, C$_{3-6}$ cycloalkyl, and aryl, wherein the C$_{1-6}$ alkyl is optionally substituted with one or more R$^b$. In some embodiments, R$^X$ is independently selected from halogen and C$_{1-6}$ alkyl optionally substituted with one or more R$^b$. In some such embodiments, R$^b$ is selected from C$_{2-6}$ alkenyl, OR$^c$, N(R$^c$)$_2$, and C$_{3-6}$ cycloalkyl. For example, R$^b$ is selected from C$_{2-6}$ alkenyl, OR$^c$, NH$_2$, and cyclopropyl. In some such embodiments, R$^c$ is selected from H and C$_{1-6}$ alkyl. In some embodiments, R$^b$ is selected from vinyl, OH, and NH$_2$. In some embodiments, two adjacent R$^X$ come together with the atoms to which they are attached to form a 5- or 6-membered ring.

In some embodiments of Formula (I), the compound is a compound of Formula (IA):

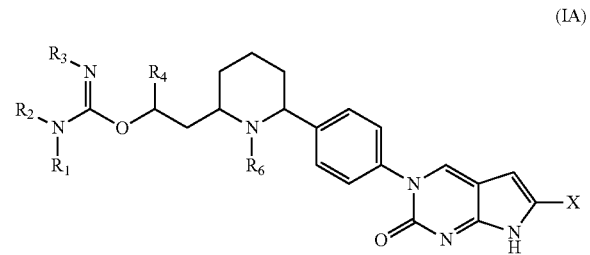

(IA)

or a tautomer thereof or a pharmaceutically acceptable salt of the compound or tautomer, wherein:
X is selected from a 5- or 6-membered heterocyclyl ring and phenyl, wherein each of the 5- or 6-membered heterocyclyl ring and phenyl is optionally substituted with one or more R$^X$;
R$_1$ is selected from H and C$_{1-3}$ alkyl;
R$_2$ is selected from H and C$_{1-3}$ alkyl;
R$_3$ is selected from H and C$_{1-3}$ alkyl;
R$_4$ is selected from H and C$_{1-3}$ alkyl;
R$_6$ is selected from H, C$_{1-6}$ alkyl, and C$_{2-6}$ alkenyl, wherein the C$_{1-6}$ alkyl is optionally substituted with one or more substituents selected from the group consisting of halogen, OR$^a$, SR$^a$, —C(O)OR$^a$, —SC(NH)NH$_2$, C$_{3-6}$ cycloalkyl, or C$_{3-6}$ heterocyclyl; each R$^X$ is independently selected from halogen, C$_{1-6}$ alkyl, C$_{1-4}$ haloalkyl, OR$^c$, N(R$^c$)$_2$, —C(O)OR$^c$, —C(O)R$^c$, C$_{3-6}$ cycloalkyl, and aryl, wherein the C$_{1-6}$ alkyl is optionally substituted with one or more R$^b$;
or two adjacent R$^X$ come together with the atoms to which they are attached to form a 5- or 6-membered ring;
each R$^a$ is independently selected from H and C$_{1-6}$ alkyl;
each R is independently selected from C$_{2-6}$ alkenyl, OR$^c$, N(R$^c$)$_2$, —C(O)OR$^c$, C$_{3-6}$ cycloalkyl, and aryl;
each R$^c$ is independently selected from H, C$_{1-6}$ alkyl, aryl, —C(O)aryl, and —(CH$_2$)aryl, wherein the C$_{1-6}$ alkyl and the aryl are each optionally substituted with one or more R$^d$; and
each R$^d$ is independently selected from C$_{1-3}$ alkyl, OH, O(C$_{1-3}$ alkyl), NO$_2$, NH$_2$, NH(C$_{1-3}$ alkyl), and N(C$_{1-3}$ alkyl)$_2$.

In some embodiments of Formula (IA), R$_1$, R$_2$, and R$_3$ is H. In some embodiments, two of R$_1$, R$_2$, and R$_3$ are H, and the other is C$_{1-3}$ alkyl. For example, two of R$_1$, R$_2$, and R$_3$ are H, and the other is methyl. In some embodiments, one of R$_1$, R$_2$, and R$_3$ is H, and the other two are C$_{1-3}$ alkyl. For example, one of R$_1$, R$_2$, and R$_3$ is H, and the other two are methyl. In some embodiments, R$_2$ and R$_3$ together with the nitrogen atoms to which they are attached and the carbon atom connecting the two nitrogen atoms form a 5- or 6-membered ring. For example, R$_2$ and R$_3$ together with the nitrogen atoms to which they are attached and the carbon atom connecting the two nitrogen atoms form an imidazoline.

In some embodiments of Formula (IA), R$_4$ is H. In some embodiments, R$_4$ is C$_{1-3}$ alkyl.

In some embodiments of Formula (IA), R$_6$ is selected from H and C$_{1-6}$ alkyl optionally substituted with one or more substituents selected from the group consisting of halogen and OR$^a$. In some embodiments, R$_6$ is H. In some embodiments, R$_6$ is C$_{1-6}$ alkyl optionally substituted with one or more substituents selected from the group consisting of halogen and OR$^a$. For example, R$_6$ is C$_{1-6}$ alkyl optionally substituted with OR$^a$. In some such embodiments, R is H. In other such embodiments, R$^a$ is C$_{1-6}$ alkyl. In some embodiments, R$_6$ is C$_{1-6}$ alkyl substituted with —SC(NH)NH$_2$. In some embodiments, R$_6$ is C$_{1-6}$ alkyl optionally substituted with halogen. For example, R$_6$ is C$_{1-6}$ alkyl optionally substituted with fluoro.

In some embodiments of Formula (IA), X is selected from a 5-membered heterocyclyl ring and phenyl, wherein each of the 5-membered heterocyclyl ring and phenyl is optionally substituted with one or more R$^X$. In some embodiments, X is a 5-membered heterocyclyl ring optionally substituted with one or more R$^X$. For example, X is a pyrrolidinyl optionally substituted with one or more R$^X$. In some embodiments, X is a 2- or 3-pyrrolidinyl optionally substituted with one or more R$^X$. In some embodiments, X is phenyl optionally substituted with one or more R$^X$. For example, X is phenyl optionally substituted with three R$^X$.

In some embodiments of Formula (IA), R$^X$ is independently selected from halogen, C$_{1-6}$ alkyl, OR$^c$, N(R$^c$)$_2$, —C(O)OR$^c$, —C(O)R$^c$, C$_{3-6}$ cycloalkyl, and aryl, wherein the C$_{1-6}$ alkyl is optionally substituted with one or more R$^b$. For example, R$^X$ is independently selected from halogen and C$_{1-6}$ alkyl optionally substituted with one or more R$^b$. In some such embodiments, R$^b$ is selected from C$_{2-6}$ alkenyl, OR$^c$, N(R$^c$)$_2$, and C$_{3-6}$ cycloalkyl. For example, R$^b$ is selected from C$_{2-6}$ alkenyl, OR$^c$, NH$_2$, and cyclopropyl. In some such embodiments, R is selected from H and $C_{1-6}$ alkyl. In some embodiments, $R^b$ is selected from vinyl, OH, and $NH_2$.

In some embodiments of Formula (IA), two adjacent $R^X$ come together with the atoms to which they are attached to form a 5- or 6-membered ring.

In some embodiments of Formula (I), the compound is a compound of Formula

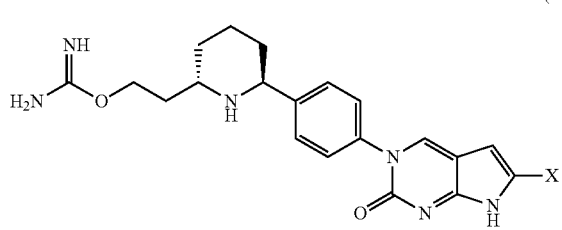

(IB)

or a tautomer thereof or a pharmaceutically acceptable salt of the compound or tautomer, wherein:

X is selected from a 5- or 6-membered heterocyclyl ring and phenyl, wherein each of the 5- or 6-membered heterocyclyl ring and phenyl is optionally substituted with one or more $R^X$;

each $R^X$ is independently selected from halogen, $C_{1-6}$ alkyl, $C_{1-4}$ haloalkyl, $OR^c$, $N(R^c)_2$, —$C(O)OR^c$, —$C(O)R^c$, $C_{3-6}$ cycloalkyl, and aryl, wherein the $C_{1-6}$ alkyl is optionally substituted with one or more $R^b$;

or two adjacent $R^X$ come together with the atoms to which they are attached to form a 5- or 6-membered ring;

each $R^b$ is independently selected from $C_{2-6}$ alkenyl, $OR^c$, $N(R^c)_2$, —$C(O)OR^c$, $C_{3-6}$ cycloalkyl, and aryl;

each $R^c$ is independently selected from H, $C_{1-6}$ alkyl, aryl, —C(O)aryl, and —($CH_2$)aryl, wherein the $C_{1-6}$ alkyl and the aryl are each optionally substituted with one or more $R^d$; and each $R^d$ is independently selected from $C_{1-3}$ alkyl, OH, O($C_{1-3}$ alkyl), $NO_2$, $NH_2$, NH($C_{1-3}$ alkyl), and N($C_{1-3}$ alkyl)$_2$.

In some embodiments of Formula (IB), X is selected from a 5-membered heterocyclyl ring and phenyl, wherein each of the 5-membered heterocyclyl ring and phenyl is optionally substituted with one or more $R^X$. In some embodiments, X is a 5-membered heterocyclyl ring optionally substituted with one or more $R^X$. For example, X is a pyrrolidinyl optionally substituted with one or more $R^X$. In some embodiments, X is a 2- or 3-pyrrolidinyl optionally substituted with one or more $R^X$. In some embodiments, X is phenyl optionally substituted with one or more $R^X$. For example, X is phenyl optionally substituted with three $R^X$. In some embodiments, $R^X$ is independently selected from halogen, $C_{1-6}$ alkyl, $OR^c$, $N(R^c)_2$, —$C(O)OR^c$, —$C(O)R$, $C_{3-6}$ cycloalkyl, and aryl, wherein the $C_{1-6}$ alkyl is optionally substituted with one or more $R^b$. In some embodiments, $R^X$ is independently selected from halogen and $C_{1-6}$ alkyl optionally substituted with one or more $R^b$. In some embodiments, $R^b$ is selected from $C_{2-6}$ alkenyl, $OR^c$, $N(R^0)_2$, and $C_{3-6}$ cycloalkyl. For example, $R^b$ is selected from $C_{2-6}$ alkenyl, $OR^c$, $NH_2$, and cyclopropyl. In some such embodiments, R is selected from H and $C_{1-6}$ alkyl. In some embodiments, $R^b$ is selected from vinyl, OH, and $NH_2$.

In some embodiments of Formula (IB), two adjacent $R^X$ come together with the atoms to which they are attached to form a 5- or 6-membered ring.

Also provided herein is a compound of Formula (II):

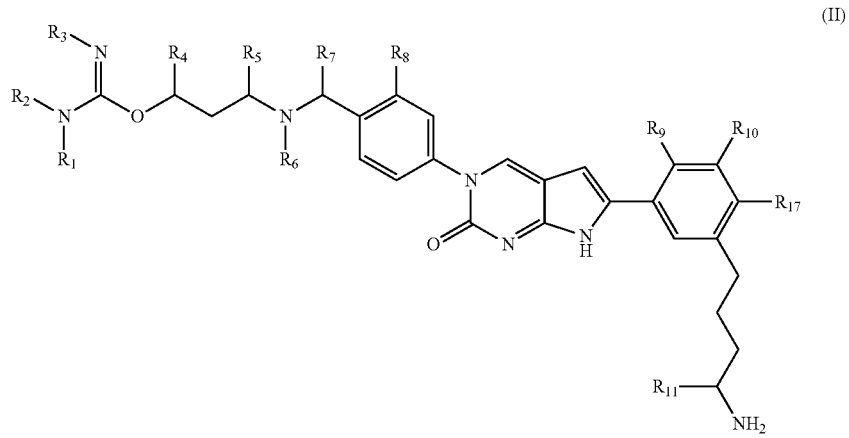

(II)

or a tautomer thereof or a pharmaceutically acceptable salt of the compound or tautomer, wherein:
$R_1$ is selected from H and $C_{1-3}$ alkyl;
$R_2$ is selected from H and $C_{1-3}$ alkyl;
$R_3$ is selected from H and $C_{1-3}$ alkyl;
or $R_2$ and $R_3$ together with the nitrogen atoms to which they are attached and the carbon atom connecting the two nitrogen atoms form a 5- or 6-membered ring;
$R_4$ is selected from H and $C_{1-3}$ alkyl;
$R_5$ is selected from H and $C_{1-6}$ alkyl;
$R_6$ is selected from H, $C_{1-6}$ alkyl, and $C_{2-6}$ alkenyl, wherein the $C_{1-6}$ alkyl is optionally substituted with one or more substituents selected from the group consisting of halogen, $OR^a$, $SR^a$, $-C(O)OR^a$, $-SC(NH)NH_2$, $C_{3-6}$ cycloalkyl, or $C_{3-6}$ heterocyclyl;
$R_7$ is selected from H and $C_{1-6}$ alkyl;
or $R_6$ and $R_7$ together with the carbon and nitrogen atoms to which they are attached form a ring having one of the formulas:

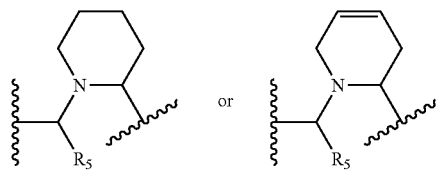

wherein the ring is optionally substituted on a ring carbon atom with $C_{1-6}$ alkyl, wherein the $C_{1-6}$ alkyl is optionally substituted with one or more OH;
or $R_5$ and $R_7$ together with the carbon atoms to which they are attached and the nitrogen atom connecting the two carbon atoms form a ring having one of the formulas:

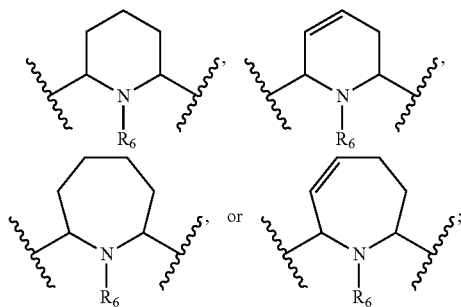

$R_8$ is selected from H and halogen;
$R_9$ is selected from H and halogen;
$R_{10}$ is selected from H, halogen, $C_{1-4}$ alkyl, $C_{1-4}$ haloalkyl, and $C_{3-6}$ cycloalkyl;
$R_{11}$ is selected from $C_{1-3}$ alkyl, $C_{2-4}$ alkenyl, and $C_{3-6}$ cycloalkyl, wherein the $C_{1-3}$ alkyl is optionally substituted with one or more $R^b$.
$R_{17}$ is selected from H, halogen, and $C_{1-6}$ alkyl;
each $R^a$ is independently selected from H and $C_{1-6}$ alkyl;
each $R^b$ is independently selected from $OR^c$, $-C(O)OR^c$, and $-(O)aryl$, wherein the aryl is optionally substituted with one or more $R^d$;
each $R^c$ is independently selected from hydrogen, $C_{1-3}$ alkyl, OH, $O(C_{1-3}$ alkyl), $NO_2$, $-C(O)aryl$, and aryl; and
each $R^d$ is $C_{1-3}$ alkyl.

In some embodiments of Formula (II), each of $R_1$, $R_2$, and $R_3$ is H. In some embodiments, two of $R_1$, $R_2$, and $R_3$ are H, and the other is $C_{1-3}$ alkyl. For example, two of $R_1$, $R_2$, and $R_3$ are H, and the other is methyl. In some embodiments, one of $R_1$, $R_2$, and $R_3$ is H, and the other two are $C_{1-3}$ alkyl. For example, one of $R_1$, $R_2$, and $R_3$ is H, and the other two are methyl. In some embodiments, $R_2$ and $R_3$ together with the nitrogen atoms to which they are attached and the carbon atom connecting the two nitrogen atoms form a 5- or 6-membered ring. For example, $R_2$ and $R_3$ together with the nitrogen atoms to which they are attached and the carbon atom connecting the two nitrogen atoms form an imidazoline.

In some embodiments of Formula (II), $R_4$ is H. In some embodiments, $R_4$ is $C_{1-3}$ alkyl.

In some embodiments of Formula (II), one of $R_5$ and R, is H and the other is $C_{1-6}$ alkyl. For example, $R_5$ is H and $R_7$ is $C_{1-6}$ alkyl. In some embodiments, $R_5$ and $R_7$ together with the carbon atoms to which they are attached and the nitrogen atom connecting the two carbon atoms form

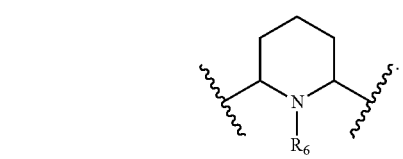

In some embodiments, $R_5$ and $R_7$ together with the carbon atoms to which they are attached and the nitrogen atom connecting the two carbon atoms form

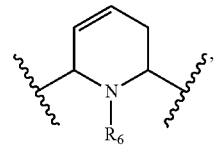

wherein the ring is optionally substituted on a carbon atom of the ring with $C_{1-6}$ alkyl, wherein the $C_{1-6}$ alkyl is optionally substituted with one or more OH. In some embodiments, $R_5$ and $R_7$ together with the carbon atoms to which they are attached and the nitrogen atom connecting the two carbon atoms form

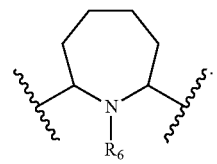

In some embodiments, $R_5$ and $R_7$ together with the carbon atoms to which they are attached and the nitrogen atom connecting the two carbon atoms form

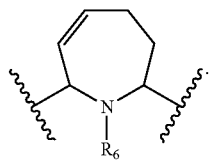

In some embodiments of Formula (II), $R_5$ and R, together with the carbon atoms to which they are attached and the nitrogen atom connecting the two carbon atoms form a ring having one of the formulas:

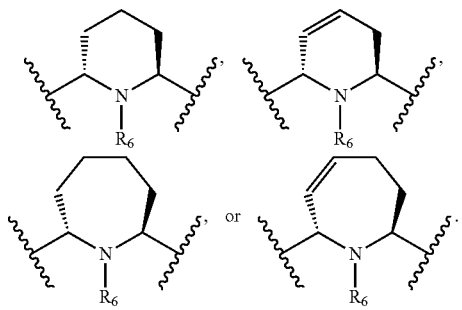

In some embodiments, $R_5$ and $R_7$ together with the carbon atoms to which they are attached and the nitrogen atom connecting the two carbon atoms form

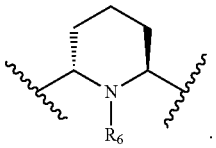

In some embodiments, $R_5$ and $R_7$ together with the carbon atoms to which they are attached and the nitrogen atom connecting the two carbon atoms form

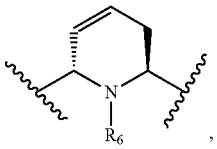

wherein the ring is optionally substituted on a carbon atom of the ring with $C_{1-6}$ alkyl, wherein the $C_{1-6}$ alkyl is optionally substituted with one or more OH. In some embodiments, $R_5$ and $R_7$ together with the carbon atoms to which they are attached and the nitrogen atom connecting the two carbon atoms form

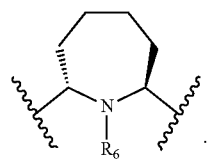

In some embodiments, $R_5$ and $R_7$ together with the carbon atoms to which they are attached and the nitrogen atom connecting the two carbon atoms form

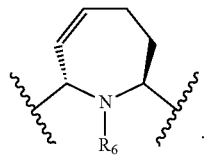

In some embodiments of Formula (II), $R_6$ and $R_7$ together with the carbon and nitrogen atoms to which they are attached form a ring of formula

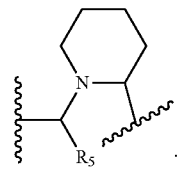

In some embodiments, $R_6$ and $R_7$ together with the carbon and nitrogen atoms to which they are attached form a ring of formula

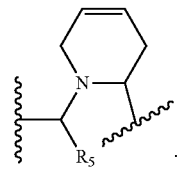

In some embodiments of Formula (II), $R_6$ and $R_7$ together with the carbon and nitrogen atoms to which they are attached form a ring having one of the formulas:

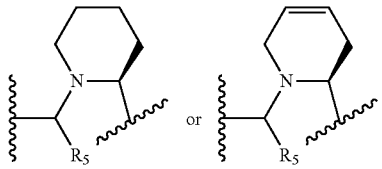

wherein the ring is optionally substituted on a ring carbon atom with $C_{1-6}$ alkyl, wherein the $C_{1-6}$ alkyl is optionally substituted with one or more OH. In some embodiments, $R_6$ and $R_7$ together with the carbon and nitrogen atoms to which they are attached form a ring of formula

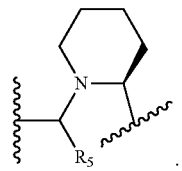

In some embodiments, $R_6$ and $R_7$ together with the carbon and nitrogen atoms to which they are attached form a ring of formula

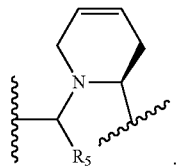

In some embodiments of Formula (II), $R_6$ is selected from H and $C_{1-6}$ alkyl optionally substituted with one or more substituents selected from the group consisting of halogen and $OR^a$. In some embodiments, $R_6$ is H. In some embodiments, $R_6$ is $C_{1-6}$ alkyl optionally substituted with one or more substituents selected from the group consisting of halogen and $OR^a$. In some embodiments, $R_6$ is $C_{1-6}$ alkyl optionally substituted with $OR^a$. In some such embodiments, $R^a$ is H. In other such embodiments, $R^a$ is $C_{1-6}$ alkyl. In some embodiments, $R_6$ is $C_{1-6}$ alkyl substituted with —SC(NH)NH$_2$. In some embodiments, $R_6$ is $C_{1-6}$ alkyl optionally substituted with halogen. For example, $R_6$ is $C_{1-6}$ alkyl optionally substituted with fluoro.

In some embodiments of Formula (II), $R_8$ is H. In some embodiments, $R_8$ is halogen. For example, $R_8$ is F.

In some embodiments of Formula (II), one of $R_9$ and $R_{10}$ is halogen and the other is H. In some embodiments, each of $R_9$ and $R_{10}$ is halogen. For example, $R_9$ is fluoro and $R_{10}$ is chloro. In some embodiments, $R_9$ is H and $R_{10}$ is $C_{1-4}$ alkyl. In some embodiments, $R_9$ is halogen and $R_{10}$ is $C_{1-4}$ alkyl. For example, $R_9$ is chloro and $R_{10}$ is $C_{1-4}$ alkyl. In some embodiments, $R_9$ is fluoro and $R_{10}$ is $C_{1-4}$ alkyl. In some such embodiments, $R_{10}$ is ethyl or $R_{10}$ is isopropyl. In some embodiments, $R_9$ is H and $R_{10}$ is $C_{3-6}$ cycloalkyl. For example, $R_{10}$ is cyclopropyl or $R_{10}$ is cyclopentyl.

In some embodiments of Formula (II), $R_{11}$ is selected from $C_{1-3}$ alkyl optionally substituted with one or more $R^b$, and $C_{2-4}$ alkenyl. In some embodiments, $R_1$ is selected from $C_{1-3}$ alkyl optionally substituted with one or more $R^b$, and $C_{3-6}$ cycloalkyl. In some embodiments, $R_1$ is $C_{1-3}$ alkyl optionally substituted with one or more $R^b$. In some such embodiments, $R^b$ is $OR^c$, wherein $R^c$ is selected from H and $C_{1-3}$ alkyl. For example, $R^c$ is H. In some embodiments, $R^e$ is $C_{1-3}$ alkyl. $R^c$ is $C_{1-3}$ alkyl. $R_{11}$ is $C_{1-3}$ alkyl. For example, Rn is methyl. In some embodiments, $R_1$ is $C_{3-6}$ cycloalkyl. For example, $R_{11}$ is cyclopropyl.

In some embodiments of Formula (II), the Cahn-Ingold-Prelog configuration at the carbon atom $R_{11}$ is bonded to is (R). In some embodiments, the Cahn-Ingold-Prelog configuration at the carbon atom $R_{11}$ is bonded to is (S).

In some embodiments, $R_{17}$ is H. In some embodiments, $R_{11}$ is halogen.

In some embodiments of Formula (II), each of $R_9$ and $R_{10}$ is halogen, and $R_{11}$ is $C_{1-3}$ alkyl optionally substituted with one or more $R^b$. For example, $R_9$ is fluoro, $R_{10}$ is chloro, and $R_{11}$ is $C_{1-3}$ alkyl optionally substituted with one or more $R^b$. In some embodiments, $R_9$ is fluoro, $R_{10}$ is chloro, and $R_{11}$ is methyl. In some embodiments, $R_9$ is fluoro, $R_{10}$ is chloro, $R_{11}$ is methyl, and wherein the Cahn-Ingold-Prelog configuration at the carbon atom $R_{11}$ is bonded to is (S).

In some embodiments of Formula (II), each of $R_1$, $R_2$, and $R_3$ is H; $R_4$ is H; $R^6$ is $C_{1-6}$ alkyl optionally substituted with one or more substituents selected from the group consisting of halogen and $OR^a$; $R_9$ is fluoro, $R_{10}$ is chloro, and $R_{11}$ is methyl. In some embodiments, each of $R_1$, $R_2$, and $R_3$ is H; $R_4$ is H; $R_6$ is H or $C_{1-6}$ alkyl; $R_9$ is fluoro, $R_{10}$ is chloro, $R_{11}$ is methyl, and wherein the Cahn-Ingold-Prelog configuration at the carbon atom $R_1$ is bonded to is (S). In some embodiments, each of $R_1$, $R_2$, and $R_3$ is H; $R_4$ is H; $R_6$ and $R_7$ together with the carbon and nitrogen atoms to which they are attached form a ring of formula

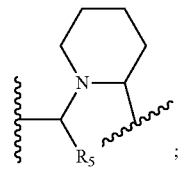

$R_9$ is fluoro; $R_{10}$ is chloro; and $R_{11}$ is methyl. In some embodiments, each of $R_1$, $R_2$, and $R_3$ is H; $R_4$ is H; $R_5$ and $R_7$ together with the carbon atoms to which they are attached and the nitrogen atom connecting the two carbon atoms form

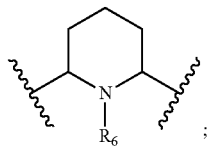

$R_6$ is H or $C_{1-6}$ alkyl; $R_9$ is fluoro, $R_{10}$ is chloro, $R_{11}$ is methyl, and wherein the Cahn-Ingold-Prelog configuration at the carbon atom $R_{11}$ is bonded to is (S).

In some embodiments of Formula (II), the compound is a compound of Formula (IIA):

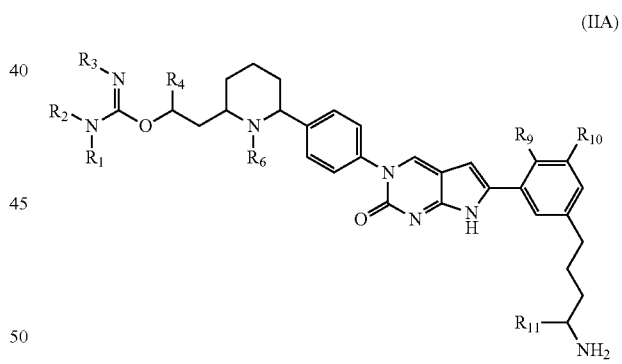

or a tautomer thereof or a pharmaceutically acceptable salt of the compound or tautomer, wherein:
$R_1$ is selected from H and $C_{1-3}$ alkyl;
$R_2$ is selected from H and $C_{1-3}$ alkyl;
$R_3$ is selected from H and $C_{1-3}$ alkyl;
$R_4$ is selected from H and $C_{1-3}$ alkyl;
$R_6$ is selected from H, $C_{1-6}$ alkyl, and $C_{2-6}$ alkenyl, wherein the $C_{1-6}$ alkyl is optionally substituted with one or more substituents selected from the group consisting of halogen and $OR^a$;
$R_9$ is selected from H and halogen;
$R_{10}$ is selected from H, halogen, $C_{1-4}$ alkyl, $C_{1-4}$ haloalkyl, and $C_{3-6}$ cycloalkyl $R_{11}$ is selected from $C_{1-3}$ alkyl, $C_{2-4}$ alkenyl, and $C_{3-6}$ cycloalkyl, wherein the $C_{1-3}$ alkyl is optionally substituted with one or more $R^b$;

each $R^a$ is independently selected from H and $C_{1-6}$ alkyl;

each $R^b$ is independently selected from $OR^c$, —$C(O)OR^c$, and —(O)aryl, wherein the aryl is optionally substituted with one or more $R^d$;

each $R^e$ is independently selected from hydrogen, $C_{1-3}$ alkyl, OH, $O(C_{1-3}$ alkyl), $NO_2$, —C(O)aryl, and aryl; and each $R^d$ is $C_{1-3}$ alkyl.

In some embodiments of Formula (IIA), each of $R_1$, $R_2$, and $R_3$ is H. In some embodiments, two of $R_1$, $R_2$, and $R_3$ are H, and the other is $C_{1-3}$ alkyl. For example, two of $R_1$, $R_2$, and $R_3$ are H, and the other is methyl. In some embodiments, one of $R_1$, $R_2$, and $R_3$ is H, and the other two are $C_{1-3}$ alkyl. For example, one of $R_1$, $R_2$, and $R_3$ is H, and the other two are methyl. In some embodiments, $R_2$ and $R_3$ together with the nitrogen atoms to which they are attached and the carbon atom connecting the two nitrogen atoms form a 5- or 6-membered ring. For example, $R_2$ and $R_3$ together with the nitrogen atoms to which they are attached and the carbon atom connecting the two nitrogen atoms form an imidazoline.

In some embodiments of Formula (IIA), $R_4$ is H.

In some embodiments of Formula (IIA), $R_6$ is selected from H and $C_{1-6}$ alkyl optionally substituted with one or more substituents selected from the group consisting of halogen and $OR^a$. In some embodiments, $R_6$ is H. In some embodiments, $R_6$ is $C_{1-6}$ alkyl optionally substituted with one or more substituents selected from the group consisting of halogen and $OR^a$. For example, $R_6$ is $C_{1-6}$ alkyl optionally substituted with $OR^a$. In some such embodiments, $R^a$ is H. In other such embodiments, $R^a$ is $C_{1-6}$ alkyl. In some embodiments, $R_6$ is $C_{1-6}$ alkyl optionally substituted with halogen. For example, $R_6$ is $C_{1-6}$ alkyl optionally substituted with fluoro.

In some embodiments of Formula (IIA), one of $R_9$ and $R_{10}$ is halogen and the other is H. In some embodiments, each of $R_9$ and $R_{10}$ is halogen. For example, $R_9$ is fluoro and $R_{10}$ is chloro. In some embodiments, $R_9$ is H and $R_{10}$ is $C_{1-4}$ alkyl. In some embodiments, $R_9$ is halogen and $R_{10}$ is $C_{1-4}$ alkyl. For example, $R_9$ is chloro and $R_{10}$ is $C_{1-4}$ alkyl. In some embodiments, $R_9$ is fluoro and $R_{10}$ is $C_{1-4}$ alkyl. For example, $R_{10}$ is ethyl or $R_{10}$ is isopropyl. In some embodiments, $R_9$ is H and $R_{10}$ is $C_{3-6}$ cycloalkyl. For example, $R_{10}$ is cyclopropyl or $R_{10}$ is cyclopentyl.

In some embodiments of Formula (IIA), $R_{11}$ is selected from $C_{1-3}$ alkyl optionally substituted with one or more $R^b$, and $C_{2-4}$ alkenyl. In some embodiments, $R_1$ is selected from $C_{1-3}$ alkyl optionally substituted with one or more $R^b$, and $C_{3-6}$ cycloalkyl. In some embodiments, $R_{11}$ is $C_{1-3}$ alkyl optionally substituted with one or more $R^b$. In some such embodiments, $R^b$ is $OR^c$, and wherein $R^c$ is selected from H and $C_{1-3}$ alkyl. For example, $R^c$ is H. In some embodiments, $R^c$ is $C_{1-3}$ alkyl. In some embodiments, $R_1$ is $C_{1-3}$ alkyl. For example, $R_1$ is methyl. In some embodiments, $R_1$ is $C_{3-6}$ cycloalkyl. For example, $R_{11}$ is cyclopropyl.

In some embodiments of Formula (IIA), the Cahn-Ingold-Prelog configuration at the carbon atom $R_{11}$ is bonded to is (R). In some embodiments, the Cahn-Ingold-Prelog configuration at the carbon atom $R_1$ is bonded to is (S).

In some embodiments of Formula (IIA), each of $R_9$ and $R_{10}$ is halogen, and $R_{11}$ is $C_{1-3}$ alkyl optionally substituted with one or more $R^b$. For example, $R_9$ is fluoro, $R_{10}$ is chloro, and $R_{11}$ is methyl. In some embodiments, $R_9$ is fluoro, $R_{10}$ is chloro, $R_{11}$ is methyl. In some embodiments, $R_9$ is fluoro, $R_{10}$ is chloro, $R_{11}$ is methyl, and wherein the Cahn-Ingold-Prelog configuration at the carbon atom $R_{11}$ is bonded to is (S).

In some embodiments of Formula (IIA), each of $R_1$, $R_2$, and $R_3$ is H; $R_4$ is H; $R_6$ is $C_{1-6}$ alkyl optionally substituted with one or more substituents selected from the group consisting of halogen and $OR^a$; $R_9$ is fluoro, $R_{10}$ is chloro, and $R_{11}$ is methyl. In some embodiments, each of $R_1$, $R_2$, and $R_3$ is H; $R_4$ is H; $R_6$ is H or $C_{1-6}$ alkyl; $R_9$ is fluoro, $R_{10}$ is chloro, $R_{11}$ is methyl, and wherein the Cahn-Ingold-Prelog configuration at the carbon atom $R_1$ is bonded to is (S).

In some embodiments of Formula (II), the compound is a compound of Formula (IIB):

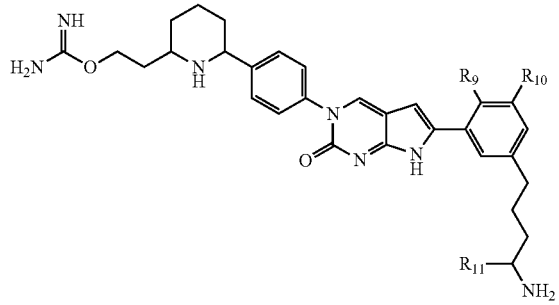

(IIB)

or a tautomer thereof or a pharmaceutically acceptable salt of the compound or tautomer, wherein:

$R_9$ is selected from H and halogen;

$R_{10}$ is selected from H, halogen, $C_{1-4}$ alkyl, $C_{1-4}$ haloalkyl, and $C_{3-6}$ cycloalkyl;

$R_{11}$ is selected from $C_{1-3}$ alkyl, $C_{2-4}$ alkenyl, and $C_{3-6}$ cycloalkyl, wherein the $C_{1-3}$ alkyl is optionally substituted with one or more $R^b$;

each $R^b$ is independently selected from $OR^c$, —$C(O)OR^c$, and —(O)aryl, wherein the aryl is optionally substituted with one or more $R^d$;

each $R^c$ is independently selected from hydrogen, $C_{1-3}$ alkyl, OH, $O(C_{1-3}$ alkyl), $NO_2$, —C(O)aryl, and aryl; and each $R^d$ is $C_{1-3}$ alkyl.

In some embodiments of Formula (IIB), one of $R_9$ and $R_{10}$ is halogen and the other is H. In some embodiments, each of $R_9$ and $R_{10}$ is halogen. For example, $R_9$ is fluoro and $R_{10}$ is chloro. In some embodiments, $R_9$ is H and $R_{10}$ is $C_{1-4}$ alkyl. In some embodiments, $R_9$ is halogen and $R_{10}$ is $C_{1-4}$ alkyl. For example, $R_9$ is chloro and $R_{10}$ is $C_{1-4}$ alkyl. In some embodiments, $R_9$ is fluoro and $R_{10}$ is $C_{1-4}$ alkyl. For example, $R_{10}$ is ethyl or $R_{10}$ is isopropyl. In some embodiments, $R_9$ is H and $R_{10}$ is $C_{3-6}$ cycloalkyl. For example, $R_{10}$ is cyclopropyl or $R_{10}$ is cyclopentyl.

In some embodiments of Formula (IIB), $R_{11}$ is selected from $C_{1-3}$ alkyl optionally substituted with one or more $R^b$, and $C_{2-4}$ alkenyl. In some embodiments, Rn is selected from $C_{1-3}$ alkyl optionally substituted with one or more $R^b$, and $C_{3-6}$ cycloalkyl. In some embodiments, $R_{11}$ is $C_{1-3}$ alkyl optionally substituted with one or more $R^b$. In some such embodiments, $R^b$ is $OR^c$, and $R^c$ is selected from H and $C_{1-3}$ alkyl. For example, $R^c$ is H. In some embodiments, $R^c$ is $C_{1-3}$ alkyl. In some embodiments, $R_1$ is $C_{1-3}$ alkyl. For example, $R_{11}$ is methyl. In some embodiments, $R_1$ is $C_{3-6}$ cycloalkyl. For example, $R_{11}$ is cyclopropyl.

In some embodiments of Formula (IIB), the Cahn-Ingold-Prelog configuration at the carbon atom $R_{11}$ is bonded to is (R). In some embodiments, the Cahn-Ingold-Prelog configuration at the carbon atom Rn is bonded to is (S).

In some embodiments of Formula (IIB), each of $R_9$ and $R_{10}$ is halogen, and $R_{11}$ is $C_{1-3}$ alkyl optionally substituted with one or more $R^b$. For example, $R_9$ is fluoro, $R_{10}$ is chloro, and $R_{11}$ is $C_{1-3}$ alkyl optionally substituted with one or more $R^b$. In some embodiments, $R_9$ is fluoro, $R_{10}$ is chloro, and $R_{11}$ is methyl. In some embodiments, $R_9$ is fluoro, $R_{10}$ is chloro, $R_{11}$ is methyl, and wherein the Cahn-Ingold-Prelog configuration at the carbon atom $R_{11}$ is bonded to is (S).

Also provided herein is a compound of Formula (III):

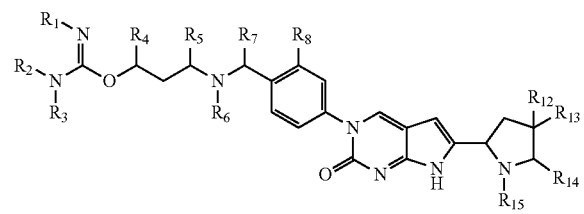

(III)

or a tautomer thereof or a pharmaceutically acceptable salt of the compound or tautomer, wherein:

$R_1$ is selected from H and $C_{1-3}$ alkyl;

$R_2$ is selected from H and $C_{1-3}$ alkyl;

$R_3$ is selected from H and $C_{1-3}$ alkyl;

or $R_2$ and $R_3$ together with the nitrogen atoms to which they are attached and the carbon atom connecting the two nitrogen atoms form a 5- or 6-membered ring;

$R_4$ is selected from H and $C_{1-3}$ alkyl;

$R^5$ is selected from H and $C_{1-6}$ alkyl;

$R_6$ is selected from H, $C_{1-6}$ alkyl, and $C_{2-6}$ alkenyl, wherein the $C_{1-6}$ alkyl is optionally substituted with one or more substituents selected from the group consisting of halogen, $OR^a$, $SR^a$, $—C(O)OR^a$, and $—SC(NH)NH_2$;

$R_7$ is selected from H and $C_{1-6}$ alkyl;

or $R_6$ and $R_7$ together with the carbon and nitrogen atoms to which they are attached form a ring having one of the formulas:

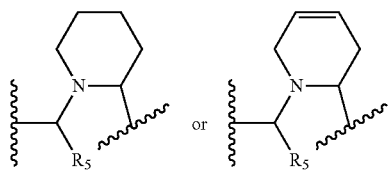

wherein the ring is optionally substituted on a carbon atom with $C_{1-6}$ alkyl, wherein the $C_{1-6}$ alkyl is optionally substituted with one or more OH;

or $R_5$ and $R_7$ together with the carbon atoms to which they are attached and the nitrogen atom connecting the two carbon atoms form a ring having one of the formulas:

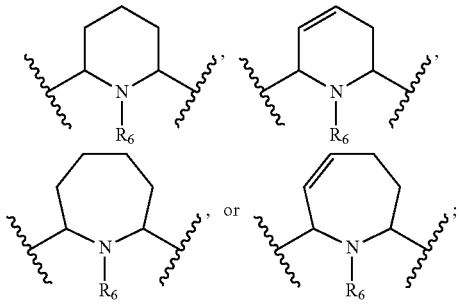

$R_8$ is selected from H and halogen;

$R_{12}$ is selected from H, halogen, and $C_{1-6}$ alkyl;

$R_{13}$ is selected from H, halogen, $C_{1-6}$ alkyl, $OR^c$, $N(R^c)_2$, wherein $C_{1-6}$ alkyl is optionally substituted with one or more of $OR^c$ and aryl;

$R_{14}$ is selected from H and aryl;

or $R_{13}$ and $R_{14}$ together with the carbon atoms to which they are attached form a 5- or 6-membered cycloalkyl ring;

$R_{15}$ is selected from H, $C_{1-6}$ alkyl, wherein the $C_{1-6}$ alkyl is optionally substituted with one or more $R^b$;

each $R^a$ is independently selected from H and $C_{1-6}$ alkyl;

each $R^b$ is independently selected from $C_{2-6}$ alkenyl, $OR^c$, $N(R^c)_2$, $—C(O)OR^c$, $C_{3-6}$ cycloalkyl, and aryl;

each $R^c$ is independently selected from hydrogen, $C_{1-6}$ alkyl, aryl, and $—(CH_2)$aryl, wherein the $C_{1-6}$ alkyl and the aryl are each optionally substituted with one or more $R^d$; and each $R^d$ is independently selected from OH, $O(C_{1-3}$ alkyl), $NH_2$, $NH(C_{1-3}$ alkyl), and $N(C_{1-3}$ alkyl$)_2$.

In some embodiments of Formula (III), each of $R_1$, $R_2$, and $R_3$ is H. In some embodiments, two of $R_1$, $R_2$, and $R_3$ are H, and the other is $C_{1-3}$ alkyl. For example, two of $R_1$, $R_2$, and $R_3$ are H, and the other is methyl. In some embodiments, one of $R_1$, $R_2$, and $R_3$ is H, and the other two are $C_{1-3}$ alkyl. For example, one of $R_1$, $R_2$, and $R_3$ is H, and the other two are methyl.

In some embodiments of Formula (III), $R_4$ is H.

In some embodiments, $R_5$ and $R_7$ together with the carbon atoms to which they are attached and the nitrogen atom connecting the two carbon atoms form

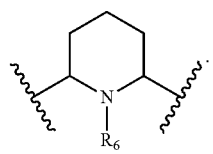

In some embodiments, $R_5$ and $R_7$ together with the carbon atoms to which they are attached and the nitrogen atom connecting the two carbon atoms form

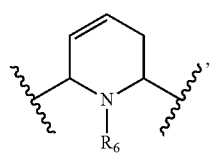

wherein the ring is optionally substituted on a carbon atom of the ring with $C_{1-6}$ alkyl, wherein the $C_{1-6}$ alkyl is optionally substituted with one or more OH. In some embodiments, $R_5$ and $R_7$ together with the carbon atoms to which they are attached and the nitrogen atom connecting the two carbon atoms form

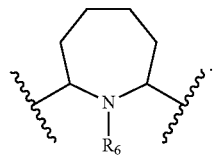

In some embodiments, $R_5$ and $R_7$ together with the carbon atoms to which they are attached and the nitrogen atom connecting the two carbon atoms form

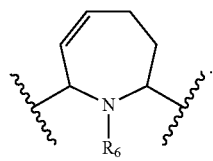

In some embodiments of Formula (III), $R_5$ and $R_7$ together with the carbon atoms to which they are attached and the nitrogen atom connecting the two carbon atoms form a ring having one of the formulas:

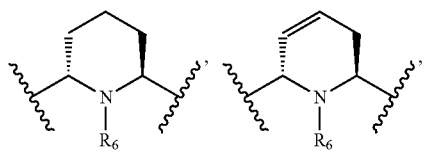

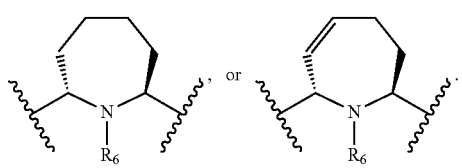

In some embodiments, $R_5$ and $R_7$ together with the carbon atoms to which they are attached and the nitrogen atom connecting the two carbon atoms form

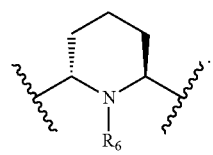

In some embodiments, $R_5$ and $R_7$ together with the carbon atoms to which they are attached and the nitrogen atom connecting the two carbon atoms form

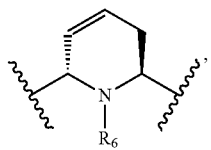

wherein the ring is optionally substituted on a carbon atom of the ring with $C_{1-6}$ alkyl, wherein the $C_{1-6}$ alkyl is optionally substituted with one or more OH. In some embodiments, $R_5$ and $R_7$ together with the carbon atoms to which they are attached and the nitrogen atom connecting the two carbon atoms form

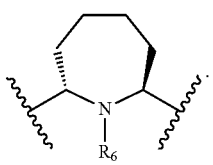

In some embodiments, $R_5$ and $R_7$ together with the carbon atoms to which they are attached and the nitrogen atom connecting the two carbon atoms form

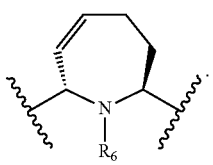

In some embodiments of Formula (III), $R_6$ and $R_7$ together with the carbon and nitrogen atoms to which they are attached form a ring of formula

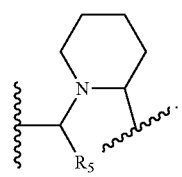

In some embodiments, $R_6$ and $R_7$ together with the carbon and nitrogen atoms to which they are attached form a ring of formula

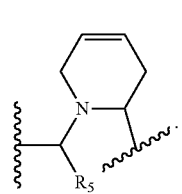

In some embodiments of Formula (III), $R_6$ and $R_7$ together with the carbon and nitrogen atoms to which they are attached form a ring having one of the formulas:

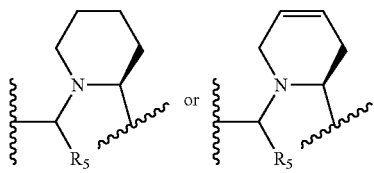

wherein the ring is optionally substituted on a ring carbon atom with $C_{1-6}$ alkyl, wherein the $C_{1-6}$ alkyl is optionally substituted with one or more OH. In some embodiments, $R_6$ and $R_7$ together with the carbon and nitrogen atoms to which they are attached form a ring of formula

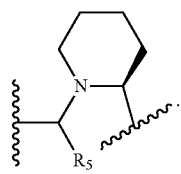

In some embodiments, $R_6$ and R; together with the carbon and nitrogen atoms to which they are attached form a ring of formula

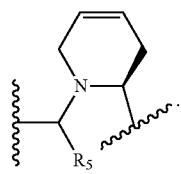

In some embodiments of Formula (III), $R_6$ is selected from H or $C_{1-6}$ alkyl optionally substituted with one or more substituents selected from the group consisting of halogen, $OR^a$, $SR^a$, —$C(O)OR^a$, and —$SC(NH)NH_2$. In some embodiments, $R_6$ is H.

optionally substituted with one or more of $OR^c$ or aryl. In some embodiments, $R_{12}$ is H, and $R_{13}$ is $C_{1-6}$ alkyl optionally substituted with $OR^c$. In some embodiments, $R_{12}$ is H, and $R_{13}$ is $C_{1-6}$ alkyl. In some embodiments, $R_{12}$ is H, and $R_{13}$ is halogen. In some embodiments, $R_{12}$ is H, and $R_{13}$ is fluoro. In some embodiments, each of $R_{12}$ and $R_{13}$ is $C_{1-6}$ alkyl. In some embodiments, each of $R_{12}$ and $R_{13}$ is halogen. For example, each of $R_{12}$ and $R_{13}$ is fluoro. In some embodiments, $R_{12}$ is H, and $R_{13}$ is $OR^c$. In some embodiments, $R_{12}$ is H, and Rn is $N(R^c)_2$. In some such embodiments, each $R^c$ is selected from H or $C_{1-6}$ alkyl. In some other such embodiments, one $R^c$ is H and the other $R^c$ is $C_{1-6}$ alkyl.

In some embodiments of Formula (III), each R is selected from H or $C_{1-6}$ alkyl. In some embodiments, each R is selected from $C_{1-6}$ alkyl or —$(CH_2)$aryl. In some embodiments, each $R^c$ is H. In some embodiments, each $R^c$ is $C_{1-6}$ alkyl. For example, each $R^c$ is methyl. In some embodiments, each $R^c$ is —$(CH_2)$aryl.

In some embodiments of Formula (III), the Cahn-Ingold-Prelog configuration at the carbon atom $R_{13}$ is bonded to is (R). In some embodiments, the Cahn-Ingold-Prelog configuration at the carbon atom $R_{13}$ is bonded to is (S).

In some embodiments of Formula (III), $R_{14}$ is H. In some embodiments, $R_{14}$ is aryl. In some embodiments, the Cahn-Ingold-Prelog configuration at the carbon atom $R_{14}$ is bonded to is (R). In some embodiments, the Cahn-Ingold-Prelog configuration at the carbon atom $R_{14}$ is bonded to is (S).

In some embodiments of Formula (III), $R_{15}$ is H. In some embodiments, $R_{15}$ is $C_{1-6}$ alkyl optionally substituted with one or more $R^b$. For example, $R_{15}$ is $C_{1-6}$ alkyl optionally substituted with one $R^b$. In some embodiments, $R_{15}$ is $C_{4-5}$ alkyl optionally substituted with one $R^b$.

In some embodiments of Formula (III), $R^b$ is selected from $OR^c$, $N(R^c)_2$, and cyclopropyl. For example, $R^b$ is $N(R^c)_2$. In some embodiments, $R^b$ is $NH_2$.

In some embodiments of Formula (III), the compound is a compound of Formula (IIIA):

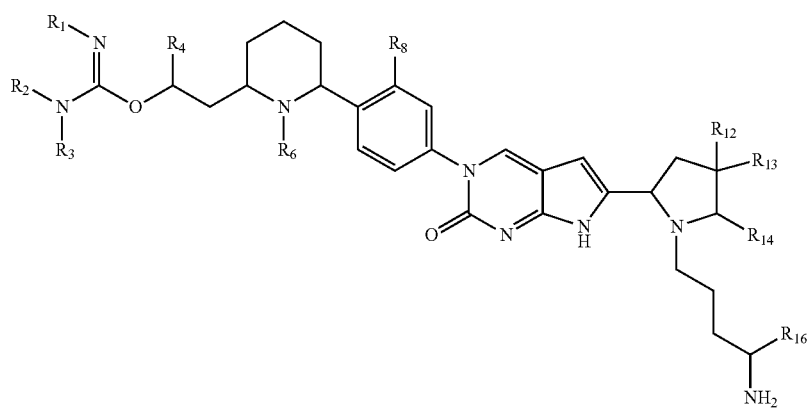

(IIIA)

or a tautomer thereof or a pharmaceutically acceptable salt of the compound or tautomer, wherein:
$R_1$ is selected from H and $C_{1-3}$ alkyl;
$R_2$ is selected from H and $C_{1-3}$ alkyl;
$R_3$ is selected from H and $C_{1-3}$ alkyl;
$R_4$ is selected from H and $C_{1-3}$ alkyl;

In some embodiments of Formula (III), $R_8$ is H. In some embodiments, $R_8$ is halogen. For example, $R_8$ is F.

In some embodiments of Formula (III), each of $R_{12}$ and $R_{13}$ is H. In some embodiments, each of $R_{12}$ and $R_{13}$ is not H. In some embodiments, one of $R_{12}$ and $R_{13}$ is H, and the other is not H. For example, $R_{11}$ is H, and $R_{13}$ is $C_{1-6}$ alkyl $R_6$ is selected from H, $C_{1-6}$ alkyl, and $C_{2-6}$ alkenyl, wherein the $C_{1-6}$ alkyl is optionally substituted with one or more substituents selected from the group consisting of halogen, $OR^a$, $SR^a$, —C(O)$OR^a$, and —SC(NH)$NH_2$;

$R_8$ is selected from H and halogen;

$R_{12}$ is selected from H, halogen, and $C_{1-6}$ alkyl;

$R_{13}$ is selected from H, halogen, $C_{1-6}$ alkyl, $OR^c$, $N(R^c)_2$, wherein $C_{1-6}$ alkyl is optionally substituted with one or more of $OR^c$ and aryl; $R_{14}$ is selected from H and aryl; or $R_{13}$ and $R_{14}$ together with the carbon atoms to which they are attached form a 5- or 6-membered cycloalkyl ring;

$R_{16}$ is $C_{1-6}$ alkyl;

each $R^a$ is independently selected from H and $C_{1-6}$ alkyl;

each $R^c$ is independently selected from hydrogen, $C_{1-6}$ alkyl, aryl, and —(CH$_2$)aryl, wherein the $C_{1-6}$ alkyl and the aryl are each optionally substituted with one or more $R^d$; and each $R^d$ is independently selected from OH, O($C_{1-3}$ alkyl), $NH_2$, NH($C_{1-3}$ alkyl), and N($C_{1-3}$ alkyl)$_2$.

In some embodiments of Formula (IIIA), each of $R_1$, $R_2$, and $R_3$ is H. In some embodiments, two of $R_1$, $R_2$, and $R^3$ are H, and the other is $C_{1-3}$ alkyl. For example, two of $R_1$, $R_2$, and $R_3$ are H, and the other is methyl. In some embodiments, one of $R_1$, $R_2$, and $R_3$ is H, and the other two are $C_{1-3}$ alkyl. For example, one of $R_1$, $R_2$, and $R_3$ is H, and the other two are methyl.

In some embodiments of Formula (IIIA), $R_4$ is H.

In some embodiments of Formula (IIIA), $R_6$ is selected from H or $C_{1-6}$ alkyl optionally substituted with one or more substituents selected from the group consisting of halogen, $OR^a$, $SR^a$, —C(O)$OR^a$, or —SC(NH)$NH_2$. In some embodiments, $R_6$ is H.

In some embodiments of Formula (IIIA), $R_8$ is H. In some embodiments, $R_8$ is halogen. For example, R is F.

In some embodiments, of Formula (IIA), each of $R_{12}$ and $R_{13}$ is H. In some embodiments, each of $R_{12}$ and $R_{13}$ is not H. In some embodiments, one of $R_{12}$ and $R_{13}$ is H, and the other is not H. For example, $R_{12}$ is H, and $R_{13}$ is $C_{1-6}$ alkyl optionally substituted with one or more of $OR^c$ or aryl. In some embodiments, $R_{12}$ is H, and $R_{13}$ is $C_{1-6}$ alkyl optionally substituted with $OR^c$. In some embodiments, $R_{12}$ is H, and $R_{13}$ is $C_{1-6}$ alkyl. In some embodiments, $R_{12}$ is H, and $R_{13}$ is halogen. For example, $R_{12}$ is H, and $R_{13}$ is fluoro. In some embodiments, each of $R_{12}$ and $R_{13}$ is $C_{1-6}$ alkyl. In some embodiments, each of $R_{12}$ and $R_{13}$ is halogen. For example, each of $R_{12}$ and $R_{13}$ is fluoro. In some embodiments, $R_{12}$ is H, and $R_{13}$ is $OR^c$. In some embodiments, $R_{12}$ is H, and $R_{13}$ is $N(R^c)_2$. In some such embodiments, each $R^c$ is selected from H or $C_{1-6}$ alkyl. In other such embodiments, one $R^c$ is H and the other $R^e$ is $C_{1-6}$ alkyl.

In some embodiments of Formula (IIIA), each $R^c$ is selected from H or $C_{1-6}$ alkyl. In some embodiments, $R^c$ is selected from $C_{1-6}$ alkyl or —(CH$_2$)aryl. In some embodiments, $R^c$ is H. In some embodiments, $R^c$ is $C_{1-6}$ alkyl. For example, $R^c$ is methyl. In some embodiments, $R^c$ is —(CH$_2$)aryl. For example, $R^c$ is —(CH$_2$)phenyl.

In some embodiments of Formula (IIA), the Cahn-Ingold-Prelog configuration at the carbon atom $R_{13}$ is bonded to is (R). In some embodiments, the Cahn-Ingold-Prelog configuration at the carbon atom $R_{13}$ is bonded to is (S).

In some embodiments of Formula (IIIA), $R_{14}$ is H. In some embodiments, $R_{14}$ is aryl. In some embodiments, the Cahn-Ingold-Prelog configuration at the carbon atom $R_{14}$ is bonded to is (R). In some embodiments, the Cahn-Ingold-Prelog configuration at the carbon atom $R_{14}$ is bonded to is (S).

In some embodiments of Formula (IIIA), $R_{16}$ is $C_{1-6}$ alkyl. For example, $R_{16}$ is methyl. In some embodiments, the Cahn-Ingold-Prelog configuration at the carbon atom $R_{16}$ is bonded to is (S). In some embodiments, the Cahn-Ingold-Prelog configuration at the carbon atom $R_{16}$ is bonded to is (R).

In some embodiments of Formula (III), the compound is a compound of Formula (IIIB):

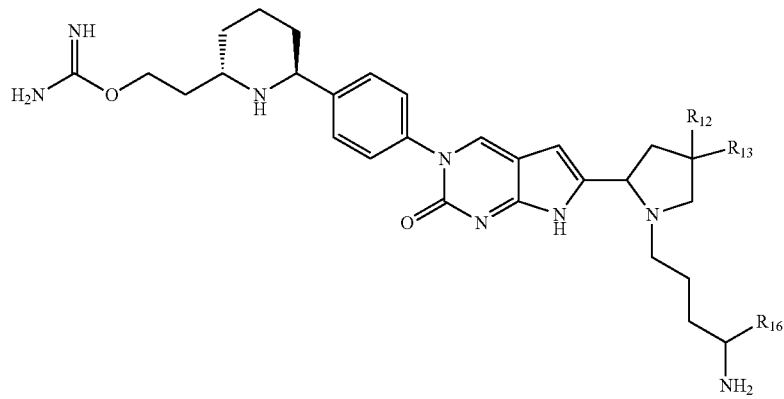

(IIIB)

or a tautomer thereof or a pharmaceutically acceptable salt of the compound or tautomer, wherein:

$R_{12}$ is selected from H, halogen, and $C_{1-6}$ alkyl;

$R_{13}$ is selected from H, halogen, $C_{1-6}$ alkyl, $OR^c$, $N(R^c)_2$, wherein $C_{1-6}$ alkyl is optionally substituted with one or more of $OR^c$ and aryl;

$R_{16}$ is $C_{1-6}$ alkyl;

each $R^c$ is independently selected from hydrogen, $C_{1-6}$ alkyl, aryl, and —(CH$_2$)aryl, wherein the $C_{1-6}$ alkyl and the aryl are each optionally substituted with one or more $R^d$; and each $R^d$ is independently selected from OH, O($C_{1-3}$ alkyl), $NH_2$, NH($C_{1-3}$ alkyl), and N($C_{1-3}$ alkyl)$_2$.

In some embodiments of Formula (IIIB), each of $R_{12}$ and $R_1$ is H. In some embodiments, each of $R_{12}$ and $R_{13}$ is not H. In some embodiments, one of $R_{12}$ and $R_1$ is H, and the other is not H. In some embodiments, $R_{11}$ is H, and $R_1$ is $C_{1-6}$ alkyl optionally substituted with one or more of $OR^c$ or aryl. In some embodiments, $R_{11}$ is H, and $R_{13}$ is $C_{1-6}$ alkyl optionally substituted with $OR^c$. In some embodiments, $R_{12}$ is H, and Rn is $C_{1-6}$ alkyl. In some embodiments, $R_{12}$ is H, and $R_1$ is halogen. For example, $R_{12}$ is H, and $R_{13}$ is fluoro. In some embodiments, each of $R_{12}$ and $R_{13}$ is $C_{1-6}$ alkyl. In some embodiments, each of $R_2$ and $R_{13}$ is halogen. For example, each of $R_{12}$ and $R_{13}$ is fluoro. In some embodiments, $R_{12}$ is H, and $R_{13}$ is $OR^c$. In some embodiments, $R_{12}$ is H, and $R_{13}$ is $N(R^c)_2$.

In some embodiments of Formula (IIIB), each R is selected from H or $C_{1-6}$ alkyl. In some embodiments, each $R^c$ is selected from $C_{1-6}$ alkyl or —$(CH_2)$aryl. In some embodiments, each $R^c$ is H. In some embodiments, each $R^e$ is $C_{1-6}$ alkyl. For example, each $R^c$ is methyl. In some embodiments, each $R^c$ is —$(CH_2)$aryl.

In some embodiments of Formula (IIB), the Cahn-Ingold-Prelog configuration at the carbon atom $R_{13}$ is bonded to is (R). In some embodiments, the Cahn-Ingold-Prelog configuration at the carbon atom $R_{13}$ is bonded to is (S).

In some embodiments of Formula (IIIB), $R_{16}$ is $C_{1-6}$ alkyl. For example, $R_{16}$ is methyl. In some embodiments, the Cahn-Ingold-Prelog configuration at the carbon atom $R_{16}$ is bonded to is (S). In some embodiments, the Cahn-Ingold-Prelog configuration at the carbon atom $R_{16}$ is bonded to is (R).

In some embodiments, one of $R_{12}$ and $R_1$ is H, and the other of $R_{12}$ and $R_1$ is not H; and $R_1$, is methyl, wherein the Cahn-Ingold-Prelog configuration at the carbon atom $R_{16}$ is bonded to is (S). In some embodiments, $R_{11}$ is H, and $R_3$ is $OR^c$; R is selected from H or $C_{1-6}$ alkyl; and $R_{16}$ is methyl, wherein the Cahn-Ingold-Prelog configuration at the carbon atom $R_{16}$ is bonded to is (S).

In some embodiments of Formula (I), Formula (II), or Formula (III), the present disclosure provides any one of compounds listed in Table 1, or a tautomer thereof or a pharmaceutically acceptable salt of the compound or tautomer.

TABLE 1

| # | Structure | MW (g/mol) | ESI, m/z [M + H]$^+$ |
|---|---|---|---|
| 1 | 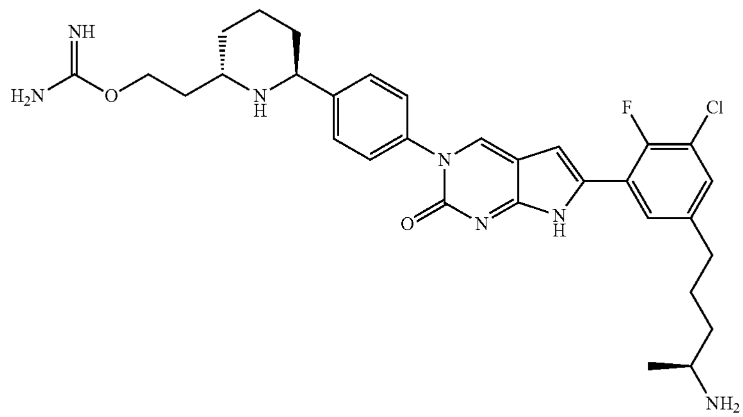 [SMILES: C[C@H](N)CCCc1cc(Cl)c(F)c(-c2cc3cn(-c4ccc([C@@H]5CCC[C@@H](CCOC(=N)N)N5)cc4)c(=O)nc3[nH]2)c1] | 593.27 | 568.1 |
| 2 | 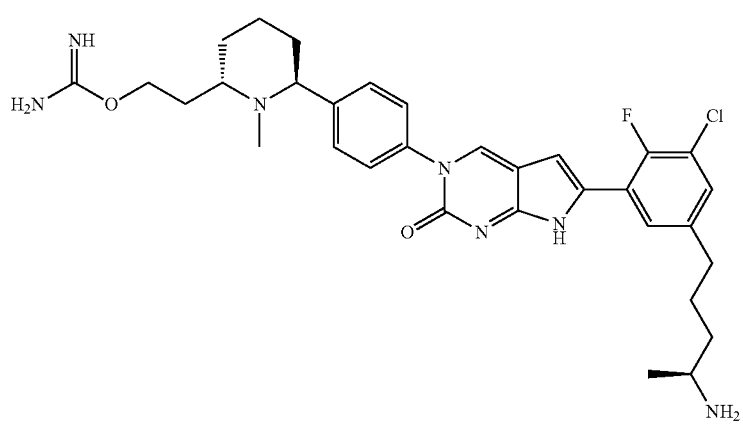 [SMILES: C[C@H](N)CCCc1cc(Cl)c(F)c(-c2cc3cn(-c4ccc([C@@H]5CCC[C@@H](CCOC(=N)N)N5C)cc4)c(=O)nc3[nH]2)c1] | 608.16 | 608.8 |

TABLE 1-continued

| # | Structure | MW (g/mol) | ESI, m/z [M + H]+ |
|---|---|---|---|
| 3 | 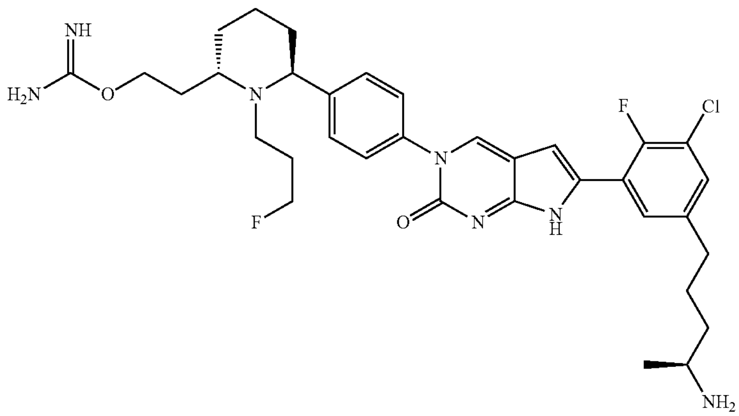 [SMILES: C[C@H](N)CCCc1cc(Cl)c(F)c(-c2cc3cn(-c4ccc([C@@H]5CCC[C@@H](CCOC(=N)N)N5CCCF)cc4)c(=O)nc3[nH]2)c1] | 654.20 | 654.7 |
| 4 | 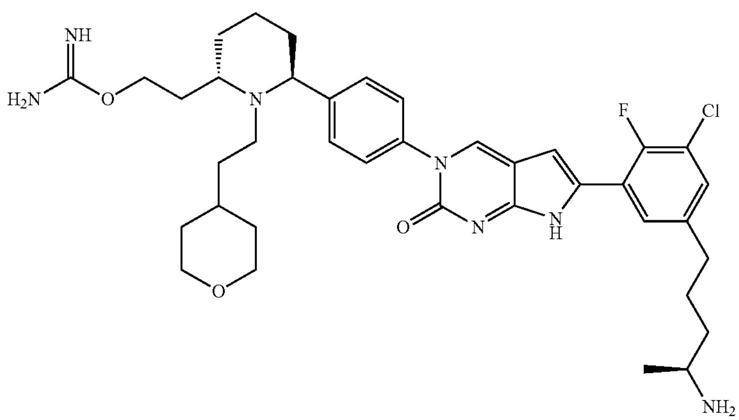 [SMILES: C[C@H](N)CCCc1cc(Cl)c(F)c(-c2cc3cn(-c4ccc([C@@H]5CCC[C@@H](CCOC(=N)N)N5CCC5CCOCC5)cc4)c(=O)nc3[nH]2)c1] | 706.30 | 706.5 |
| 5 | 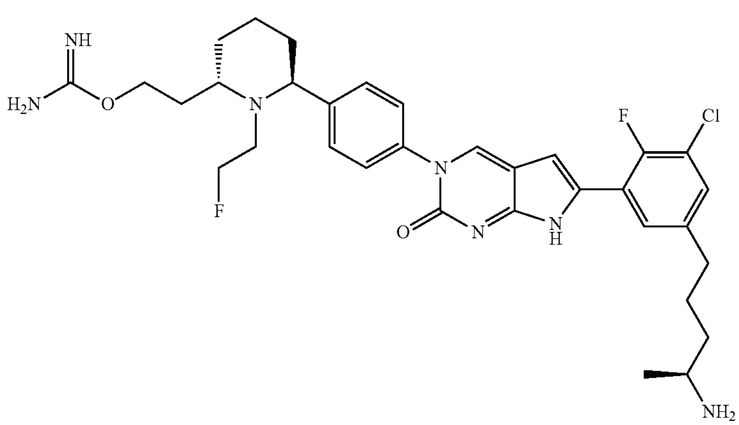 [SMILES: C[C@H](N)CCCc1cc(Cl)c(F)c(-c2cc3cn(-c4ccc([C@@H]5CCC[C@@H](CCOC(=N)N)N5CCF)cc4)c(=O)nc3[nH]2)c1] | 640.18 | 640.0 |

TABLE 1-continued

| # | Structure | MW (g/mol) | ESI, m/z [M + H]+ |
|---|---|---|---|
| 6 | 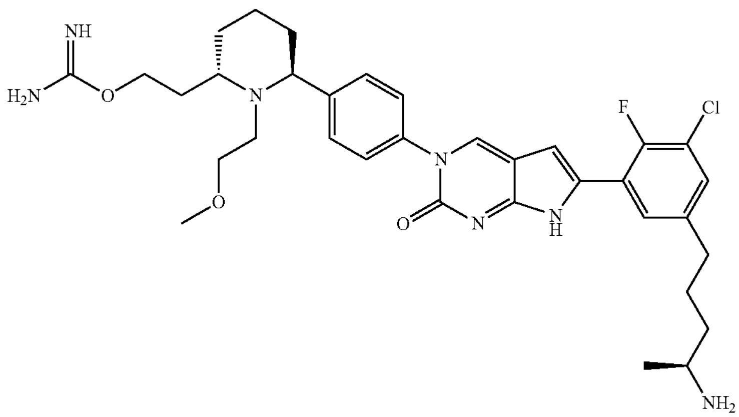 [SMILES: COCCN1[C@H](CCOC(=N)N)CCC[C@H]1c1ccc(-n2cc3cc(-c4cc(CCC[C@H](C)N)cc(Cl)c4F)[nH]c3nc2=O)cc1] | 542.21 | 652.0 |
| 7 | 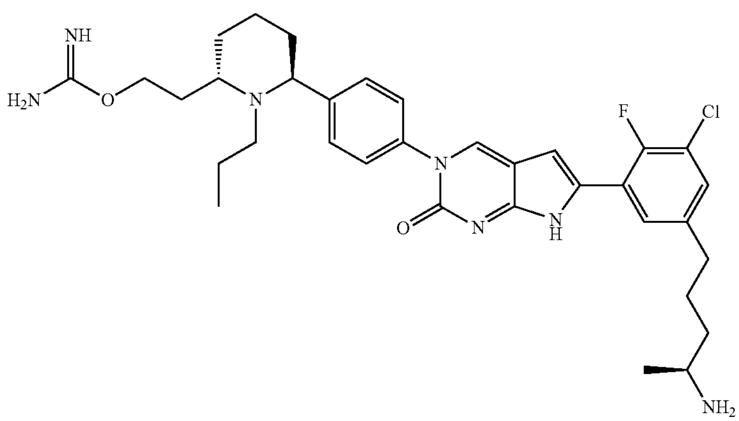 [SMILES: CCCN1[C@H](CCOC(=N)N)CCC[C@H]1c1ccc(-n2cc3cc(-c4cc(CCC[C@H](C)N)cc(Cl)c4F)[nH]c3nc2=O)cc1] | 636.21 | 636.0 |
| 8 | 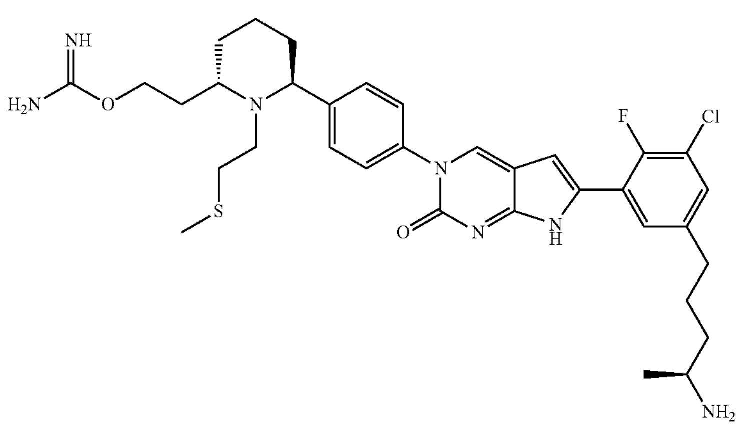 [SMILES: CSCCN1[C@H](CCOC(=N)N)CCC[C@H]1c1ccc(-n2cc3cc(-c4cc(CCC[C@H](C)N)cc(Cl)c4F)[nH]c3nc2=O)cc1] | 668.27 | 668.0 |

TABLE 1-continued

| # | Structure | MW (g/mol) | ESI, m/z [M + H]+ |
|---|---|---|---|
| 9 | 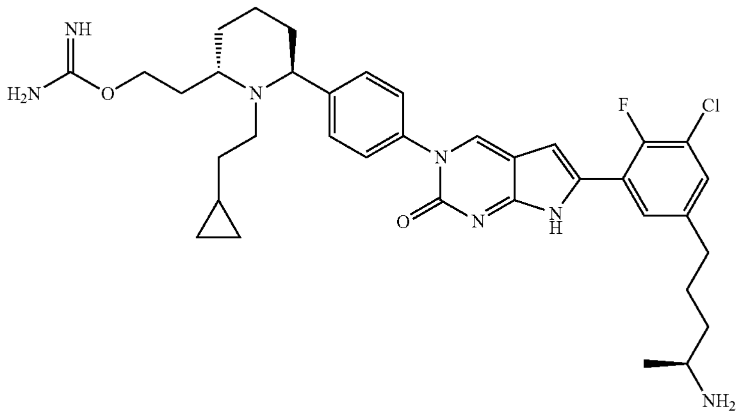 [SMILES: C[C@H](N)CCCc1cc(Cl)c(F)c(-c2cc3cn(-c4ccc([C@@H]5CCC[C@@H](CCOC(=N)N)N5CCC5CC5)cc4)c(=O)nc3[nH]2)c1] | 662.25 | 662.0 |
| 10 | 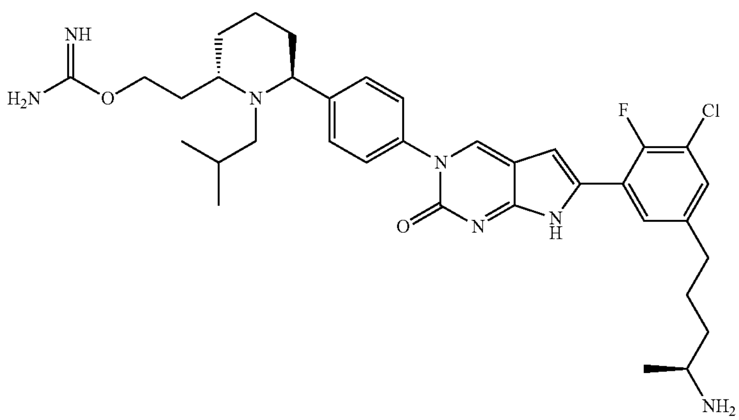 [SMILES: CC(C)CN1[C@H](CCOC(=N)N)CCC[C@H]1c1ccc(-n2cc3cc(-c4cc(CCC[C@H](C)N)cc(Cl)c4F)[nH]c3nc2=O)cc1] | 650.24 | 650.0 |
| 11 | 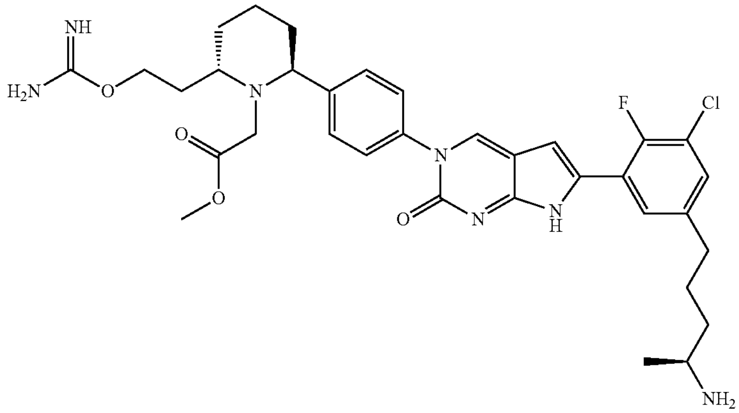 [SMILES: COC(=O)CN1[C@H](CCOC(=N)N)CCC[C@H]1c1ccc(-n2cc3cc(-c4cc(CCC[C@H](C)N)cc(Cl)c4F)[nH]c3nc2=O)cc1] | 666.20 | 666.0 |

TABLE 1-continued
| # | Structure | MW (g/mol) | ESI, m/z [M + H]+ |
|---|---|---|---|
| 12 | 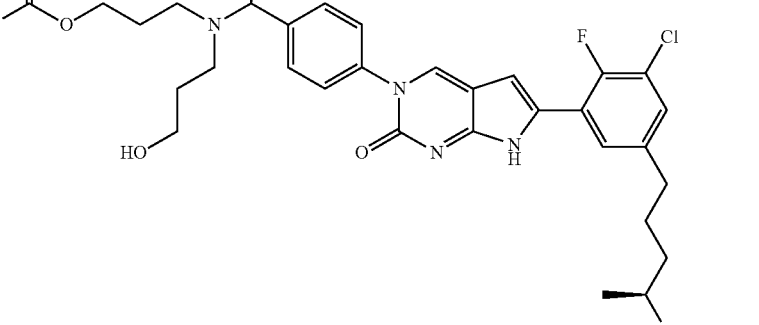 | 652.21 | 652.0 |
| 13 | 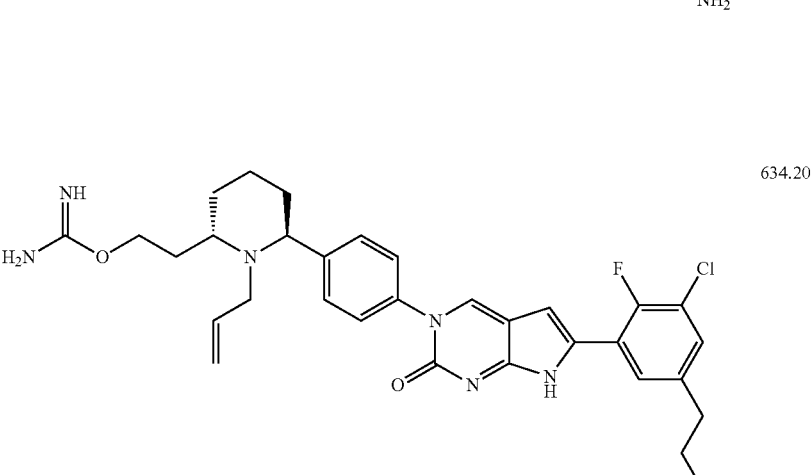 | 634.20 | 634.0 |
| 14 | 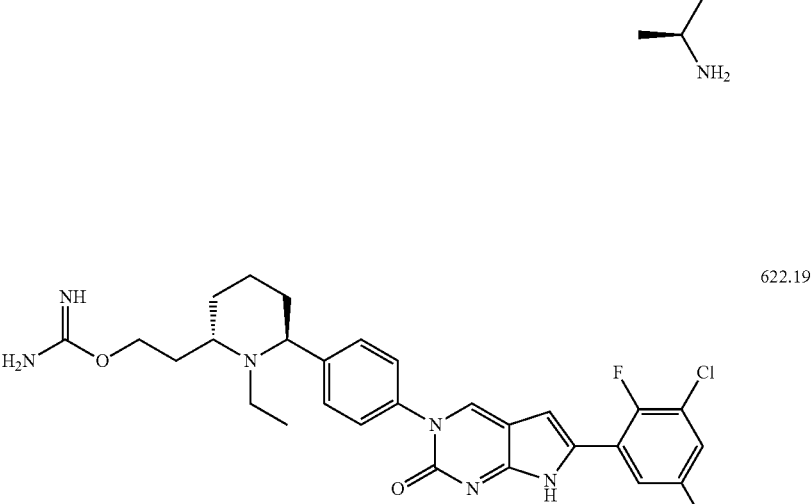 | 622.19 | 622.8 |

TABLE 1-continued

| # | Structure | MW (g/mol) | ESI, m/z [M + H]+ |
|---|---|---|---|
| 15 | 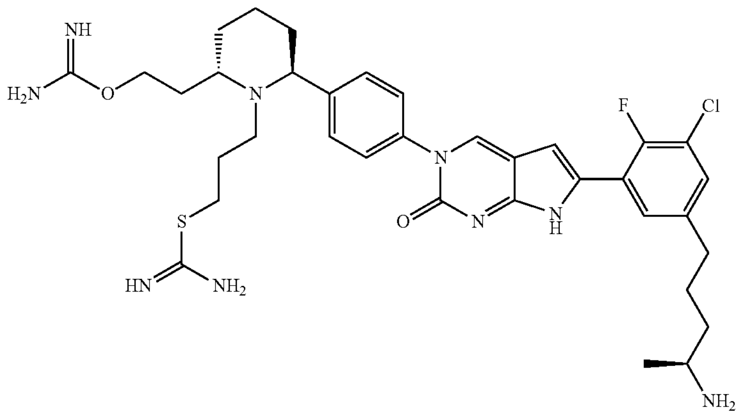 [SMILES: C[C@H](N)CCCc1cc(Cl)c(F)c(-c2cc3cn(-c4ccc([C@@H]5CCC[C@@H](CCOC(=N)N)N5CCCSC(=N)N)cc4)c(=O)nc3[nH]2)c1] | 710.31 | 710.0 |
| 16 | 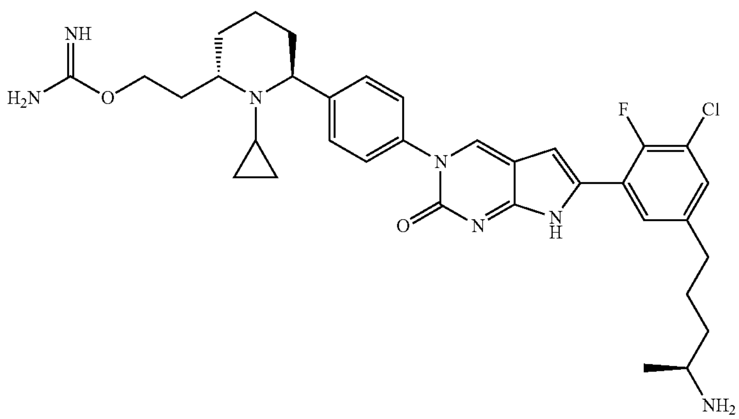 [SMILES: C[C@H](N)CCCc1cc(Cl)c(F)c(-c2cc3cn(-c4ccc([C@@H]5CCC[C@@H](CCOC(=N)N)N5C5CC5)cc4)c(=O)nc3[nH]2)c1] | 634.20 | 634.8 |
| 17 | 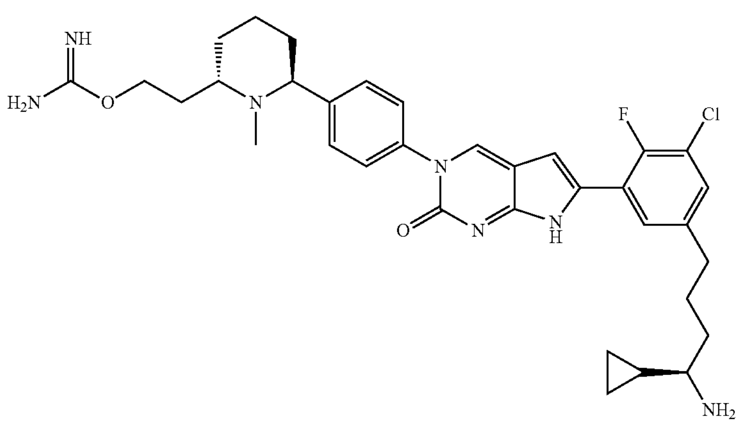 [SMILES: CN1[C@H](CCOC(=N)N)CCC[C@H]1c1ccc(-n2cc3cc(-c4cc(CCC[C@@H](N)C5CC5)cc(Cl)c4F)[nH]c3nc2=O)cc1] | 634.20 | 634.2 |

TABLE 1-continued

| # | Structure | MW (g/mol) | ESI, m/z [M + H]+ |
|---|---|---|---|
| 18 | 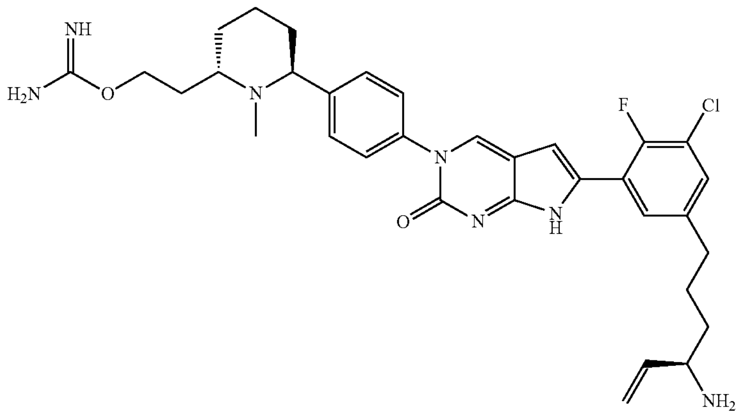 [SMILES: C=C[C@H](N)CCCc1cc(Cl)c(F)c(-c2cc3cn(-c4ccc([C@@H]5CCC[C@@H](CCOC(=N)N)N5C)cc4)c(=O)nc3[nH]2)c1] | 620.17 | 620.9 |
| 19 | 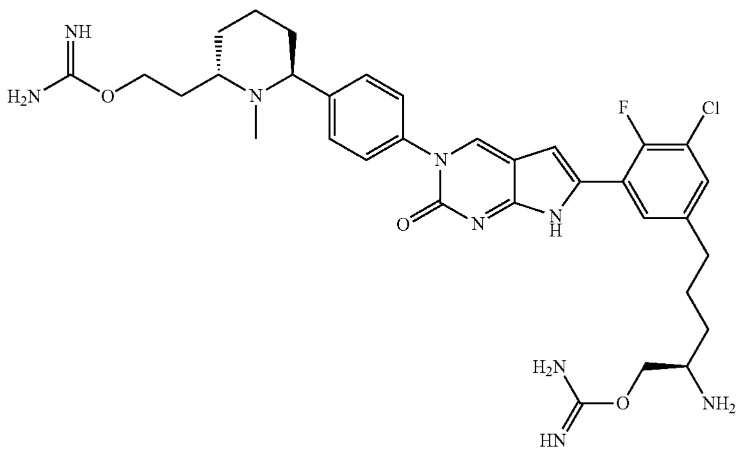 [SMILES: CN1[C@H](CCOC(=N)N)CCC[C@H]1c1ccc(-n2cc3cc(-c4cc(CCC[C@@H](N)COC(=N)N)cc(Cl)c4F)[nH]c3nc2=O)cc1] | 666.20 | 666.8 |
| 20 | 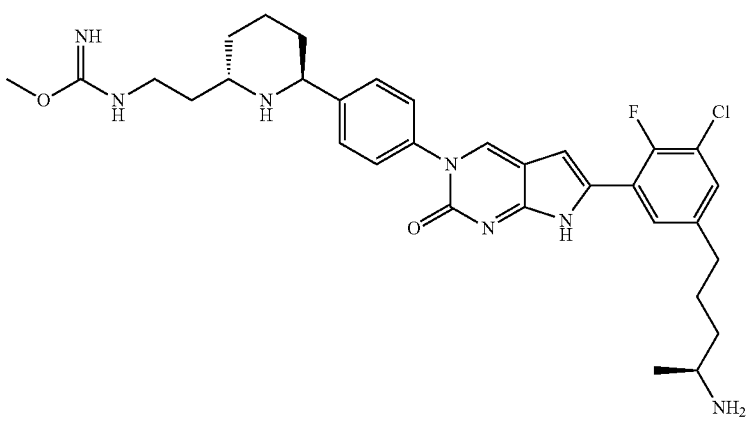 [SMILES: COC(=N)NCC[C@@H]1CCC[C@@H](c2ccc(-n3cc4cc(-c5cc(CCC[C@H](C)N)cc(Cl)c5F)[nH]c4nc3=O)cc2)N1] | 608.16 | 608.0 |

In Table 1 above, a bond indicated by a squiggle bond indicates a stereoisomer where the identity of the specific orientation of the bond has not been specified.

In some embodiments, the present disclosure relates to a compound or a tautomer thereof, or a pharmaceutically acceptable salt of the compound or tautomer that binds the ribosome. In some embodiments, the ribosome is a bacterial ribosome.

In some embodiments, the present disclosure relates to a pharmaceutical composition comprising a compound disclosed herein, or a tautomer thereof, or a pharmaceutically acceptable salt of the compound or tautomer, and a pharmaceutically acceptable carrier. In some embodiments, the present disclosure relates to a compound or a tautomer thereof, or a pharmaceutically acceptable salt of the compound or tautomer disclosed herein and a means for delivery.

In some embodiments, the present disclosure relates to a method of treating, preventing, reducing the risk of or delaying the onset of a disease state in a human or animal comprising administering to the human or animal in need thereof an effective amount of a compound disclosed herein, or a tautomer thereof, or a pharmaceutically acceptable salt of the compound or tautomer.

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt of the compound or tautomer.

In some embodiments, the present disclosure relates to use of a compound disclosed herein, or a tautomer thereof, or a pharmaceutically acceptable salt of the compound or tautomer, in the manufacture of a medicament for treating, preventing, reducing the risk of, or delaying the onset of, a microbial infection in a human or animal. In another aspect, the present disclosure relates to a compound for use in the manufacture of a medicament for treating a microbial infection in a subject, wherein the compound is selected from a compound of the present disclosure, or a tautomer thereof, or a pharmaceutically acceptable salt of the compound or tautomer.

In some embodiments, the present disclosure relates to a compound for use in the manufacture of a medicament for preventing a microbial infection in a subject, wherein the compound is selected from a compound of the present disclosure, or a tautomer thereof, or a pharmaceutically acceptable salt of the compound or tautomer.

In some embodiments, the present disclosure relates to a compound for use in the manufacture of a medicament for reducing the risk of a microbial infection in a subject, wherein the compound is selected from a compound of the present disclosure, or a tautomer thereof, or a pharmaceutically acceptable salt of the compound or tautomer.

In some embodiments, the present disclosure relates to a compound for use in the manufacture of a medicament for delaying the onset of a microbial infection in a subject, wherein the compound is selected from a compound of the present disclosure, or a tautomer thereof, or a pharmaceutically acceptable salt of the compound or tautomer.

In some embodiments, the present disclosure relates to a compound disclosed herein, or a tautomer thereof, or a pharmaceutically acceptable salt of the compound or tautomer, for use in treating, preventing, reducing the risk of, or delaying the onset of a microbial infection in a human or animal.

In some embodiments, the present disclosure relates to a compound disclosed herein, or a tautomer thereof, or a pharmaceutically acceptable salt of the compound or tautomer, for use in treating a microbial infection in a human or animal.

In some embodiments, the present disclosure relates to a compound disclosed herein, or a tautomer thereof, or a pharmaceutically acceptable salt of the compound or tautomer, for use in preventing a microbial infection in a human or animal.

In some embodiments, the present disclosure relates to a compound disclosed herein, or a tautomer thereof, or a pharmaceutically acceptable salt of the compound or tautomer, for use in reducing the risk of a microbial infection in a human or animal.

In some embodiments, the present disclosure relates to a compound disclosed herein, or a tautomer thereof, or a pharmaceutically acceptable salt of the compound or tautomer, for use in delaying the onset of a microbial infection in a human or animal.

In some embodiments, a microbial infection as described herein is caused by one or more microoganisms selected from the group consisting of: *Enterococcus faecium, Staphylococcus aureus, Klebsiella pneumoniae, Acinetobacter baumannii, Pseudomonas aeruginosa, Enterobacter species*, and *Escherichia coli*. This group of microorganisms can be referred to generally as the ESKAPE pathogens. In some embodiments, the microbial infection is caused by a microorganism which is resistant to at least one antibacterial. For example, the microorganism can be classified as multi-drug resistant or extremely-drug resistant. In some embodiments, the compounds provided herein have in vitro activity across the ESKAPE pathogens. For example, one or more of the compounds provided herein exhibit individual MICs and/or MIC90s of ≤4 mg/L. In some embodiments, one or more of the compounds provided herein exhibit individual MICs and/or MIC90s of ≤2 mg/L. For example, one or more of the compounds provided herein exhibit individual MICs and/or MIC90s of ≤1 mg/L. In some embodiments, one or more of the compounds provided herein exhibit individual MICs and/or MIC90s of ≤0.5 mg/L. For example, one or more of the compounds provided herein exhibit individual MICs and/or MIC90s of ≤0.25 mg/L. In some embodiments, one or more of the compounds provided herein exhibit individual MICs and/or MIC90s of ≤0.125 mg/L. For example, one or more of the compounds provided herein exhibit individual MICs and/or MIC90s of ≤0.05 mg/L.

In some embodiments, the compounds provided herein lack cross-resistance to current therapies, with demonstrated activity against one or more multidrug-resistant strains of *E. faecium* and MRSA; Enterobacteriaceae featuring cephalosporinases (ESBLs and AmpCs) and carbapenemases (classes A, B and D); *P. aeruginosa* strains with normal and raised efflux; and *A. baumannii*. In some embodiments, the compounds provided herein demonstrate one or more of low rate (E−10) and extent of resistance development in *E. coli*; activity in exemplary burden models of infection in the neutropenic thigh, ascending kidney and lung as well as in peritonitis models; and safety scorecard highlighted by 14-day dose-range-finding toxicology studies in rat and monkey, at multiples the exposures observed for efficacy, with minimal histopathological findings.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of the compound or tautomer, wherein the microbial infection is caused by one or more of the following microorganisms: *Acinetobacter* spp. (*Acinetobacter baumanni*), *Bacteroides distasonis, Bacteroides fragilis, Bacteroides ovatus, Bacteroides thetaiolaomicron, Bacteroides uniformis, Bacteroides vulgalus, Citrobacter freundii, Citrobacter koser, Chlamydia trachomatis, Chlamydia psittaci, Chlamydia pneumoniae, Chlamydia pecorum, Chlamydia suis, Chlamydia muridarum, Chlamydophila psittaci, Chlamydophila pneumoniae, Chlamydophila pecorum, Clostridium clostridioforme, Clostridium perfringens, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium lentum, Fusobacterium* spp., *Haemophilus influenzae* (including beta-lactamase positive isolates), *Haemophihus parainflu-*

*enzae, Klebsiella pneumoniae* (including ESBL and KPC producing isolates), *Klebsiella oxytoca* (including ESBL and KPC producing isolates), *Legionella pneumophilia Moraxella catarrhalis, Morganella morganii, Mycoplasma* spp., *Neisseria gonorrhoeae* (including *Neisseria gonorrhoeae* ATCC49266, *Neisseria gonorrhoeae* 255123, *Neisseria gonorrhoeae* 255124, *Neisseria gonorrhoeae* 255125, *Neisseria gonorrhoeae* 255126, *Neisseria gonorrhoeae* 255127, *Neisseria gonorrhoeae* J9104300210, *Neisseria gonorrhoeae* J9107400107, *Neisseria gonorrhoeae* J9109510210, *Neisseria gonorrhoeae* J9108110210), *Peptostreptococcus* spp., *Porphyromonas asaccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophononas maltophilia, Streptococcus agalactiae, Streptococcus constellatus, Streptococcus pneumoniae* (penicillin susceptible and resistant isolates), *Streptococcus pyogenes*, or *Streptococcus pyogenes*.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of the compound or tautomer, wherein the infection is caused by or involves one or more microorganisms selected from: *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, Citrobacter freundii, Citrobacter koser, Chlamydia trachomatis, Chlamydia psittaci, Chlamydia pneumoniae, Chlamydia pecorum, Chlamydia suis, Chlamydia muridarum, Chlamydophila psittaci, Chlamydophila pneumoniae, Chlamydophila pecorum, Clostridium clostridioforme, Clostridium perfringens, Enterobacter aerogenes, Enterobacter cloacae, Enterococcus faecalis, Enterococcus* spp., *Escherichia coli, Eubacterium lentum, Fusobacterium* spp., *Haemophilus influenzae, Haemophilus parainfluenzae, Klebsiella pneumoniae, Klebsiella oxytoca, Legionella pneumophilia, Moraxella catarrhalis, Morganella morganii, Mycoplasma* spp., *Neisseria gonorrhoeae, Peptostreptococcus* spp., *Porphyromonas asaccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus, Staphylococcus epidermidis, Stenotrophomonas maltophilia, Streptococcus agalactiae, Streptococcus constellatus, Streptococcus pneumoniae, Streptococcus pyogenes*, and *Streptococcus pyogenes*.

In some embodiments, the present disclosure relates to a method wherein the infection is caused by or involves one or more of aerobic and facultative gram-positive microorganisms selected from: *Staphylococcus aureus, Streptococcus pneumoniae, Enterococcus* spp., *Streptococcus agalactiae, Streptococcus pyogenes*, and *Staphylococcus epidermidis*.

In some embodiments, the present disclosure relates to a method wherein the infection is caused by or involves one or more of aerobic and facultative gram-negative microorganisms selected from: *Escherichia coli, Haemophilus influenzae, Klebsiella pneumoniae, Citrobacter freundii, Chlamydia trachomatis, Chlamydia psittaci, Chlamydia pneumoniae, Chlamydia pecorum, Chlamydia suis, Chlamydia muridarum, Chlamydophila psittaci, Chlamydophila pneumoniae, Chlamydophila pecorum, Enterobacter aerogenes, Enterobacter cloacae, Morganella morganii, Neisseria gonorrhoeae, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca, Proteus vulgaris, Providencia rettgeri*, and *Providencia stuartii*.

In some embodiments, the present disclosure relates to a method wherein the infection is caused by or involves one or more anaerobic microorganisms: *Bacteroides fragilis, Bacteroides distasonis, Bacteroides ovatus, Bacteroides thetaiotaomicron, Bacteroides uniformis, Clostridium clostridioforme, Eubacterium lentum, Peptostreptococcus* spp., *Porphyromonas asaccharolytica, Prevotella bivia, Bacteroides vulgatus, Clostridium perfringens*, and *Fusobacterium* spp.

In some embodiments, the present disclosure relates to a method, wherein the microorganism *Enterococcus* spp. is selected from vancomycin susceptible isolate and vancomycin resistant isolate. For example, vancomycin-resistant *Enterococci*.

In some embodiments, the present disclosure relates to a method wherein the microorganism *Escherichia coli* is selected from extended spectrum beta-lactamase (ESBL) producing isolate and *Klebsiella pneumoniae* carbapenemase (KPC) producing isolate.

In some embodiments, the present disclosure relates to a method wherein the microorganism *Haemophilus influenzae* is a beta-lactamase positive isolate.

In some embodiments, the present disclosure relates to a method wherein, the microorganism *Klebsiella pneumoniae* is selected from extended spectrum beta-lactamase (ESBL) producing isolate and *Klebsiella pneumoniae* carbapenemase (KPC) producing isolate.

In some embodiments, the present disclosure relates to a method wherein the microorganism *Klebsiella oxytoca* selected from extended spectrum beta-lactamase (ESBL) producing isolate and *Klebsiella pneumoniae* carbapenemase (KPC) producing isolate.

In some embodiments, the present disclosure relates to a method wherein the microorganism *Staphylococcus aureus* is selected from methicillin susceptible isolate and methicillin resistant isolate.

In some embodiments, the present disclosure relates to a method wherein the microorganism *Staphylococcus epidermidis* is selected from methicillin susceptible isolate and methicillin resistant isolate.

In some embodiments, the present disclosure relates to a method wherein the microorganism *Streptococcus pneumoniae* is selected from penicillin susceptible isolate and penicillin resistant isolate.

In some embodiments, the present disclosure relates to a method wherein the microorganism *Neisseria gonorrhoeae* is selected from susceptible and resistant isolates, including, for example, ceftriaxone-resistant, ciprofloxacin-resistant and azithromycin-resistant isolates.

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of the compound or tautomer, wherein the microbial infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei.*

In some embodiments, the present disclosure relates to a method of treating, preventing, reducing the risk of, or delaying the onset of a microbial infection in a human or animal comprising administering to the human or animal an effective amount of a compound or a tautomer thereof, or a pharmaceutically acceptable salt of the compound or tautomer, wherein the microbial infection is caused by one or more of the following microorganisms: *Bacillus anthracis* and Multi Drug Resistant (MDR) *anthracis, Franciscella tularensis, Yersinia pestis, Burkholderia mallei*, and *Burkholderia pseudomallei.*

In some embodiments, the present disclosure relates to a method of treating, preventing, reducing the risk of, or delaying the onset of a microbial infection in a human or animal comprising administering to the human or animal an effective amount of a compound disclosed herein, or a tautomer thereof, or a pharmaceutically acceptable salt of the compound or tautomer, or use of a compound disclosed herein, or a tautomer thereof, or a pharmaceutically acceptable salt of the compound or tautomer, in the manufacture of a medicament for treating, preventing, reducing the risk of, or delaying the onset of a microbial infection in a human or animal, wherein the microbial infection is selected from the group consisting of: a skin infection, a Gram positive infection, a Gram negative infection, nosocomial pneumonia, community acquired pneumonia, post-viral pneumonia, hospital acquired pneumonia/ventilator associated pneumonia, a respiratory tract infection such as chronic respiratory tract infection (CRTI), acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant *Enterococci* infection, a ciprofloxacin-resistant *Neisseria gonorrhoeae* infection, a carbapenem-resistant Enterobacteriaceae infection, a linezolid-resistant organism infection, gonorrhea, chlamydia, and tuberculosis.

The compounds of the present disclosure can be used, for example for the treatment of patients with moderate to severe infections, which may be caused by susceptible isolates of the indicated microorganisms.

In some embodiments, the present disclosure relates to a method of treating, preventing, reducing the risk of, or delaying the onset of a complicated intra-abdominal infection in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a complicated intra-abdominal infection in a human or animal.

In some embodiments, the complicated intra-abdominal infection is selected from polymicrobial infections such as abscess due to *Escherichia coli, Clostridium clostridioforme, Eubacterium lentum, Peptostreptococcus* spp., *Bacteroides fragilis, Bacteroides distasonis, Bacteroides ovatus, Bacteroides thetaiotaomicron, Bacteroides uniformis, Streptococcus anginosus, Streptococcus constellatus, Enterococcus faecalis, Proteus mirabilis*, or *Clostridium perfringens.*

In some embodiments, the present disclosure relates to a method of treating, preventing, reducing the risk of, or delaying the onset of a complicated skin and skin structure infection (cSSSI, also known as acute bacterial skin and skin structure infections or ABSSSI) in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a complicated skin and skin structure infection.

In some embodiments, the complicated skin and skin structure infection is selected from diabetic foot infections without osteomyelitis due to *Staphylococcus aureus* (methicillin susceptible and resistant isolates), *Streptococcus agalactiae, Streptococcus pyogenes, Escherichia coli, Klebsiella pneumoniae, Proteus mirabilis, Bacteroides fragilis, Peptostreptococcus species, Porphyromonas asaccharolytica*, or *Prevotella bivia.*

In some embodiments, the present disclosure relates to a method of treating, preventing, reducing the risk of, or delaying the onset of a community acquired pneumonia (CAP) in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of community acquired pneumonia.

In some embodiment, the community acquired pneumonia is due to *Streptococcus pneumoniae* (penicillin susceptible and resistant isolates) including cases with concurrent bacteremia, *Haemophilus influenzae* (including beta-lactamase positive isolates), *Moraxella catarrhalis*, or atypical bacteria like *Mycoplasma* spp.

In some embodiments, the present disclosure relates to a method of treating, preventing, reducing the risk of, or delaying the onset of a complicated urinary tract infection (cUTI) in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a complicated urinary tract infection.

In some embodiment, the complicated urinary tract infection is selected from pyelonephritis due to *Escherichia coli*, concurrent bacteremia, or *Klebsiella pneumoniae.*

In some embodiments, the present disclosure relates to a method of treating, preventing, reducing the risk of, or delaying the onset of an acute pelvic infection in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of an acute pelvic infection.

In some embodiments, the acute pelvic infection is selected from postpartum endomyometritis, septic abortion and post-surgical gynecologic infections and the infection is due to a microorganism selected from *Streptococcus agalactiae, Escherichia coli, Bacteroides fragilis, Porphyromonas asaccharolytica, Peptostreptococcus* spp., and *Prevotella hivia.*

In some embodiments, the present disclosure relates to a method of treating, preventing, reducing the risk of, or delaying the onset of a hospital acquired pneumonia (HAP)/ventilator associated pneumonia (VAP) in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of hospital acquired pneumonia/ventilator associated pneumonia.

In some embodiments, the hospital acquired pneumonia/ventilator associated pneumonia is due to a microorganism selected from *Streptococcus pneumoniae* (penicillin susceptible and resistant isolates), *Staphylococcus aureus* (methicillin susceptible and resistant isolates), *Klebsiella pneumoniae, Pseudomonas aeruginosa, Acinetobacter* spp., *Stenotrophomonas maltophilia, Haemophilus influenzae* (including beta-lactamase positive isolates), and *Legionella pneumophilia.*

The compounds or tautomers or pharmaceutically acceptable salts of the compounds or tautomers of the present disclosure may also be useful for the prevention, prophylaxis, or reduction of surgical site infections. In some embodiments, the compounds or tautomers or pharmaceutically acceptable salts of the compounds or tautomers of the present disclosure are useful following elective colorectal surgery.

Appropriate specimens for bacteriological examination should be obtained in order to isolate and identify the causative organisms and to determine their susceptibility to the compounds of the present disclosure. Therapy with the compounds or tautomers or pharmaceutically acceptable salts of the compounds or tautomers of the present disclosure may be initiated empirically before results of these tests are known; once results become available, antimicrobial therapy should be adjusted accordingly.

To reduce the development of drug-resistant bacteria and maintain the effectiveness of the compounds or tautomers or pharmaceutically acceptable salts of the compounds or tautomers of the present disclosure and other antibacterial drugs, the compounds or tautomers or pharmaceutically acceptable salts of the compounds or tautomers should be used only to treat or prevent infections that are proven or strongly suspected to be caused by susceptible bacteria. When culture and susceptibility information are available, they should be considered in selecting or modifying antibacterial therapy. In the absence of such data, local epidemiology and susceptibility patterns may contribute to the empiric selection of therapy.

In some embodiments, the present disclosure relates to a method of treating, preventing, reducing the risk of, or delaying the onset of a microbial infection due to an aerobic or facultative gram-positive microorganism in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a microbial infection due to an aerobic or facultative gram-positive microorganism.

In some embodiments, the aerobic or facultative gram-positive microorganism is selected from: *Staphylococcus aureus* (methicillin susceptible and resistant isolates), *Streptococcus pneumoniae* (penicillin susceptible and resistant isolates), *Enterococcus* spp. (vancomycin susceptible and resistant isolates), *Streptococcus agalactiae, Streptococcus pyogenes,* and *Staphylococcus epidermidis* (methicillin susceptible and resistant isolates).

In some embodiments, the present disclosure relates to a method of treating, preventing, reducing the risk of, or delaying the onset of a microbial infection due to an aerobic and facultative gram-negative microorganism in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a microbial infection due to an aerobic or facultative gram-positive microorganism.

In some embodiments, the aerobic and facultative gram-negative microorganism is selected from: *Escherichia coli* [including extended spectrum beta-lactamase (ESBL) and *Klebsiella pneumoniae* (KPC) producing isolates), *Haemophilus influenzae* (including Beta-lactamase positive isolates), *Klebsiella pneumoniae* (including ESBL and KPC producing isolates), *Citrobacter freundii, Enterobacter aerogenes, Enterobacter cloacae, Morganella morganii, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca* (including ESBL and KPC producing isolates), *Proteus vulgaris, Providencia rettgeri,* and *Providencia stuartii.*

In some embodiments, the present disclosure relates to a method of treating, preventing, reducing the risk of, or delaying the onset of a microbial infection due to an anaerobic microorganism in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a microbial infection due to an anaerobic microorganism.

In some embodiments, the anaerobic microorganism is selected from: *Bacteroides fragilis, Bacteroides distasonis, Bacteroides ovatus, Bacteroides thetaiotaomicron, Bacteroides uniformis, Closiridium clostridioforme, Eubacterium lentum, Peptostreptococcus species, Porphyromonas asaccharolytica, Prevotella bivia, Bacteroides vulgates, Clostridium perfringens,* and *Fusobacterium* spp.

In some embodiments, the present disclosure relates to a method of treating or reducing the risk of a microbial infection in a human or animal comprising administering to the human or animal an effective amount of a compound disclosed herein, or a tautomer thereof, or a pharmaceutically acceptable salt of the compound or tautomer, or to the use of a compound disclosed herein, or a tautomer thereof, or a pharmaceutically acceptable salt of the compound or tautomer, in the manufacture of a medicament for treating, preventing, reducing the risk of, or delaying the onset of a microbial infection.

In some embodiments, the microorganism is *Legionella pneumophilia*.

In some embodiments, the microorganism *Enterococcus* spp. is selected from vancomycin susceptible isolate and vancomycin resistant isolate. In some embodiments, the microorganism *Escherichia coli* is selected from extended spectrum beta-lactamase (ESBL) producing isolate and *Klebsiella pneumoniae* carbapenemase (KPC) producing isolate. In some embodiments, the microorganism *Haemophilus influenzae* is a beta-lactamase positive isolate. In some embodiments, the microorganism *Klebsiella pneumoniae* is selected from extended spectrum beta-lactamase (ESBL) producing isolate and *Klebsiella pneumoniae* carbapenemase (KPC) producing isolate. In some embodiments, the microorganism *Klebsiella oxytoca* selected from extended spectrum beta-lactamase (ESBL) producing isolate and *Klebsiella pneumoniae* carbapenemase (KPC) producing isolate. In some embodiments, the microorganism *Staphylococcus aureus* is selected from methicillin susceptible isolate and methicillin resistant isolate. In some embodiments, the microorganism *Staphylococcus epidermidis* is selected from methicillin susceptible isolate and methicillin resistant isolate. In some embodiments, the microorganism *Streptococcus pneumoniae* is selected from penicillin susceptible isolate and penicillin resistant isolate.

In some embodiments, the microorganism is colistin-resistant. For example, a microorganism that is colistin-resistant exhibits a minimum inhibitory concentration (MIC) for colistin of >2 µg/ml). In some embodiments, the microorganism is be a gram negative bacteria such as a *Pseudomonas* (e.g., *Pseudomonas aeruginosa*), *Escherichia* (*Escherichia coli*), or *Klebsiella* (e.g., *Klebsiella pneumoniae*) species that is resistant to treatment with the antibacterial agent known as colistin (polymyxin E). For example, the colistin-resistant microorganism is selected from *Pseudomonas aeruginosa*, *Klebsiella pneumoniae*, and *Acinetobacter baumannii*. In some embodiments, the colistin-resistant microorganism is a *Stenotrophomonas*, *Burkholderia*, *Proteus*, *Serratia*, *Morganella*, or *Providencia* species (e.g., the specific species provided herein).

In some embodiments, a method or use disclosed herein is a method or use to treat a subject that would be subjected to a surgical or invasive medical procedure. Such a subject can be considered to be in need of the methods of treating, reducing the risk of or preventing the infection due to a surgical procedure or an invasive medical procedure. Such a subject can also be considered to be in need of peri-operative prophylaxis.

In some embodiments, a method or use provided herein is a method for treating sepsis in a subject comprising administering to the subject a therapeutically effective amount of a compound or a tautomer thereof, or a pharmaceutically acceptable salt of the compound of tautomer thereof. In some such embodiments, the patient is a pediatric patient, a geriatric patient, or a patient having a weakened immune system related to another disease or disorder (e.g., cancer, diabetes, major trauma, or burns). In some embodiments, the sepsis is severe sepsis. In some embodiments, the sepsis is septic shock. In some embodiments, the treatment of sepsis further comprises administration to the subject one or more of intravenous fluids, compounds capable of raising blood pressure, mechanical ventilation, and dialysis.

In some embodiments, the present disclosure provides a method of treating, preventing, reducing the risk of, or delaying the onset of a microbial infection in a human or animal, the method including administering to the human or animal in need thereof an effective amount of a compound disclosed herein, or a tautomer thereof, or a pharmaceutically acceptable salt of the compound or tautomer. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In some embodiments, provided is the use of one or more compounds disclosed herein, including stereoisomers, tautomers, and salts thereof, in the manufacture of a medicament for treating, preventing, reducing the risk of, or delaying the onset of a microbial infection in a human or animal. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In some embodiments, provided are one or more compounds disclosed herein, including stereoisomers, tautomers, and salts thereof, for use in treating, preventing, reducing the risk of, or delaying the onset of a microbial infection in a human or animal. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In one embodiment, provided is a method of treating a microbial infection in a subject, that includes administering to the subject an effective amount of one or more compounds of a compound disclosed herein, or a tautomer thereof, or a pharmaceutically acceptable salt of the compound or tautomer, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In one embodiment, provided is a method of preventing a microbial infection in a subject, that includes administering to the subject an effective amount of a compound disclosed herein, or a tautomer thereof, or a pharmaceutically acceptable salt of the compound or tautomer, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In one embodiment, provided is a method of reducing the risk of a microbial infection in a subject, that includes administering to the subject an effective amount of a compound disclosed herein, or a tautomer thereof, or a pharmaceutically acceptable salt of the compound or tautomer, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In one embodiment, provided is a method of delaying the onset of a microbial infection in a subject, that includes administering to the subject an effective amount of a compound disclosed herein, or a tautomer thereof, or a pharmaceutically acceptable salt of the compound or tautomer, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens.

In some embodiments, a bacterium which can be used as a biological weapon possesses one or more characteristics that include, but are not limited to, being easily being produced or disseminated, being easily transmitted from person to person, having the potential for moderate or high morbidity, having the potential for moderate or high mortality, having the potential for causing public panic and social disruption, requiring special action for public health preparedness, and requiring specific enhancements for diagnosis and disease surveillance.

In another embodiment, a bacterium which can be used as a biological weapon is stable or viable, for example, the bacterium is capable of performing all or part of its normal biological functions, such as replicating, forming spores, and infecting a subject, under various conditions. In some embodiments, the bacterium is stable or viable in one or more conditions that include, but are not limited to, heat, cold, high pressure, low pressure, acidic or basic conditions, humidity, dryness, and radiation, including extreme conditions.

In one embodiment, a bacterium which can be used as a biological weapon is stable or viable at a temperature above about 25° C., such as above about 30° C., about 40° C., about 50° C., about 60° C., about 70° C., about 80° C., about 90° C., about 100° C., about 125° C., about 150° C., about 175° C., or above about 200° C. In another embodiment, a bacterium which can be used as a biological weapon is stable or viable at a temperature below about 25° C., such as below about 20° C., about 10° C., about 5° C., about 0° C., about −10° C., about −20° C., about −30° C., about −40° C., about −50° C., about −60° C., about −70° C., about −100° C., or below about −150° C.

In one embodiment, a bacterium which can be used as a biological weapon is capable of infecting a subject under various conditions, such as various pressures. In one embodiment, a bacterium which can be used as a biological weapon is stable or viable under pressure above about $5\times10^5$ Pa, such as above about $10\times10^5$ Pa, about $15\times10^5$ Pa, about $20\times10^5$ Pa, about $30\times10^5$ Pa, about $40\times10^5$ Pa, about $50\times10^5$ Pa, about $75\times10^5$ Pa, or about $100\times10^5$ Pa. In another embodiment, a bacterium which can be used as a biological weapon is stable or viable under pressure below about $0.5\times10^5$ Pa, such as below about $0.2\times10^5$ Pa, about $0.1\times10^5$ Pa, about $0.05\times10^5$ Pa, about $0.02\times10^5$ Pa, about $0.01\times10^5$ Pa, about $0.005\times10^5$ Pa, about $0.002\times10^5$ Pa, or about $0.001\times10^5$ Pa.

In one embodiment, a bacterium which can be used as a biological weapon is stable or viable at a pH above about 8.0, such as above about 8.5, about 9.0, about 9.5, about 10.0, about 10.5, about 11.0, about 11.5, about 12.0, about 12.5, about 13.0, about 13.5, or about 14.0. In another embodiment, a bacterium which can be used as a biological weapon is stable or viable at a pH below about 6.0, such as below about 5.5, about 5.0, about 4.5, about 4.0, about 3.5, about 3.0, about 2.5, about 2.0, about 1.5, about 1.0, about 0.5, or about 0.0.

In one embodiment, a bacterium which can be used as a biological weapon is stable or viable under a relative humidity of about 10%, such as about 20%, about 30%, about 40%, about 50%, about 60%, about 70%, about 75%, about 80%, about 85%, about 90%, about 95%, or about 99%.

In another embodiment, a bacterium which can be used as a biological weapon is stable or viable under UV radiation, X-ray radiation, α radiation, β radiation, or γ radiation.

In one embodiment, a bacterium which can be used as a biological weapon is able to form spores.

In some embodiments, a bacterium which can be used as a biological weapon can be dispersed in air or in liquid. In one embodiment, the bacterium is in aerosol form, for example, the bacterium is formulated as an aerosol. In another embodiment, the bacterium is in powder form, for example, the bacterium is formulated as powder.

In one embodiment, a bacterium which can be used as a biological weapon includes a bacterium which is resistant to existing antibiotics. In some embodiments, the bacterium is resistant to tetracycline antibiotics, including, but not limited to, tetracycline, doxycycline, minocycline, sancycline, methacycline, chlortetracycline, and deoxytetracycline, and a combination thereof. In some embodiments, the bacterium is resistant to other antibiotics, including, but not limited to, aminoglycosides, such as gentamicin and kanamycin, colistin, methicillin, oxacillin, vancomycin, penicillin, linezolid, fluoroquinolones, such as ciprofloxacin, ceftazidime, and macrolides, such as azithromycin. In some embodiments, a bacterium which can be used as a biological weapon includes a bacterium which is resistant to gentamicin. In some embodiments, a bacterium which can be used as a biological weapon includes a bacterium which is resistant to colistin. In some embodiments, a bacterium which can be used as a biological weapon includes a bacterium which is resistant to gentamicin and colistin.

In some embodiments of the disclosed methods, the one or more microorganisms are biodefense category A or biodefense category B pathogens. Biodefense category A pathogens are those organisms or biological agents that pose the highest risk to national security and public health because they (1) can be easily disseminated or transmitted from person to person, (2) result in high mortality rates and have the potential for major public health impact, (3) might cause public panic and social disruption, and (4) require special action for public health preparedness. Examples of category A pathogens include, but are not limited to, *Bacillus anthracis* (anthrax), *Francisella tularensis* (tularemia), *Yersinia pestis* (plague), Ebola, Marburg, Ebola-like viruses such as Bundibugyo ebolavirus, Sudan ebolavirus, TaiForest ebolavirus, Zaire ebolavirus and Marburg-like viruses such as Marburg virus and Ravn virus. In some embodiments, the one or more microorganisms are selected from the group consisting of biodefense category A pathogens *Bacillus anthracis* (anthrax), *Yersinia pestis* (plague), and *Francisella tularensis* (tularemia).

Biodefense category B pathogens are the second highest priority organisms or biological agents. They are moderately easy to disseminate, result in moderate morbidity rates and low mortality rates, and require specific enhancements for diagnostic capacity and enhanced disease surveillance. Examples of category B pathogens include, but are not limited to, *Burkholderia pseudomallei* (melioidosis), *Coxiella burnetii* (Q fever), *Brucella* species (brucellosis), *Burkhoderia mallei* (glanders), *Chlamydia psittaci* (psittacosis), *Rickeltsia prowazekii* (typhus fever), diarrheagenic *E. coli*, pathogenic *Vibrios, Shigella* species, *Salmonella, Listeria monocytogenes, Campylobacter jejuni, Yersinia enterocolitica, Staphylococcus* enterotoxin B, and Hepatitis A. In some embodiments, the one or more microorganisms are selected from the group consisting of biodefense category B pathogens *Burkholderia pseudomallei* (melioidosis), *Coxiella burnetii* (Q fever), *Brucella* species (brucellosis), *Burkhoderia mallei* (glanders), *Chlamydia psittaci* (psittacosis), *Rickettsia prowazekii* (typhus fever), diarrheagenic *E. coli*, pathogenic *Vibrios, Shigella* species, *Salmonella, Listeria monocytogenes, Campylobacter jejuni*, and *Yersinia enterocolitica.*

More examples of category A or B pathogens are provided by the National Institute of Allergy and Infectious Diseases (NIAID) at http://www.niai d.nih.gov/topics/bio defenserelated/bi odefense/pages/cata.aspx#, the contents of which are hereby incorporated by reference in its entirety.

In some embodiments, a bacterium which can be used as a biological weapon includes, but is not limited to, a bacterium of the *Bacillus cereus* group. The *Bacillus cereus* group of bacteria includes *Bacillus anthracis* (the etiologic agent of anthrax), *Bacillus cereus, Bacillus weihenstephanensis* (a food borne pathogen), *Bacillus thuringiensis* (an insect pathogen), and *Bacillus mycoides*. In some embodiments, the bacterium is selected from *Bacillus anthracis*, multidrug-resistant (MDR) anthrax, *Francisella tularensis, Clostridium botulinum, Yersinia pestis, Burkholderia mallei, Burkholderia pseudomallei, Brucella species, Shigella species, Coxiella burnetii, Chlamydia psittaci, Clostridium perfringens, Rickettsia prowazekii*, diarrheagenic *E. coli*, pathogenic *Vibrios, Salmonella, Campylobacter jejuni, Yersinia enterocolitica*, and *Listeria monocytogenes*. In some embodiments, the microorganism (bacterium) is selected from *Bacillus anthracis, Franciscella tularensis, Yersinia pestis, Burkholderia mallei*, and *Burkholderia pseudomallei*. In some embodiments, the microorganism (bacterium) is selected from *Burkholderia mallei* and *Burkholderia pseudomallei*. In some embodiments, the microorganism (bacterium) is *Burkholderia pseudomallei.*

In some embodiments, a bacterium which can be used as a biological weapon is *Bacillus anthracis* or multi drug-resistant (MDR) anthrax.

In some embodiments, a bacterium which can be used as a biological weapon is *Burkholderia pseudomallei.*

In some embodiments, a bacterium which can be used as a biological weapon includes, but is not limited to, gram-positive pathogens, gram-negative pathogens, anaerobic pathogens, or atypical pathogens, or a combination thereof. In some embodiments, the bacterium includes methicillin-susceptible *Staphylococcus aureus* (MSSA), methicillin-resistant *Staphylococcus aureus* (MRSA), oxacillin-susceptible *Staphylococcus aureus*, oxacillin-resistant *Staphylococcus aureus*, oxacillin-resistant coagulase-negative *Staphylococcus, Enterococcus faecalis, Enterococcus faecium*, vancomycin-susceptible *Enterococcus faecium*, vancomycin-resistant *Enterococcus faecium*, vancomycin-susceptible *Enterococcus faecalis*, vancomycin-resistant *Enterococcus faecalis, Streptococcus pneumoniae*, penicillin-susceptible *Streptococcus pneumonia*, penicillin-resistant *Streptococcus pneumoniae* (PRSP), *Streptococcus pyogenes, Streptococcus agalactiae, Haemophilus influenzae, Moraxella catarrhalis, Neisseria gonorrhoeae, Escherichia coli, Shigella* spp., *Salmonella* spp., *Klebsiella pneumoniae, Enterobacter aerogenes, Enterobacter cloacae, Serratia marcescens, Acinetobacter baumannii, Stenotrophomonas maltophilia, Bacteroides fragilis, Clostridium perfringens, Chlamydia pneumoniae, Legionella pneumophila, Proteus mirabilis, Pseudomonas aeruginosa*, and *Burkholderia cepacia.*

In some embodiments, the one or more microorganisms are extremely-drug resistant Gram-positive or Gram-negative pathogens.

In some embodiments, provided is a method of treating, preventing, reducing the risk of, or delaying the onset of a microbial infection in a subject that is caused by or involves one or more microorganisms which are capable of being used as biological weapons that includes administering a compound disclosed herein, or a tautomer thereof, or a pharmaceutically acceptable salt of the compound or tautomer.

In some embodiments, the one or more microorganisms are biodefense category A pathogens. In some embodiments, the one or more microorganisms are biodefense category A pathogens selected from *Bacillus anthracis* (anthrax), *Yersiniapestis* (plague), and *Francisella tularensis* (tularemia).

In some embodiments, the one or more microorganisms are biodefense category B pathogens. In some embodiments, the one or more microorganisms are biodefense category B pathogens *Burkholderia pseudomallei* (melioidosis), *Coxiella burnetii* (Q fever), *Brucella* species (brucellosis), *Burkhoderia mallei* (glanders), *Chlamydia psittaci* (psittacosis), *Rickettsia prowazekii* (typhus fever), diarrheagenic *E. coli*, pathogenic *Vibrios, Shigella* species, *Salmonella, Listeria monocytogenes, Campylobacter jejuni*, and *Yersinia enterocolitica.*

In some embodiments, the one or more microorganisms are selected from *Bacillus anthracis, Franciscella tularensis, Yersinia pestis, Burkholderia mallei*, and *Burkholderia pseudomallei.*

In some embodiments, the one or more microorganisms are selected from *Burkholderia mallei* and *Burkholderia pseudomallei*. In some embodiments, the one or more microorganisms are *Burkholderia pseudomallei.*

In some embodiments, provided is a method of treating, preventing, reducing the risk of, or delaying the onset of a microbial infection in a subject that is caused by or involves one or more microorganisms which are extremely-drug resistant Gram-positive or Gram-negative pathogens that includes administering a compound disclosed herein, or a tautomer thereof, or a pharmaceutically acceptable salt of the compound or tautomer.

In some embodiments, provided is a method of treating a microbial infection in a subject that includes administering a compound disclosed herein, or a tautomer thereof, or a pharmaceutically acceptable salt of the compound or tautomer, after the subject has been exposed to the microorganism, but before the subject develops any symptom of the microbial infection. In some embodiments, the microorganism is a bacterium. In some embodiments, the microbial infection is a bacterial infection. In some embodiments, a compound disclosed herein, or a tautomer thereof, or a pharmaceutically acceptable salt of the compound or tautomer, is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the subject has been exposed to the microorganism, but before the subject develops any symptoms. In another embodiment, provided is a method of treating a microbial infection in a subject that includes administering a compound disclosed herein, or a tautomer thereof, or a pharmaceutically acceptable salt of the compound or tautomer, after the subject develops a symptom after the subject has been exposed to the microorganism. In some embodiments, the microorganism is a bacterium. In one embodiment, a compound disclosed herein, or a tautomer thereof, or a pharmaceutically acceptable salt of the compound or tautomer, is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the subject develops a symptom.

In another embodiment, provided is a method of treating a microbial infection in a subject that includes administering a compound disclosed herein, or a tautomer thereof, or a pharmaceutically acceptable salt of the compound or tautomer, after the subject's suspected exposure to the microorganism, but before the subject develops any symptom of the microbial infection. In one embodiment, the compound disclosed herein, or a tautomer thereof, or a pharmaceutically acceptable salt of the compound or tautomer, is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the subject's suspected exposure to the microorganism, but before the subject develops any symptoms. In some embodiments, the microorganism is a bacterium.

In some embodiments, provided is a method of preventing a microbial infection in a subject that includes administering a compound disclosed herein, or a tautomer thereof, or a pharmaceutically acceptable salt of the compound or tautomer, before the subject has been exposed to the microorganism. In some embodiments, the microorganism is a bacterium. In some embodiments, the microbial infection is a bacterial infection. In some embodiments, the compound disclosed herein, or a tautomer thereof, or a pharmaceutically acceptable salt of the compound or tautomer, is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks before the subject has been exposed to the microorganism.

In another embodiment, provided is a method of preventing a microbial infection in a subject that includes administering a compound disclosed herein, or a tautomer thereof, or a pharmaceutically acceptable salt of the compound or tautomer, before or after an event which raises the risk of the subject being exposed to the microorganism. In some embodiments, the microorganism is a bacterium. The event includes, but is not limited to, an attack, for example, a terrorist attack, with a biological weapon and the subject's entry into a risky territory, such as a battlefield. In one embodiment, a compound disclosed herein, or a tautomer thereof, or a pharmaceutically acceptable salt of the compound or tautomer, is administered to the subject about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks before the event. In another embodiment, a compound disclosed herein, or a tautomer thereof, or a pharmaceutically acceptable salt of the compound or tautomer is administered to the subject about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the event.

In another embodiment, the method of the present disclosure includes, before administering a compound disclosed herein, or a tautomer thereof, or a pharmaceutically acceptable salt of the compound or tautomer, identifying a subject at risk of being exposed to a microorganism which can be used as a biological weapon. In some embodiments, the microorganism is a bacterium. In some embodiments, the subject at risk of being exposed to a microorganism which can be used as a biological weapon includes, but is not limited to, a subject travelling to, entering, or being in a conflict region, for example, a battlefield or combat zone, including military personnel, intelligence personnel, and animals used in the military, a subject engaged or about to be engaged in a security operation, such as governmental authorities (for example, police, governmental investigators, and secret service members) and other personnel (for example, doctors, nurses, and rescue workers), and animals used in such an operation, and a subject in an geographical area that can be a target of a terrorist attack, for example, a metropolitan area, a city, an area where there is a large population (for example, above 100,000, above 200,000, above 500,000, above 1 million, above 2 million, above 5 million, or above 10 million), or a location or area to which damage is likely to cause a threat to national security or public health (for example, a nuclear power plant, a chemical plant, an airport, or a hospital).

In some embodiments, provided is a method of treating a bacterial infection in a subject, where the subject is exposed or suspected of being exposed to a bacterium or a component thereof, that includes administering to the subject an effective amount of a compound disclosed herein, or a tautomer thereof, or a pharmaceutically acceptable salt of the compound or tautomer. In another embodiment, provided is a method a method of preventing a bacterial infection in a subject, where the subject is at a risk of being exposed to a bacterium or a component thereof, that includes administering to the subject an effective amount of a compound disclosed herein, or a tautomer thereof, or a pharmaceutically acceptable salt of the compound or tautomer. In one embodiment, the bacterium or a component thereof is formulated as an aerosol or power. In another embodiment, the bacterial component is a bacterial spore.

In some embodiments, the present disclosure relates to a method, use, or compound disclosed herein, wherein the amount of compound or a tautomer thereof, or a pharmaceutically acceptable salt of the compound or tautomer comprises from 0.1 mg to 1500 mg. For example, a dose of active compound can range from about 0.1 mg to about 1250 mg; about 0.1 mg to about 1000 mg; about 0.1 mg to about 800 mg; about 0.1 mg to about 500 mg; about 0.1 mg to about 250 mg; about 0.1 mg to about 100 mg; about 0.1 mg to about 50 mg; about 0.1 mg to about 25 mg; about 0.1 mg to about 20 mg; about 0.1 mg to about 10 mg; about 0.1 mg to about 5 mg; about 0.1 mg to about 1 mg; about 0.1 mg to about 0.5 mg; about 0.5 mg to about 1500 mg; about 1 mg to about 1500 mg; about 2.5 mg to about 1500 mg; about 5 mg to about 1500 mg; about 10 mg to about 1500 mg; about 50 mg to about 1500 mg; about 100 mg to about 1500 mg; about 250 mg to about 1500 mg; about 500 mg to about 1500 mg; about 750 mg to about 1500 mg; about 1000 mg to about 1500 mg; about 1250 mg to about 1500 mg; about 0.25 mg to about 2.5 mg; about 0.5 mg to about 5 mg; about 1 mg to about 10 mg; about 5 to about 20 mg; about 10 mg to about 50 mg; about 25 mg to about 75 mg; about 20 mg to about 100 mg; about 50 mg to about 200 mg; about 100 mg to about 500 mg; about 250 mg to about 750 mg; about 200 mg to about 800 mg; about 500 mg to about 1000 mg; or about 750 mg to about 1250 mg.

In some embodiments, the present disclosure relates to a method, use, or compound disclosed herein wherein the compound, or a tautomer thereof, or a pharmaceutically acceptable salt of the compound or tautomer, is administered optically, ophthalmically, nasally, orally, parenterally, topically, or intravenously.

In some embodiments, the present disclosure relates to a method of synthesizing a compound disclosed herein, or a tautomer thereof, or a pharmaceutically acceptable salt of the compound or tautomer.

In some embodiments, the present disclosure relates to a medical device containing a compound disclosed herein or a tautomer thereof, or a pharmaceutically acceptable salt of the compound or tautomer. In some embodiments, the device is a stent.

3. Synthesis of the Compounds of the Disclosure

The compounds of the present disclosure can be synthesized by using art recognized techniques, such as those described in US 2012-0220566, WO 2012/173689, or PCT/US2014/054869, the contents of each of which are incorporated herein by reference in their entireties. The compounds thus obtained can be further purified, for example, by flash column chromatography, high performance liquid chromatography, crystallization, or any known purification method.

In one embodiment, compounds of the present disclosure can be synthesized according to the exemplary method described below.

The specific approaches and compounds shown in the schemes above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R_1$, $R_2$, $R_3$, etc.) or not. The suitability of a chemical group in a compound structure for use in the synthesis of another compound is within the knowledge of one of ordinary skill in the art.

Additional methods of synthesizing compounds of the formulae herein and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Fieser L et al., Fieser and Fieser's Reagents for Organic Synthesis, John Wiley and Sons (1994); and Paquette L, ed., Encyclopedia of Reagents for Organic Synthesis, John Wiley and Sons (1995) and subsequent editions thereof.

4. Characterization of Compounds of the Disclosure

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules disclosed herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is an inhibitor of protein synthesis.

(4) Antimicrobial assays and other evaluation. Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

(5) The translation-only assay for ribosomal protein production uses purified 70S ribosomes, corresponding S100 extracts containing the biological molecules necessary to support protein translation, and mRNA encoding firefly luciferase or another protein reporter. The resulting luminescence signal is proportional to protein translation and is determined by a luminescence assay plate reader (i.e. Victor2V Multilabel Reader). This assay is performed with varying concentrations of potential translation inhibitors in the assay. The resulting data are used to calculate IC50 values of inhibition for the compounds using appropriate software (i.e. MDL Assay Explorer with a one-site competition model of binding).

The in vitro activity of the compounds of the present disclosure can be determined. Antimicrobial testing is typically performed to determine the minimum inhibitory concentration (MIC). Minimum inhibitory concentrations (MICs) are determined by the microdilution method in a final volume of 100 μl according to protocols outlined by The Clinical and Laboratory Standards Institute (CLSI).

Performance standards for reference strains are assessed within the same experimental design to maintain quality control. See, for example, Clinical Laboratory Standards Institute: Methods for dilution antimicrobial susceptibility tests for bacteria that grow aerobically M7-A8. Approved Standard-Eighth Edition. Wayne, Pa.: CLSI; December 2008; and Clinical Laboratory Standards Institute: Performance Standards for Antimicrobial Susceptibility Testing M100-S20; Approved Standard-Twentieth Edition. Wayne, Pa.: CLSI; June 2010.

For example, an agar-dilution MIC assay could be run using the following protocol. Pure cultures of isolates to be tested are grown on Chocolate Agar at 35° C. to 36.5° C. in a $CO_2$ enriched (5%) atmosphere for 16-18 hours. Using a cotton applicator or a bacteriologic loop, isolated colonies (or cells from less dense areas of growth on the plate) are suspended in 5 mL saline. The density of the suspension is then adjusted to contain 10' colony forming units (CFU)/ml by comparison with a 0.5 McFarland $BaSO_4$ turbidity standard. This suspension is then diluted in 1:10 in MH broth to give $10^7$ CFU/ml. Using a multichannel pipettor, 0.002 mL spots of the bacterial suspension is dispensed onto the surface of the medium, i.e., 104 CFU. Each plate of the set of antibiotic containing media plus a plate of Chocolate Agar or GCS medium (as a control to determine that all isolates grew) is inoculated. The inoculated plates are air-dried at room temperature for approximately 15 minutes. The plates are then inverted and incubated at 35° C. to 36.5° C. in a $CO_2$-enriched (5%) atmosphere for 24 hours. The plates are then examined for growth.

Another in vitro assay that can be performed is a time-kill kinetic assay. Using this assay, bactericidal activity can be determined by time-kill methodology as described by Clinical Laboratory Standards Institute. For example, the compounds to be tested are added to test flasks at concentrations of 2×-32× the MIC (determined, for example, using the assays described herein). Once dissolved, compounds are diluted in Giolitti Cantoni (GC) broth to a volume of 1 mL at the 25× desired final concentration; a flask containing 1 mL of GC broth without compound is prepared as a growth control. A 0.5 McFarland equivalent is prepared for the test organism, diluted 1:200 in pre-warmed GC broth, and incubated in 5% $CO_2$-enriched atmosphere at 35° C. for 30 minutes prior to exposure to the test compound. After the 30-minute pre-incubation, 24 mL is removed and added to each test flask for a final volume of 25 mL. A sample is removed from the growth control flask, diluted in Phosphate Buffered Saline (PBS) and plated on Chocolate Agar (CA) to confirm an inoculum of approximately $5 \times 10^5$ CFU/mL. Samples are then removed from all flasks at 1, 2, 4, 6, 8, and 24 hours, diluted in PBS and plated on CA to determine the number of viable cells in each flask. Plate counts are incubated at 35° C. in 5% $CO_2$-enriched atmosphere for 48 hours and colonies are counted. Plate counts are then graphed.

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

(5) Animal Pharmacology and Toxicology. The compounds of the present disclosure can be evaluated for efficacy in well-known animal models. The following table provides representative animal models for various infection indications.

| Target Infection Indication | Animal Model of Efficacy |
| --- | --- |
| HAP/VAP | Efficacy in mouse and/or rat pneumoniae model vs. respiratory tract infection pathogens of interest (*Streptococcus pneumoniae*, including multi-drug resistant *Streptococcus pneumoniae*, *H influenzae*, methicillin resistant *Staphylococcus aureus* (MRSA), and *Pseudomonas. aeruginosa*) |
| cSSSI | Efficacy in mouse model against pathogens of interest (MRSA, *K pneumoniae*) |
| Sepsis | Efficacy in mouse peritonitis model vs. pathogens of interest (*E. coli*, *K pneumoniae*, *E. faecalis*, MRSA) |
| cUTI | Efficacy in mouse model against *E. coli*, *K pneumoniae* and/or MRSA) |
| Febrile neutropenia | Efficacy in mouse peritonitis model against *S. aureus*, *S. epidermidis*, *S. pneumoniae*, *S. pyogenes*, *P. aeruginosa* |

Animal Model for Complicated Skin and Skin Structure Infections (cSSSI): Murine Skin and Soft Tissue Infection Model of *Klebsiella pneumoniae* 1705966 in Thighs of Neutropenic Female CD-1 Mice This model is useful to assess the efficacy of compounds of the present disclosure in a *Klebsiella pneumoniae* 1705966 neutropenic mouse thigh infection model using female ICR (CD-1) mice.

Study Design:

Species: Female ICR (CD-1) Mice, 8 to 9 weeks old, weighting 25-29 g.

Inoculum: *Klebsiella pneumoniae* 17059663 was streaked from frozen stock onto Blood agar (Tryptic Soy Agar+ 5% Sheep Blood), BD, #221261) and incubated overnight at 35° C. After overnight incubation, enough bacteria (approx. 1 full loop) to measure $OD_{625}$=0.990 was transferred from plate and diluted into 10 ml pre-warmed Mueller-Hinton broth. This culture was further diluted 1:1000 into pre-warmed MH broth and grown for approximately 2 hours at 35° C. with shaking. Each mouse was given 0.1 mL of 1:1000 dilution culture injected into both caudal thigh muscles under isoflurane inhalation anesthesia.

| Dilution | Initial O.D. | Final O.D. (after ~2 hr. incubation) |
| --- | --- | --- |
| 1:10 | 0.135 | 0.424 |
| 1:100 | 0.014 | 0.215 |
| 1:1000 | 0.001 | 0.035 |

Neutropenia is induced by intraperitoneal (I.P.) administration of Cyclophosphamide monohydrate on Day −4 (150 mg/kg) and Day −1 (100 mg/kg).

Vehicle: 0.9% sodium chloride

Dosing: Each mouse in the treated groups was given the appropriate dose of the compound to be tested in a volume of 0.2 ml, 2 and 8 hrs. post bacterial inoculation.

Time points:
Controls: 0, 2, 6, and 24 hrs.
Treated: 24 hrs.
Sampling: 2 or 3 mice/time point were euthanized via $CO_2$, and their caudal thigh muscles excised and homogenized. The thigh muscles were placed in 5 ml sterile PBS in Stomacher Filter bag and homogenized with MicroBiomaster80 (Brinkmann) for 60 seconds, normal setting and 1:10 dilutions were made per standard protocol in a 96-well plate. Aliquots of 25 ul for each dilution, as well as the homogenate, were plated on blood agar plates and incubated at 35° C. to determine the CFU/mL over the time course. After overnight incubation, colonies were counted.

Animal Model for Sepsis:
Murine Peritonitis Model (*E. coli, K. Pneumoniae, E. Faecalis*, MRSA)
This model is used to evaluate the effect of subcutaneous (SC) treatment with compounds of the present disclosure on growth of *Escherichia coli* ATCC 25922 in a mouse peritonitis model using female Swiss Webster mice.

Controls:
  Negative: Inoculum only
  Inoculum Vehicle Intraperitoneal
  Positive: Ciprofloxacin
Study Design:
  Species: Female Swiss Webster Mice
  Inoculation: *Escherichia coli* ATCC 25922 is made by adding 1 ml (Apr. 6, 2007) stock to 9 ml 0.25% Brewer's Yeast to make (1:10), then 1 ml of the (1:10) will be added to 9 ml 0.25% Brewer's Yeast to make (1:100), then 1 ml of the (1:100) will be added to 9 ml 0.25% Brewer's Yeast to make (1:1000), then 2.5 ml of the (1:1000) will be added to 122.5 ml 0.25% Brewer's Yeast to make (1:50,000), 1 ml/mouse will be inoculated intraperitoneally (IP).
Route of Administration: SC
  Dosing: Vehicle for compounds of the present disclosure: Saline or 50 mM Sodium phosphate buffer in 10% Captisol in water, pH=7.2.
  Dose Administration: Q3H×3 beginning at 30 min post bacterial inoculation
  Study Duration: 24 hrs. 0.25% Brewer's Yeast Extract (BYE): Dilute 2% prepared on 11/12/09 (Lot. 2158K, MP Biomedicals) 25 ml 2%+175 ml 1×PBS.
  Outcome Measures: Colony Forming Unit's from peritoneal wash and spleen homogenate and drug levels from wash, spleen homogenate, and plasma.
  Blood is collected via cardiac puncture while mouse is under $CO_2$ narcosis. The whole blood sample is placed in heparinized eppendorf tubes and kept on wet ice until centrifuged (4 min @ 14,000 rpm). Plasma is transferred to 96 deep-well block on dry ice and stored at −20° C. Immediately following blood collection, 2 ml of sterile PBS (phosphate buffered saline) was injected into the peritoneal cavity with a 25 G needle. The abdomen was gently massaged, and a small incision was made to allow access to the peritoneal cavity. The peritoneal wash fluid was collected using sterile technique, serially diluted 1:10, plated on blood agar plates, and incubated overnight at 35° C.
  Spleens were harvested and placed in 1 ml sterile PBS in Stomacher bag and homogenized with MicroBiomaster80 (Brinkmann) for 60 seconds, normal setting and 1:10 dilutions were made. 25 µl of each dilution, as well as the homogenate, was plated on blood agar plates and incubated at 35° C. to determine the CFU/mL over the time course. After overnight incubation, colonies were counted.

Other Animal Models
Similarly, other animal infection models can be used for hospital acquired pneumonia (HAP)/ventilator acquired pneumonia (VAP), complicated urinary tract infections (cUTI), and febrile neutropenia.

5. Formulation and Administration

The compositions and methods of the present disclosure can be practiced by delivering the compounds of the present disclosure using a means for delivery e.g., any suitable carrier. The dose of active compound, mode of administration and use of suitable carrier will depend upon the intended patient or subject and the targeted microorganism, e.g., the target bacterial organism. The formulations, both for human medical use and veterinary use, of compounds according to the present disclosure typically include such compounds in association with a pharmaceutically acceptable carrier.

The carrier(s) should be "acceptable" in the sense of being compatible with compounds of the present disclosure and not deleterious to the recipient. Pharmaceutically acceptable carriers, in this regard, are intended to include any and all solvents, dispersion media, coatings, absorption delaying agents, and the like, compatible with pharmaceutical administration. Supplementary active compounds (identified or designed according to the disclosure and/or known in the art) also can be incorporated into the compositions. In some embodiments, formulations are prepared by bringing the compound into association with a liquid carrier or a finely divided solid carrier or both, and then, if necessary, shaping the product into the desired formulation.

A pharmaceutical composition of the disclosure should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present disclosure suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants can include, for example, for transmucosal administration, detergents and bile salts. Transmucosal administration can be accomplished through the use of nasal sprays or suppositories. For transdermal administration, the active compounds typically are formulated into ointments, salves, gels, or creams.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Liposomal suspensions can also be used as pharmaceutically acceptable carriers.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively, or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations disclosed herein. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

Generally, an effective amount of dosage of active compound will be in the range of from about 0.1 mg/kg to about 100 mg/kg of body weight/day, for example, from about 1.0 mg/kg to about 50 mg/kg of body weight/day. In some embodiments, the dosage of active compound is in the range of from about 0.1 mg/kg to about 1.0 mg/kg of body weight/day; from about 0.1 mg/kg to about 5 mg/kg of body weight/day; from about 0.1 mg/kg to about 10 mg/kg of body weight/day; from about 0.1 mg/kg to about 25 mg/kg of body weight/day; from about 0.1 mg/kg to about 50 mg/kg of body weight/day; from about 1.0 mg/kg to about 5.0 mg/kg of body weight/day; from about 1.0 mg/kg to about 10 mg/kg of body weight/day; from about 1.0 mg/kg to about 20 mg/kg of body weight/day; from about 1.0 mg/kg to about 25 mg/kg of body weight/day; from about 1.0 mg/kg to about 40 mg/kg of body weight/day; from about 1.0 mg/kg to about 100 mg/kg of body weight/day; from about 10 mg/kg to about 100 mg/kg of body weight/day; from about 25 mg/kg to about 100 mg/kg of body weight/day; from about 50 mg/kg to about 100 mg/kg of body weight/day; from about 5.0 mg/kg to about 50 mg/kg of body weight/day; from about 10 mg/kg to about 50 mg/kg of body weight/day; or from about 25 mg/kg to about 50 mg/kg of body weight/day.

The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 mg to about 1500 mg per dose. For example, a dose of active compound can range from about 0.1 mg to about 1250 mg; about 0.1 mg to about 1000 mg; about 0.1 mg to about 800 mg; about 0.1 mg to about 500 mg; about 0.1 mg to about 250 mg; about 0.1 mg to about 100 mg; about 0.1 mg to about 50 mg; about 0.1 mg to about 25 mg; about 0.1 mg to about 20 mg; about 0.1 mg to about 10 mg; about 0.1 mg to about 5 mg; about 0.1 mg to about 1 mg; about 0.1 mg to about 0.5 mg; about 0.5 mg to about 1500 mg; about 1 mg to about 1500 mg; about 2.5 mg to about 1500 mg; about 5 mg to about 1500 mg; about 10 mg to about 1500 mg; about 50 mg to about 1500 mg; about 100 mg to about 1500 mg; about 250 mg to about 1500 mg; about 500 mg to about 1500 mg; about 750 mg to about 1500 mg; about 1000 mg to about 1500 mg; about 1250 mg to about 1500 mg; about 0.25 mg to about 2.5 mg; about 0.5 mg to about 5 mg; about 1 mg to about 10 mg; about 5 to about 20 mg; about 10 mg to about 50 mg; about 25 mg to about 75 mg; about 20 mg to about 100 mg; about 50 mg to about 200 mg; about 100 mg to about 500 mg; about 250 mg to about 750 mg; about 200 mg to about 800 mg; about 500 mg to about 1000 mg; or about 750 mg to about 1250 mg.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e., minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. The another way, about 272 mg of the monosodium salt would be equivalent to a 250 mg dosage of the parent or active compound.

In some embodiments, pyrrolocytosines, such as the compounds or tautomers thereof, or pharmaceutically acceptable salts of the compounds or tautomers, as provided herein, can exhibit an acute clinical syndrome, which manifests as a $C_{max}$-driven hemodynamic effect and is associated with immediate clinical signs such as labored breathing. $C_{max}$ is the peak concentration a molecule reaches in the plasma (e.g., directly following intravenous administration), and is expressed generally in micrograms/milliliter. The syndrome is dose-dependent, meaning that the higher the amount of drug given, the more severe are the effects. In some embodiments, this is the limiting toxicity for the class. In some embodiments, however, the efficacy for the pyrrolocytosines, including the compounds or tautomers thereof, or pharmaceutically acceptable salts of the compounds or tautomers, as provided herein, is not driven by the $C_{max}$ but rather by the AUC (Area-Under-the-plasma-drug-concentration-time-Curve), which is an expression of the total body exposure to the drug and is expressed generally in micrograms*hour/milliliter. In rat studies with several pyrrolocytosines, including selected compounds or tautomers thereof, or pharmaceutically acceptable salts of the compounds or tautomers as provided herein, it has been shown that increasing the length, or duration, of the intravenous administration results in one or more of effectively modulating or eliminating the clinical syndrome and depressing the concentration maximum. In some embodiments, these effects result in a short distribution half-life but still afford drug exposures necessary for efficacy.

FORMULATION EXAMPLES

IA. Formulation for Intravenous Administration

| Ingredients | Amount |
| --- | --- |
| Antimicrobial Compound of the present disclosure | 0.1-1500 total mg |
| Dextrose, USP | 50 mg/ml |
| Sodium citrate, USP | 1.60-1.75 mg/ml |
| Citric Acid, USP | 0.80-0.90 mg/ml |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.

This formulation is useful for intravenous administration, either bolus or infusion, to a patient for treating, preventing, reducing the risk of, or delaying the onset of infection.

IB. Formulation for Intravenous Administration

This formulation for intravenous administration utilizes 6.5 nM tartaric acid buffer in 5% Dextrose, and has a pH of 4.4. This formulation is useful for intravenous administration, either bolus or infusion, to a patient for treating, preventing, reducing the risk of, or delaying the onset of infection.

II. Lyophilisate for Reconstitution

Alternatively, the antimicrobial compound can be provided as a lyophilisate which can be reconstituted before intravenous or intramuscular administration.

| Ingredient | mg per injection vial |
| --- | --- |
| Antimicrobial Compound of the present disclosure | 0.1-1500 |
| Cyclodextrin | 1500 |

Reconstitution solution for a volume to be administered of 50 ml (infusion): 5% aqueous glucose solution.
Reconstitution solution for a volume to be administered of 15 ml (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

III. Lyophilisate for Reconstitution

| Ingredient | mg per injection vial |
| --- | --- |
| Antimicrobial Compound of the present disclosure | 0.1-1500 |
| soya lecithin | 2250 |
| Sodium cholate | 1500 |

Reconstitution solution for a volume to be administered of 50 ml (infusion): 4% aqueous glucose solution.
Reconstitution solution for a volume to be administered of 15 ml (bolus): 2% aqueous glucose solution The foregoing lyophilisate is useful for reconstitution and intravenous administration, either bolus or infusion, to a patient for treating, preventing, reducing the risk of, or delaying the onset of infection.

IV. Lyophilisate for Reconstitution

| Ingredient | mg per injection vial |
| --- | --- |
| Antimicrobial Compound of the present disclosure | 0.1-1500 |
| soya lecithin | 900 |
| Sodium glycocholate | 540 |

Reconstitution solution for a volume to be administered of 15 ml (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

V. Tablet for Oral Administration

| V. Tablet for Oral Administration | | |
| --- | --- | --- |
| Ingredients | Per Tablet | Per 4000 Tablets |
| Antimicrobial Compound of the present disclosure | 0.1-1500 mg | 0.4-6000 g |
| Anhydrous Lactose, NF | 110.45 mg | 441.8 g |
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Croscarmellose sodium is added to the blended powders and mixed for 5 minutes at 20 RPM. Finally, the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient for treating, prevention, reducing the risk of, or delaying the onset of infection.

6. Examples

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds or tautomers thereof, or pharmaceutically acceptable salts of the compounds or tautomers of the present disclosure can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; μM=micromolar; g=gram(s); μg=microgram(s); rt=room temperature; L=liter(s); mL=milliliter(s); Et$_2$O=diethyl ether; THF=tetrahydrofuran; DMSO=dimethyl sulfoxide; EtOAc=ethyl acetate; Et$_3$N=triethylamine; i-Pr$_2$NEt or DIPEA=diisopropylethylamine; CH$_2$Cl$_2$=methylene chloride; CHCl$_3$=chloroform; CDCl$_3$=deuterated chloroform; CCl$_4$=carbon tetrachloride; MeOH=methanol; CD$_3$OD=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCI=t-butyldiphenylchlorosilane; Hunig's Base=N,N-diisopropylethylamine; DMAP=4-dimethylaminopyridine; CuI=copper (I) iodide; MsCl=methanesulfonyl chloride; NaN$_3$=sodium azide; Na$_2$SO$_4$=sodium sulfate; NaHCO$_3$=sodium bicarbonate; NaOH=sodium hydroxide; MgSO$_4$=magnesium sulfate; K$_2$CO$_3$=potassium carbonate; KOH=potassium hydroxide; NH$_4$OH=ammonium hydroxide; NH$_4$Cl=ammonium chloride; SiO$_2$=silica; Pd—C=palladium on carbon; Pd(dppf)Cl$_2$=dichloro[1,1'-bis(diphenylphosphino)ferrocene]palladium (II); Cs$_2$CO$_3$=cesium carbonate; Zn=zinc; LiCl=lithium chloride; DMF=N,N-dimethylformamide; 9-BBN=9-Borabicyclo[3.3.1]nonane; K$_3$PO$_4$=potassium phosphate; DMA=N,N-dimethylacetamide; DIBAL and DIBAL-H=diisobutylaluminum hydride; n-CPBA=meta-chloroperoxybenzoic acid; KOAc=potassium acetate; B$_2$Pin$_2$=bis(pinacolato)diboron; Cu(OAc)$_2$=copper (II) acetate; TMEDA=tetramethylethylenediamine; Bz$_2$O=benzoyl anhydride; DIPEA=N,N-diisopropylethylamine; Pd(PPh$_3$)$_4$=tetrakis(triphenylphosphine)palladium (0); TEA=triethylamine; MsCl=mesityl chloride; HBr=hydrogen bromide; AcOH=acetic acid; IPAC=isopropyl acetate; EDTA=ethylenediaminetetraacetic acid.

Exemplary compounds synthesized in accordance with the disclosure are listed in Tables 1. A bolded or dashed bond is shown to indicate a particular stereochemistry at a chiral center, whereas a wavy bond indicates that the substituent can be in either orientation or that the compound is a mixture thereof.

The compounds of the present disclosure can be prepared, formulated, and delivered as salts. For convenience, the compounds are generally shown without indicating a particular salt form.

The compounds of the present disclosure can be made using synthetic chemical techniques well known to those of skill in the art.

Example 1: Syntheses of Compound 7

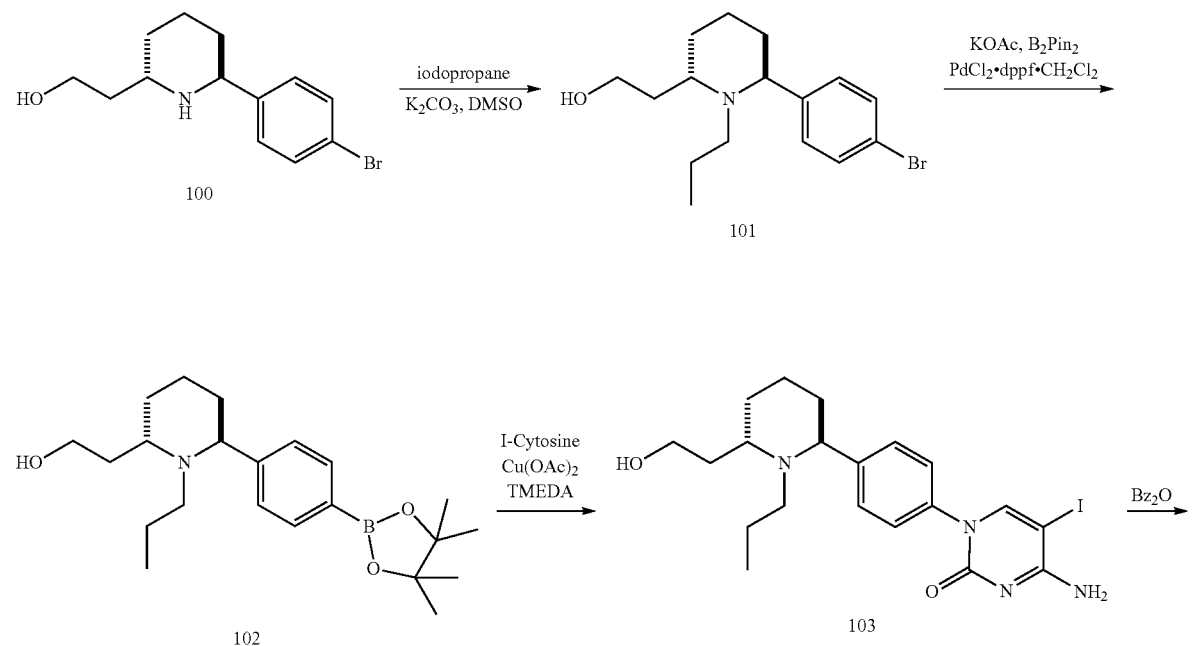

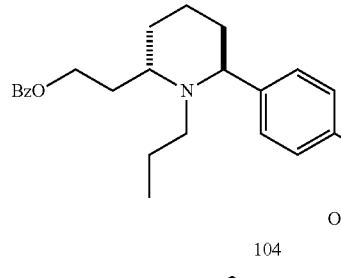
104
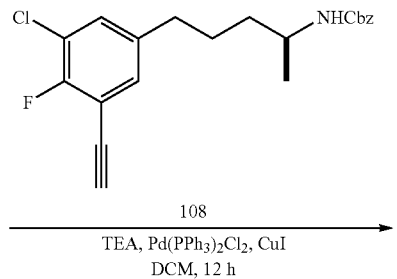
108
TEA, Pd(PPh₃)₂Cl₂, CuI
DCM, 12 h
-continued
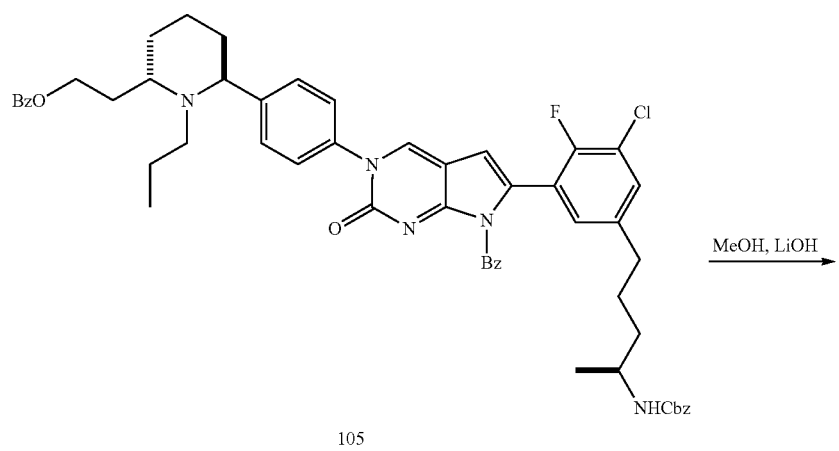
105
MeOH, LiOH
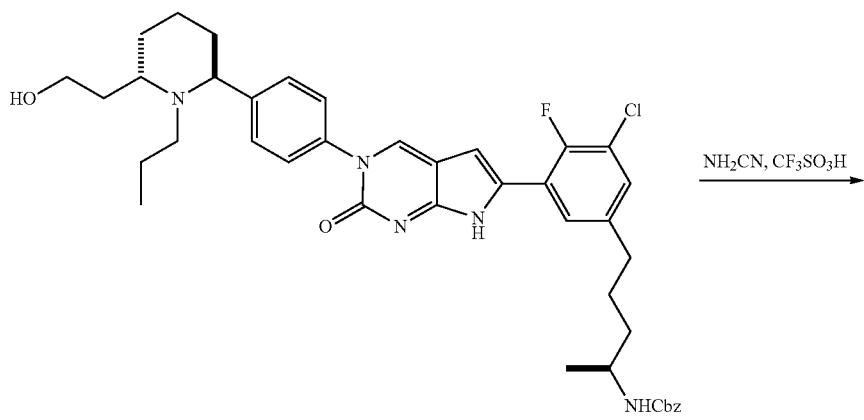
106
NH₂CN, CF₃SO₃H
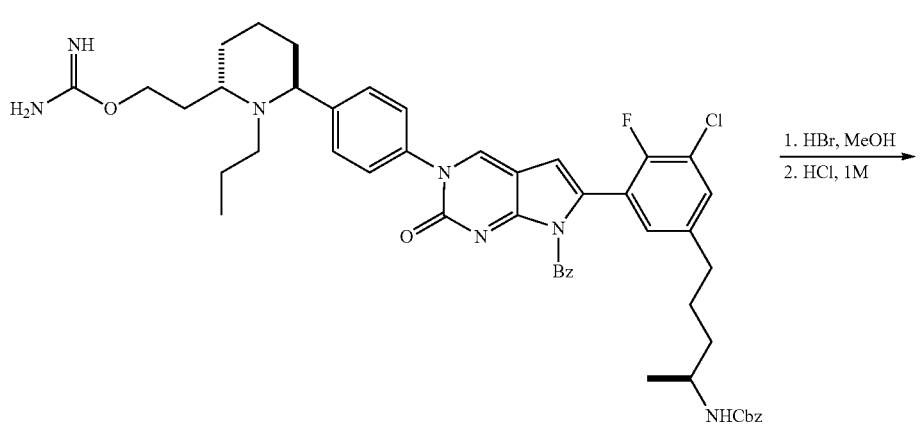
107
1. HBr, MeOH
2. HCl, 1M -continued

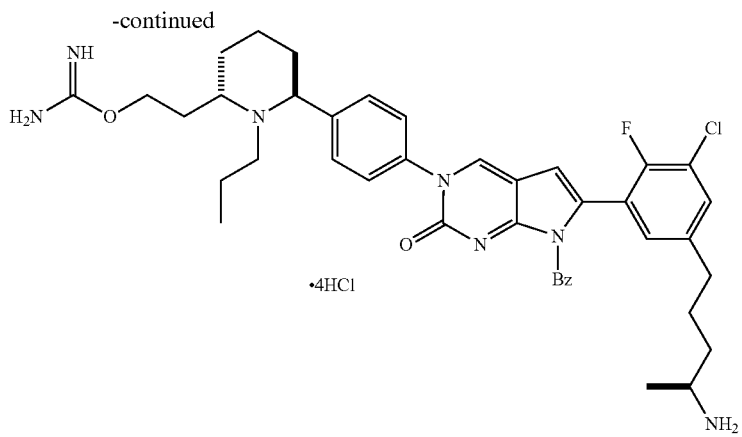

7

Experimental Procedure

Compound 101

To a solution of 100 (2.0 g, 6.4 mmol) in dimethylsulfoxide (1 mL) was added potassium carbonate (2.7 g, 19 mmol) and 1-iodopropane (3.3 g, 19 mmol). The reaction mixture was stirred at 65° C. for 6 hours, after which it was quenched by water (100 mL) at 25° C. The resulting mixture was extracted with ethyl acetate (3×50 mL); the combined organic layers were washed with brine (100 mL), dried over anhydrous sodium sulfate, filtered, and concentrated under reduced pressure to give a residue. The residue was purified by column chromatography (petroleum ether: ethyl acetate=20:1 to 1:1) to give 101 (1.8 g, 84% yield, 98.0% purity) as a yellow solid. LCMS: m/z $(M+H)^+$=328.6

Compound 102

To a solution of 101 (1.8 g, 5.5 mmol) in dimethylsulfoxide (15 mL) was added bis(pinacolato)diboron (4.2 g, 17 mmol), 1,1'-bis(diphenylphosphino)ferrocene-palladium (ii) dichloride dichloromethane complex (0.23 g, 0.28 mmol), and potassium acetate (1.6 g, 17 mmol). The reaction mixture was stirred at 90° C. for 12 hours, and was subsequently quenched by ethyl acetate (20 mL) upon cooling to 25° C. The resulting mixture was diluted with water (30 mL) and extracted with ethyl acetate (3×10 mL). The combined organic layers were washed with brine (50 mL), dried over anhydrous sodium sulfate, filtered, and concentrated under reduced pressure to give a residue. The residue was purified by column chromatography (petroleum ether: ethyl acetate=1:1/0:1 to dichloromethane:methanol=10:1) to give 102 (0.60 g, 27% yield, 91.0% purity) as brown oil. LCMS: m/z $(M+H)^+$=374.3

Compound 103

To a solution of 102 (0.50 g, 1.2 mmol) in methanol (5.0 mL) and water (1 mL) was added 4-amino-5-iodo-1H-pyrimidin-2-one (0.29 g, 1.2 mmol) and copper (II) acetate monohydrate (0.24 g, 1.2 mmol). Tetramethylethylenediamine (0.28 g, 2.4 mmol) was then added. The mixture was stirred at 25° C. for 12 hours under an oxygen balloon (15 psi). The volatiles were evaporated; the resulting residue was treated with 28% ammonium hydroxide (40 mL) and tetrahydrofuran (20 ml). The mixture was stirred for 4 hours until the green precipitate dissolved. Combined organic phases were washed with water (20 mL) and brine (30 mL). The organic extracts were dried over anhydrous sodium sulfate, filtered, and concentrated in vacuo to give 103 (0.50 g, crude) as brown oil which was used in the next step directly.

Compound 104

To a solution of 103 (0.50 g, 1.0 mmol) in ethyl acetate (5.0 mL) was added benzoic anhydride (0.59 g, 2.6 mmol). The mixture was stirred at 80° C. for 12 hours, after which it was concentrated in vacuo to give a crude residue. The residue was purified by column chromatography (petroleum ether: ethyl acetate=1:0 to 1:1 to dichloromethane:methanol=10:1) to give 104 (0.40 g, 40% yield, 71.0% purity) as light yellow oil. LCMS: m/z $(M+H)^+$=691.2

Compound 105

To a solution of 104 (0.40 g, 0.41 mmol) and alkyne 108 (0.18 g, 0.45 mmol) in dichloromethane (5 mL) was added copper iodide (7.8 mg, 41 μmol), bis(triphenylphosphine)palladium(ii)dichloride (14 mg, 21 μmol), and triethylamine (124 mg, 1.2 mmol). The mixture was stirred at 40° C. for 12 hours and was then concentrated under reduced pressure to give 105 (0.50 g, crude) as brown oil, which was used in the next step directly.

Compound 106

To a solution of 105 (0.60 g, 0.64 mmol) in methanol (5 mL) was added lithium hydroxide (2.0 M in water, 1.28 mL). The mixture was stirred at 60° C. for 4 hours and was subsequently cooled down to room temperature. Methanol was then evaporated, and the reaction mixture was treated with water (30 mL) and extracted with ethyl acetate (3×10 mL). The combined organic layers were washed with brine (50 mL), dried over anhydrous sodium sulfate, filtered, and concentrated under reduced pressure to give a residue. The residue was purified by column chromatography (petroleum ether: ethyl acetate=5:1 to 1:1). Then the residue was purified by prep-HPLC (column: Phenomenex luna C18 250*50 mm*10 um; mobile phase: [water (0.225% TFA)-ACN]; B %: 30 ACN %-60 ACN %, 30 min; 50% min) to 106 (0.30 g, 43% yield, 67.0% purity) as a yellow solid. LCMS: m/z $(M+H)^+$=728.2.

Compound 107

To a solution of 106 (0.20 g, 0.27 mmol) in anhydrous tetrahydrofuran (1.0 mL) was added cyanamide (0.10 g, 2.5 mmol) at 0° C. Trifluoromethanesulfonic acid (0.37 g, 2.5 mmol) in anhydrous tetrahydrofuran (0.6 mL) was then added to the mixture at 0° C. over 30 min. The resulting mixture was stirred at 25° C. for 1 hour and was subsequently concentrated under reduced pressure. The resulting residue was purified by prep-HPLC (column: Phenomenex Synergi C18 150*25*10 um; mobile phase: [water (0.1% TFA)-ACN]; B %: 30%-60%, 13 min) to give 107 (50.0 mg, 22.5% yield, 95.0% purity) as a yellow solid. LCMS: m/z $(M+H)^+=770.3$.

Compound 7

A solution of 107 (50 mg, 65 umol) in hydrobromic acid (2 mL) and methanol (1 mL) was stirred at 25° C. for 2 hours. The mixture was concentrated under reduced pressure. The resulting residue was purified by prep-HPLC (column: Phenomenex Synergi C18 150*25*10 um; mobile phase: [water (0.1% TFA)-ACN]; B %: 8%-38%, 12 min). To the combined fraction was then added hydrochloric acid (1.0 M, 10 mL). The resulting mixture was lyophilized at 25° C. for 12 hours to give compound 7 (36.0 mg, 66.0% yield, 93.8% purity, 4 HCl) as a yellow solid. LCMS: m/z $(M+H)^+=636.4$.

Example 2—Antimicrobial Activity

The compounds of the present disclosure were tested for antimicrobial activity. These data are presented in Table 2. The Compounds 1-105 were run against *Escherichia coli* (*E. coli*) strain ATCC25922 and against *Staphylococcus aureus* (*S. aureus*) 11540 strain using a standard microdilution assay to determine minimum inhibitory concentrations (MICs). The data is presented whereby a "+" indicates that the compound has an MIC value of 16 micrograms/mL or less and a "−" indicates that the compound has an MIC value greater than 16 micrograms/mL. It will be recognized by one skilled in the art that the compounds can be assessed against other bacterial organisms and that the presentation of data for activity against *Escherichia coli* and *Staphylococcus aureus* are illustrative and in no way is intended to limit the scope of the present disclosure. The compounds of the present disclosure can be assayed against a range of other microorganisms depending upon the performance activity desired to be gathered. Furthermore, the "+" and "−" representation and the selection of a cutoff value of 16 micrograms/mL is also illustrative and in no way is intended to limit the scope of the present disclosure. For example, a "−" is not meant to indicate that the compound necessarily lacks activity or utility, but rather that its MIC value against the indicated microorganism is greater than 16 micrograms/mL.

TABLE 2

| # | MIC S. aureus | MIC E.coli |
|---|---|---|
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |
| 10 | + | + |
| 11 | + | + |
| 12 | + | + |
| 13 | + | + |
| 14 | + | + |
| 15 | + | + |
| 16 | + | + |
| 17 | + | + |
| 18 | + | + |
| 19 | + | + |
| 20 | + | + |

INCORPORATION BY REFERENCE

The entire disclosure of each of the patent documents and scientific articles referred to herein is incorporated by reference for all purposes.

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A compound of Formula (A):

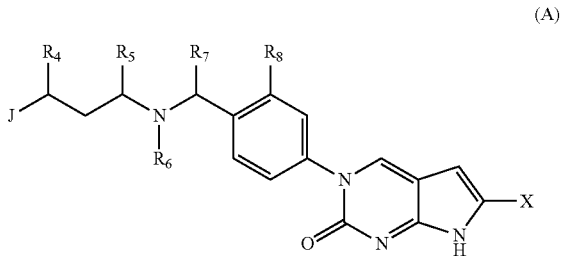

or a pharmaceutically acceptable salt, stereoisomer, or tautomer thereof, wherein:

J is:

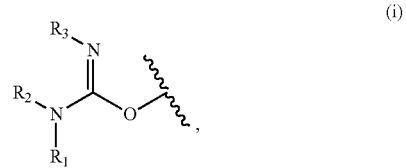

wherein:
$R_1$ is H or $C_{1-3}$ alkyl;
$R_2$ is H or $C_{1-3}$ alkyl; and
$R_3$ is H or $C_{1-3}$ alkyl; or

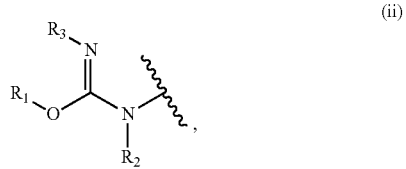

wherein:
(a) $R_1$ is $C_{1-3}$ alkyl;
$R_2$ is H or C1-3 alkyl; and
$R_3$ is H or C1-3 alkyl; or (b) $R_1$ is H or C1-3 alkyl;
$R_2$ is $C_{1-3}$ alkyl; and
$R_3$ is H or C1-3 alkyl; or
(c) $R_1$ is H or C1-3 alkyl;
$R_2$ is H or C1-3 alkyl; and
$R_3$ is $C_{1-3}$ alkyl;
$R_4$ is H or C1-3 alkyl;
(A) $R_5$ is H or $C_{1-6}$ alkyl; and
$R_6$ and $R_7$, together with the carbon and nitrogen atoms to which they are attached, form a heterocyclyl having any of the following formulas:

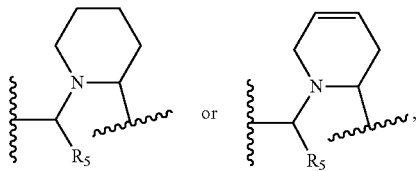

wherein the heterocyclyl is optionally substituted on a ring carbon atom with a $C_{1-6}$ alkyl substituent; and
wherein the $C_{1-6}$ alkyl substituent is optionally substituted with one or more OH substituents; or
(B) $R_5$ and $R_7$, together with the carbon and nitrogen atoms to which they are attached, form a heterocyclyl having any of the following formulas:

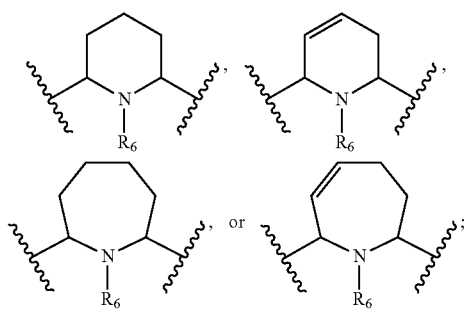

$R_6$ is H, $C_{1-6}$ alkyl, $C_{2-6}$ alkenyl, or $C_{3-6}$ cycloalkyl, wherein the $C_{1-6}$ alkyl is optionally substituted with one or more substituents independently selected from the group consisting of halogen, $C(O)OR^a$, $OR^a$, $SR^a$, $SC(NH)NH_2$, $C_{3-6}$ cycloalkyl, and 3- to 6-membered heterocyclyl; and
each $R^a$ is independently H or $C_{1-6}$ alkyl;
$R_8$ is H or halogen;
X is a 5- or 6-membered heterocyclyl or phenyl, wherein the 5- or 6-membered heterocyclyl or phenyl is optionally substituted with one or more independently selected $R^x$ substituents;
each $R^x$ is independently halogen, $C_{1-6}$ alkyl, $C_{1-4}$ haloalkyl, $C(O)R^c$, $C(O)OR^c$, $NR^cR^c$, $OR^c$, $C_{3-6}$ cycloalkyl, or aryl, wherein each $C_{1-6}$ alkyl is optionally and independently substituted with one or more independently selected $R^b$ substituents; or
two adjacent $R^x$, together with the atoms to which they are attached, form a 5- or 6-membered ring;
each $R^b$ is independently $C_{2-6}$ alkenyl, $C(O)OR^c$, $NR^cR^c$, $OR^c$, $OC(NH)NH_2$, $C_{3-6}$ cycloalkyl, or aryl;
each $R^c$ is independently H, $C_{1-6}$ alkyl, $CH_2$-aryl, $C(O)$ aryl, or aryl, wherein each $C_{1-6}$ alkyl and each aryl is optionally and independently substituted with one or more independently selected $R^d$ substituents; and
each $R^d$ is independently $C_{1-3}$ alkyl, $NH_2$, $NHC_{1-3}$ alkyl, $N(C_{1-3}$ alkyl$)_2$, $NO_2$, OH, or $OC_{1-3}$ alkyl.

2. The compound of claim 1, or a pharmaceutically acceptable salt, stereoisomer, or tautomer thereof, wherein:
(a) $R_1$ is $C_{1-3}$ alkyl;
$R_2$ is H; and
$R_3$ is H; or
(b) $R_1$ is H;
$R_2$ is $C_{1-3}$ alkyl; and
$R_3$ is H; or
(c) $R_1$ is H;
$R_2$ is H; and
$R_3$ is $C_{1-3}$ alkyl.

3. The compound of claim 2, or a pharmaceutically acceptable salt, stereoisomer, or tautomer thereof, wherein:
(a) $R_1$ is $CH_3$;
$R_2$ is H; and
$R_3$ is H; or
(b) $R_1$ is H;
$R_2$ is $CH_3$; and
$R_3$ is H; or
(c) $R_1$ is H;
$R_2$ is H; and
$R_3$ is $CH_3$.

4. The compound of claim 1, or a pharmaceutically acceptable salt, stereoisomer, or tautomer thereof, wherein:
(a) $R_1$ is $C_{1-3}$ alkyl;
$R_2$ is H; and
$R_3$ is $C_{1-3}$ alkyl; or
(b) $R_1$ is $C_{1-3}$ alkyl;
$R_2$ is $C_{1-3}$ alkyl; and
$R_3$ is H; or
(c) $R_1$ is H;
$R_2$ is $C_{1-3}$ alkyl; and
$R_3$ is $C_{1-3}$ alkyl.

5. The compound of claim 4, or a pharmaceutically acceptable salt, stereoisomer, or tautomer thereof, wherein:
(a) $R_1$ is $CH_3$;
$R_2$ is H; and
$R_3$ is $CH_3$; or
(b) $R_1$ is $CH_3$;
$R_2$ is $CH_3$; and
$R_3$ is H; or
(c) $R_1$ is H;
$R_2$ is $CH_3$; and
$R_3$ is $CH_3$.

6. The compound of claim 1, or a pharmaceutically acceptable salt, stereoisomer, or tautomer thereof, wherein $R_5$ and $R_7$, together with the carbon and nitrogen atoms to which they are attached, form:

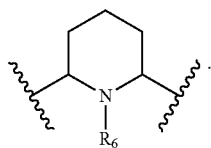

7. The compound of claim 1, or a pharmaceutically acceptable salt, stereoisomer, or tautomer thereof, wherein $R_5$ and $R_7$, together with the carbon and nitrogen atoms to which they are attached, form:

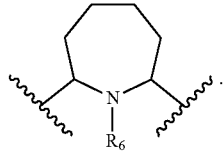

8. The compound of claim 1, or a pharmaceutically acceptable salt, stereoisomer, or tautomer thereof, wherein $R_5$ and $R_7$, together with the carbon and nitrogen atoms to which they are attached, form:

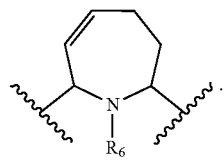

9. The compound of claim 1, or a pharmaceutically acceptable salt, stereoisomer, or tautomer thereof, wherein $R_6$ is $C_{1-6}$ alkyl, wherein the $C_{1-6}$ alkyl is substituted with one or more independently selected halogen substituents.

10. The compound of claim 1, or a pharmaceutically acceptable salt, stereoisomer, or tautomer thereof, wherein $R_6$ is $C_{1-6}$ alkyl, wherein the $C_{1-6}$ alkyl is substituted with one or more independently selected $OR^a$ substituents.

11. The compound of claim 1, or a pharmaceutically acceptable salt, stereoisomer, or tautomer thereof, wherein $R_6$ is $C_{1-6}$ alkyl, wherein the $C_{1-6}$ alkyl is substituted with one or more $SC(NH)NH_2$ substituents.

12. The compound of claim 1, or a pharmaceutically acceptable salt, stereoisomer, or tautomer thereof, wherein $R_6$ and $R_7$, together with the carbon and nitrogen atoms to which they are attached, form:

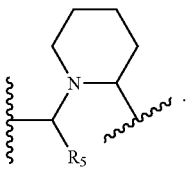

13. The compound of claim 1, or a pharmaceutically acceptable salt, stereoisomer, or tautomer thereof, wherein $R_6$ and $R_7$, together with the carbon and nitrogen atoms to which they are attached, form:

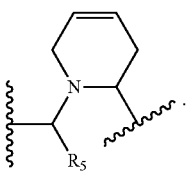

14. The compound of claim 1, or a pharmaceutically acceptable salt, stereoisomer, or tautomer thereof, wherein X is pyrrolidinyl, wherein the pyrrolidinyl is optionally substituted with one or more independently selected $R^x$ substituents.

15. The compound of claim 1, or a pharmaceutically acceptable salt, stereoisomer, or tautomer thereof, wherein X is phenyl, wherein the phenyl is optionally substituted with one or more independently selected $R^x$ substituents.

16. The compound of claim 1, or a pharmaceutically acceptable salt, stereoisomer, or tautomer thereof, wherein each $R^x$ is independently halogen or $C_{1-6}$ alkyl, wherein each $C_{1-6}$ alkyl is optionally and independently substituted with one or more independently selected $R^b$ substituents.

17. The compound of claim 1, or a pharmaceutically acceptable salt, stereoisomer, or tautomer thereof, wherein two adjacent $R^x$, together with the atoms to which they are attached, form a 5- or 6-membered ring.

18. The compound of claim 1, or a pharmaceutically acceptable salt, stereoisomer, or tautomer thereof, wherein each $R^b$ is independently $CH{=}CH_2$, $NH_2$, or OH.

\* \* \* \* \*